US012139711B2

(12) United States Patent
Collin et al.

(10) Patent No.: US 12,139,711 B2
(45) Date of Patent: *Nov. 12, 2024

(54) ANTISENSE OLIGONUCLEOTIDES FOR THE TREATMENT OF LEBER CONGENITAL AMAUROSIS

(71) Applicant: Stichting Radboud universitair medisch centrum, Nijmegen (NL)

(72) Inventors: Robert Wilhelmus Johanna Collin, Venlo (NL); Franciscus Peter Maria Cremers, Malden (NL); Antonia Ingrid Den Hollander, Groesbeek (NL)

(73) Assignee: Stichting Radboud universitair medisch centrum, Nijmegen (NL)

( * ) Notice: Subject to any disclaimer, the term of this patent is extended or adjusted under 35 U.S.C. 154(b) by 257 days.

This patent is subject to a terminal disclaimer.

(21) Appl. No.: 17/678,433

(22) Filed: Feb. 23, 2022

(65) Prior Publication Data

US 2022/0235355 A1 Jul. 28, 2022

Related U.S. Application Data

(63) Continuation of application No. 16/842,157, filed on Apr. 7, 2020, now Pat. No. 11,279,933, which is a continuation of application No. 16/197,865, filed on Nov. 21, 2018, now Pat. No. 10,647,985, which is a continuation of application No. 15/963,229, filed on Apr. 26, 2018, now Pat. No. 10,167,470, which is a continuation of application No. 15/656,635, filed on Jul. 21, 2017, now abandoned, which is a continuation of application No. 14/342,776, filed as application No. PCT/NL2012/050275 on Apr. 25, 2012, now Pat. No. 9,771,580.

(60) Provisional application No. 61/531,137, filed on Sep. 6, 2011.

(30) Foreign Application Priority Data

Sep. 5, 2011 (NL) .................................... 2007351

(51) Int. Cl.
*C12N 15/113* (2010.01)

(52) U.S. Cl.
CPC ........ *C12N 15/113* (2013.01); *C12N 2310/11* (2013.01); *C12N 2310/15* (2013.01); *C12N 2310/321* (2013.01); *C12N 2310/346* (2013.01); *C12N 2320/33* (2013.01); *C12N 2320/34* (2013.01)

(58) Field of Classification Search
None
See application file for complete search history.

(56) References Cited

U.S. PATENT DOCUMENTS

| 6,875,736 B2 | 4/2005 | Rana |
| 7,517,644 B1 | 4/2009 | Smith |
| 9,012,425 B2 * | 4/2015 | Rozet .................. C12N 15/113 536/24.5 |
| 9,487,782 B2 | 11/2016 | Rozet et al. |
| 9,771,580 B2 | 9/2017 | Collin et al. |
| 10,167,470 B2 | 1/2019 | Collin et al. |
| 10,647,985 B2 | 5/2020 | Collin et al. |
| 11,279,933 B2 | 3/2022 | Collin et al. |
| 2005/0118625 A1 | 6/2005 | Mounts |
| 2005/0233455 A1 | 10/2005 | Damha et al. |
| 2009/0011040 A1 | 1/2009 | Naash et al. |
| 2009/0269755 A1 | 10/2009 | Aartsma-Rus et al. |
| 2011/0117058 A1 | 5/2011 | Auricchio |
| 2012/0108654 A1 | 5/2012 | Campochiaro |

FOREIGN PATENT DOCUMENTS

| EP | 1619249 | 1/2006 |
| WO | WO 2002024906 | 3/2002 |
| WO | WO 2009121536 | 10/2009 |
| WO | WO 2012168435 | 12/2012 |

OTHER PUBLICATIONS

Uhlmann Current Opinion in Drug Discovery & Development vol. 3, , pp. 203-213 (Year: 2000).*
Aartsma-Rus, et al., "Exonic sequences provide better targets for antisense oligonucleotides than splice site sequences in the modulation of Duchenne muscular dystrophy splicing," Oligonucleotides, 2008, 20:69-77.
Aartsma-Rus, et al., "Guidelines for antisense oligonucleotide design and insight into splice-modulating mechanisms," Mol. Ther., 2008, 548-553.
Alloca, et al., "Novel adeno-associated virus serotypes efficiently transduce murine photoreceptors," J. Virol., 2007, 81:11372-11380.
Baala et al., "Pleiotropic effects of CEP290 (NPHP6) mutations extend to Meckel syndrome", Am. J. Hum. Genet., 2007, 81:170-179.
Bainbridge, et al. "Effect of gene therapy on visual function in Leber's congenital amaurosis," N. Engl. J. Med., 2008, 358:2231-2239.
Baye, "The N-Terminal Region of Centrosomal Protein 290 (CEP290) Restores Vision in a Zebrafish Model of Human Blindness", Human Molecular Genetics, Apr. 2011, vol. 20, No. 8, pp. 1467-1477.
Cideciyan et al., "Centrosomai-Ciliary Gene CEP290/NPHP6 Mutations Result in Blindness with Unexpected Sparing of Photoreceptors and Visual Brain: Implications for Therapy of Leber Congenital Amaurosis", Human Mutation, Nov. 2007, vol. 28, No. 11, pp. 1074-1083.
Cideciyan, et al. "Human gene therapy for RPE65 isomerase deficiency activates the retinoid cycle of vision but with slow rod kinetics", Proc Natl Acad Sci, 2008, vol. 105, 15112-15117.

(Continued)

*Primary Examiner* — Brian Whiteman
(74) *Attorney, Agent, or Firm* — Fish & Richardson P.C.

(57) ABSTRACT

The present invention relates to the fields of medicine and immunology. In particular, it relates to novel antisense oligonucleotides that may be used in the treatment, prevention and/or delay of Leber congenital amaurosis.

23 Claims, 5 Drawing Sheets

Specification includes a Sequence Listing.

(56) References Cited

OTHER PUBLICATIONS

Collin et al., "Antisense oligonucleotide (AON)-based therapy for CEP290-associated LCA." Poster presented at: ARVO Annual Meeting, May 3, 2011, Program No. 3324, Poster No. A572.

Coppieters, et al. "Genetic screening of LCA in Belgium: predominance of CEP290 and identification of potential modifier alleles in AH 11 of CEP290-related phenotypes", Hum Mutat, 2010, 31:E1709-E1766.

Coppieters, et al., "CEP290, a gene with many faces: mutation overview and presentation of CEP290base," Hum. Mutat., 2010, 31:1097-1108.

Dorn and Kippenberger, "Clinical application of CpG-, non-CpG-, and antisense oligodeoxynucleotides as immunomodulators," Curr. Opin. Mol. Ther., 2008, 10(1):10-20.

Egholm, et al., "PNA hybridizes to comlementary oligonucleotides obeying the Watson-Crick hydrogen-bonding rules," Nature, 1993, 365:566-568.

Estrada-Cuzcano, et al. "IQCB1 mutations in patients with leber congenital amaurosis", Invest Ophthalmol Vis Sci, 2011, vol. 52, 834-839.

Franchi et al., "Identification of 4370 expressed sequence tags from a 3'-end-specific cDNA library of human skeletal muscle by DNA sequencing and filter hybridization", Genome Research, 1996, vol. 6.1, pp. 35-42.

Frank, et al., "Mutations of the CEP290 gene encoding a centrosomal protein cause Meckel-Gruber syndrome," Hum. Mutat., 2008, 29:45-52.

Friesen and Darby, "Specific RNA binding proteins constructed from zinc fingers," Nature Structural Biology, 1998, 5:543-546.

Geib and Hertel, "Restoration of full-length SMN promoted by adenoviral vectors expressing RNA antisense oligonucleotides embedded in U7 snRNAs," PLoS One, 2009, e8204.

Gerard et al., "Antisense Oligonucleotide-Mediated Exon Skipping Restores Primary Cilia Assembly in Fibroblasts Harbouring the Common LCA CEP290 C.2991|1655g>A Mutation", Investigative Ophthalmology & Visual Science, Mar. 2012, 1920-1920.

Gerard et al., "AON-Mediated Exon Skipping Restores Ciliation in Fibroblasts Harboring the Common Leber Congenital Amaurosis CEP290 Mutation", American Society of Gene & Cell Therapy, Molecular Therapy-Nucleic Acids, Jun. 26, 2012, vol. 1, e29.

Gorman, et al., "Stable alteration of pre-mRNA splicing patterns by modified U7 small nuclear RNAs," Proc. Natl. Acad. Sci. USA, 1998, 95(9):4929-34.

Govindaraju and Kumar, "Backbone-extended pyrrolidine peptide nucleic acids (bepPNA): design, synthesis and DNA/RNA binding studies," Chem. Commun., 2005, 495-497.

Goyenvalle, et al., "Rescue of dystrophic muscle through U7 snRNA-mediated exon skipping," Science, 2004, 306:1796-1799.

Hammond, et al., "Genetic therapies for RNA mis-splicing diseases," Trends Genet., 2011, 27:196-205.

Hauswirth, et al. "Phase I Trial of Leber Congenital Amaurosis due to Estrada—Mutations by OcularSubretina Injection of Adena-Associated Virus Gene Vector: Short-Term Results," Hum Gene Ther, Oct. 2008, vol. 19, pp. 979-990.

Helou, et al. "Mutation analysis of NPHP6/CEP290 in patients with Joubert syndrome and Senior-Loken syndrome", U Med Genet. 2007, 44:657-663.

Hollander et al., "Mutations in the CEP290 (NPHP6) Gene are a Frequent Cause of Leber Congenital amaurosis," American Journal of Human Genetics, American Society of Human Genetics, Sep. 2006, vol. 79, No. 3, pp. 556-561.

Hollander, et al. "Leber congenital amaurosis: genes, proteins and disease mechanisms," Prog Retin Eye Res, 2008, vol. 27:391-419.

Hollander, et al. "Lighting a candle in the dark: advances in genetics and gene therapy of recessive retinal dystrophies", J Clin Invest, 2010, vol. 120, 3042-3053.

International Search Report in PCT/NL2012/050275 dated Aug. 28, 2012.

International Preliminary Report on Patentability in International Application No. PCT/NL2012/050275, dated Mar. 12, 2014, 9 pages.

Jahns, et al., "Stereochemical bias introduced during RNA synthesis modulates the activity of phosphorothioate siRNAs," Nature Communications, 2015, 6:6317.

Kinali, et al., "Local restoration of dystrophin expression with the morpholino oligomer AVI-4658 in Duchenne muscular dystrophy: a single-clind, placebo-controlled, dose-escalation, proof-of-concept study," Lancet Neurol., 2009, 8:918-928.

Koenekoop, et al. "Genetic testing for retinal dystrophies and dysfunctions: benefits, dilemmas and solutions", Clin Experiment Ophthalmol, 2007, vol. 35, 473-485.

Lebherz, et al., "Novel AAV serotypes for improved ocular gene transfer," J. Gene Med., 2008, 10:375-382.

Li et al., "Gene therapy following subretinal AAV5 vector delivery is not affected by a previous intravitreal AAV5 vector administration in the partner eye," Mol. Vis., 2009, 15:267-275.

Littink, et al. "A novel nonsense mutation in CEP290 induces exon skipping and leads to a relatively mild retinal Phenotype", Invest Ophthalmol Vis Sci, 2010, Vo. 51, 3646-3652.

Maguire, et al. "Age-dependent effects of RPE65 gene therapy for Leber's congenital amaurosis: a phase 1 doseescalation trial", Lancet, 2009, vol. 374, 1597-1605.

Maguire, et al. "Safety and efficacy of gene transfer for Leber's congenital amaurosis," N Engl J Med, 2008, vol. 358, 2240-2248.

Morita, et al., "2'-O, 4'C-Ethylene-bridged nucleic acids (ENA) with nuclease-resistance and high affinity for RNA," Nucleic Acid Res., 2001, Suppl. 1: 241-242.

Nielsen, et al., "Sequence-selective recognition of DNA by strand displacement with a thymine-substituted polyamide," Science, 1991, 254:1497-1500.

Perrault, et al. "Spectrum of NPHP6/CEP290 mutations in Leber congenital amaurosis and delineation of the associated phenotype", Hum Mutat, 2007, vol. 28:416-416.

Schmid and Jelinek, "The Alu family of dispersed repetitive sequences," Science, 1982, 216:1065-1070.

Simonelli, et al., "Gene therapy for Leber's congenital amaurosis is safe and effective through 1.5 years after vector administration," Mol. Ther., 2009, 18:643-650.

Smith, et al., "An increased specificity score matrix for the prediction of SF2/ASF-specific exonic splicing enhancers," Hum. Mol. Genet., 2006, 15:2490-2508.

Stone "Leber congenital amaurosis—a model for efficient genetic testing of heterogeneous disorders: LXIV Edward Jackson Memorial Lecture", Am J Ophthalmol, 2007, vol. 144, 791-811.

Suter, et al., Double-target antisense U7 snRNAs promote efficient skipping of an aberrant exon in three human beta-thalassemic mutations, hum. Mol. Genet., 1999, 8(13):2415-23.

Valente, et al. "Mutations in CEP290, which encodes a centrosomal protein, cause pleiotropic forms of Joubert syndrome", Nat Genet, 2006, vol. 38, 623-625.

Van Deutekom, et al., "Local dystrophin restoration with antisense oligonucleotide PRO051," N. Engl. J. Med., 2007, N. Engl. J. Med., 357:2677-2686.

Vandenberghe, et al., "Dosage thresholds for AAV2 and AAV8 photoreceptor gene therapy in monkey," Sci. Transl. Med., 2011, 3:88ra54.

* cited by examiner

A  Wild-type CEP290

B  LCA mutant CEP290

C  LCA mutant CEP290 + AON

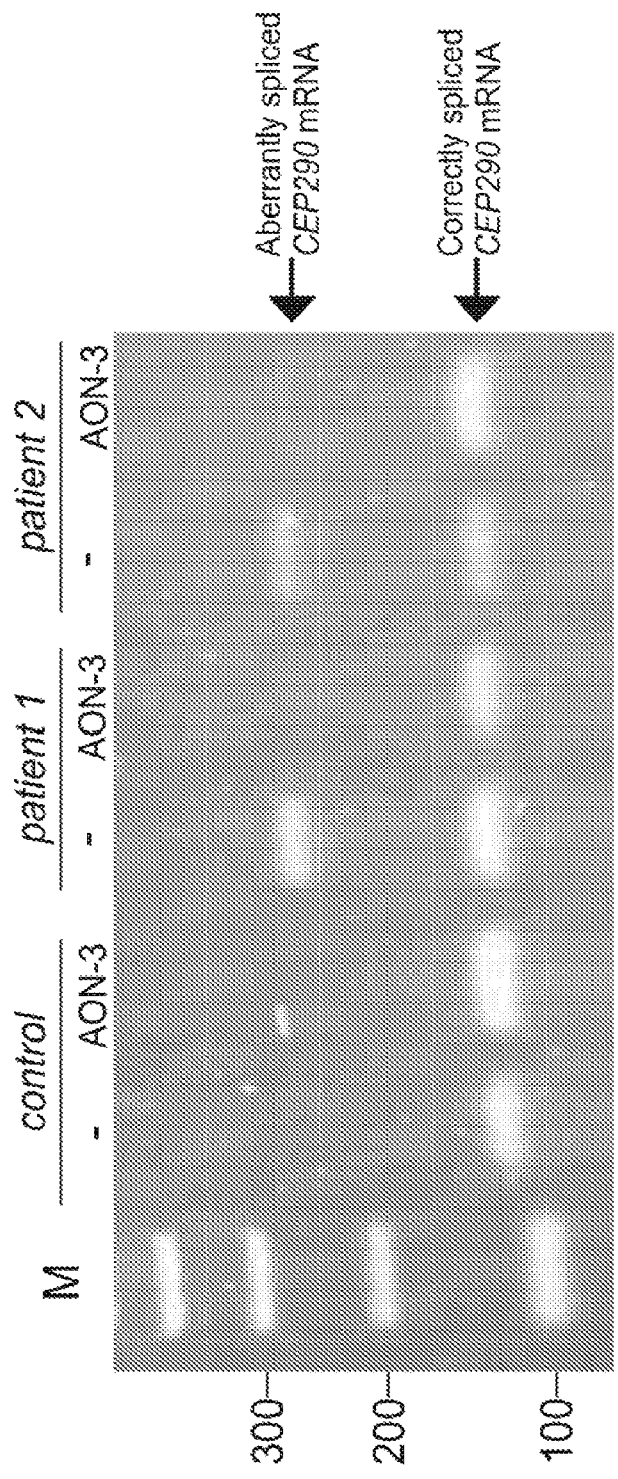

SEQUENCE LISTING

<160> NUMBER OF SEQ ID NOS: 21

<210> SEQ ID NO 1
<211> LENGTH: 93203
<212> TYPE: DNA
<213> ORGANISM: Homo sapiens

```
<220> FEATURE:
<221> NAME/KEY: 5'UTR
<222> LOCATION: (1)..(909)
<223> OTHER INFORMATION: Intron from 318 to 882
<220> FEATURE:
<221> NAME/KEY: exon
<222> LOCATION: (910)..(1011)
<220> FEATURE:
<221> NAME/KEY: Intron
<222> LOCATION: (1012)..(1183)
<220> FEATURE:
<221> NAME/KEY: exon
<222> LOCATION: (1184)..(1261)
<220> FEATURE:
<221> NAME/KEY: Intron
<222> LOCATION: (1262)..(2652)
<220> FEATURE:
<221> NAME/KEY: exon
<222> LOCATION: (2653)..(2722)
<220> FEATURE:
<221> NAME/KEY: Intron
<222> LOCATION: (2723)..(3025)
<220> FEATURE:
<221> NAME/KEY: exon
<222> LOCATION: (3026)..(3072)
<220> FEATURE:
<221> NAME/KEY: Intron
<222> LOCATION: (3073)..(5430)
<220> FEATURE:
<221> NAME/KEY: exon
<222> LOCATION: (5431)..(5574)
<220> FEATURE:
<221> NAME/KEY: Intron
<222> LOCATION: (5575)..(10998)
<220> FEATURE:
<221> NAME/KEY: exon
<222> LOCATION: (10999)..(11052)
<220> FEATURE:
<221> NAME/KEY: Intron
<222> LOCATION: (11053)..(11651)
<220> FEATURE:
<221> NAME/KEY: exon
<222> LOCATION: (11652)..(11672)
<220> FEATURE:
<221> NAME/KEY: Intron
<222> LOCATION: (11673)..(11796)
<220> FEATURE:
<221> NAME/KEY: exon
<222> LOCATION: (11797)..(11949)
<220> FEATURE:
<221> NAME/KEY: Intron
<222> LOCATION: (11950)..(12340)
<220> FEATURE:
<221> NAME/KEY: exon
<222> LOCATION: (12341)..(12523)
<220> FEATURE:
<221> NAME/KEY: Intron
<222> LOCATION: (12524)..(13181)
<220> FEATURE:
<221> NAME/KEY: exon
<222> LOCATION: (13182)..(13271)
<220> FEATURE:
<221> NAME/KEY: Intron
<222> LOCATION: (13272)..(15778)
<220> FEATURE:
<221> NAME/KEY: exon
<222> LOCATION: (15779)..(15901)
<220> FEATURE:
<221> NAME/KEY: Intron
<222> LOCATION: (15902)..(16847)
<220> FEATURE:
<221> NAME/KEY: exon
<222> LOCATION: (16848)..(16971)
<220> FEATURE:
<221> NAME/KEY: Intron
<222> LOCATION: (16972)..(21050)
<220> FEATURE:
<221> NAME/KEY: exon
<222> LOCATION: (21051)..(21220)
```

```
<220> FEATURE:
<221> NAME/KEY: Intron
<222> LOCATION: (21221)..(21940)
<220> FEATURE:
<221> NAME/KEY: exon
<222> LOCATION: (21941)..(22103)
<220> FEATURE:
<221> NAME/KEY: Intron
<222> LOCATION: (22104)..(23473)
<220> FEATURE:
<221> NAME/KEY: exon
<222> LOCATION: (23474)..(23574)
<220> FEATURE:
<221> NAME/KEY: Intron
<222> LOCATION: (23575)..(23646)
<220> FEATURE:
<221> NAME/KEY: exon
<222> LOCATION: (23647)..(23734)
<220> FEATURE:
<221> NAME/KEY: Intron
<222> LOCATION: (23735)..(25071)
<220> FEATURE:
<221> NAME/KEY: exon
<222> LOCATION: (25072)..(25184)
<220> FEATURE:
<221> NAME/KEY: Intron
<222> LOCATION: (25185)..(27034)
<220> FEATURE:
<221> NAME/KEY: exon
<222> LOCATION: (27035)..(27119)
<220> FEATURE:
<221> NAME/KEY: Intron
<222> LOCATION: (27120)..(27654)
<220> FEATURE:
<221> NAME/KEY: exon
<222> LOCATION: (27655)..(27797)
<220> FEATURE:
<221> NAME/KEY: Intron
<222> LOCATION: (27798)..(30358)
<220> FEATURE:
<221> NAME/KEY: exon
<222> LOCATION: (30359)..(30523)
<220> FEATURE:
<221> NAME/KEY: Intron
<222> LOCATION: (30524)..(30865)
<220> FEATURE:
<221> NAME/KEY: exon
<222> LOCATION: (30866)..(31015)
<220> FEATURE:
<221> NAME/KEY: Intron
<222> LOCATION: (31016)..(33035)
<220> FEATURE:
<221> NAME/KEY: exon
<222> LOCATION: (33036)..(33151)
<220> FEATURE:
<221> NAME/KEY: Intron
<222> LOCATION: (33152)..(35118)
<220> FEATURE:
<221> NAME/KEY: exon
<222> LOCATION: (35119)..(35221)
<220> FEATURE:
<221> NAME/KEY: Intron
<222> LOCATION: (35222)..(35311)
<220> FEATURE:
<221> NAME/KEY: exon
<222> LOCATION: (35312)..(35542)
<220> FEATURE:
<221> NAME/KEY: Intron
<222> LOCATION: (35543)..(39205)
<220> FEATURE:
<221> NAME/KEY: exon
<222> LOCATION: (39206)..(39379)
<220> FEATURE:
<221> NAME/KEY: Intron
<222> LOCATION: (39380)..(45217)
<223> OTHER INFORMATION: Aberrant exon included in mutant CEP290 mRNA
      position 40902-41209 mutated nucleotide A>G in LCA patients at
      position 41034
<220> FEATURE:
```

```
<221> NAME/KEY: exon
<222> LOCATION: (45218)..(45329)
<220> FEATURE:
<221> NAME/KEY: Intron
<222> LOCATION: (45330)..(48241)
<220> FEATURE:
<221> NAME/KEY: exon
<222> LOCATION: (48242)..(48447)
<220> FEATURE:
<221> NAME/KEY: Intron
<222> LOCATION: (48448)..(49384)
<220> FEATURE:
<221> NAME/KEY: exon
<222> LOCATION: (49385)..(49536)
<220> FEATURE:
<221> NAME/KEY: Intron
<222> LOCATION: (49537)..(51377)
<220> FEATURE:
<221> NAME/KEY: exon
<222> LOCATION: (51378)..(51489)
<220> FEATURE:
<221> NAME/KEY: Intron
<222> LOCATION: (51490)..(52729)
<220> FEATURE:
<221> NAME/KEY: exon
<222> LOCATION: (52730)..(53185)
<220> FEATURE:
<221> NAME/KEY: Intron
<222> LOCATION: (53186)..(54272)
<220> FEATURE:
<221> NAME/KEY: exon
<222> LOCATION: (54273)..(54437)
<220> FEATURE:
<221> NAME/KEY: Intron
<222> LOCATION: (54438)..(55718)
<220> FEATURE:
<221> NAME/KEY: exon
<222> LOCATION: (55719)..(55826)
<220> FEATURE:
<221> NAME/KEY: Intron
<222> LOCATION: (55827)..(56043)
<220> FEATURE:
<221> NAME/KEY: exon
<222> LOCATION: (56044)..(56178)
<220> FEATURE:
<221> NAME/KEY: Intron
<222> LOCATION: (56179)..(57364)
<220> FEATURE:
<221> NAME/KEY: exon
<222> LOCATION: (57365)..(57631)
<220> FEATURE:
<221> NAME/KEY: Intron
<222> LOCATION: (57632)..(58262)
<220> FEATURE:
<221> NAME/KEY: exon
<222> LOCATION: (58263)..(58370)
<220> FEATURE:
<221> NAME/KEY: Intron
<222> LOCATION: (58371)..(58986)
<220> FEATURE:
<221> NAME/KEY: exon
<222> LOCATION: (58987)..(59186)
<220> FEATURE:
<221> NAME/KEY: Intron
<222> LOCATION: (59187)..(61821)
<220> FEATURE:
<221> NAME/KEY: exon
<222> LOCATION: (61822)..(62035)
<220> FEATURE:
<221> NAME/KEY: Intron
<222> LOCATION: (62036)..(62987)
<220> FEATURE:
<221> NAME/KEY: exon
<222> LOCATION: (62988)..(63125)
<220> FEATURE:
<221> NAME/KEY: Intron
<222> LOCATION: (63126)..(64298)
<220> FEATURE:
<221> NAME/KEY: exon
```

```
<222> LOCATION: (64299)..(64520)
<220> FEATURE:
<221> NAME/KEY: Intron
<222> LOCATION: (64521)..(64872)
<220> FEATURE:
<221> NAME/KEY: exon
<222> LOCATION: (64873)..(64995)
<220> FEATURE:
<221> NAME/KEY: Intron
<222> LOCATION: (64996)..(70290)
<220> FEATURE:
<221> NAME/KEY: exon
<222> LOCATION: (70291)..(70436)
<220> FEATURE:
<221> NAME/KEY: Intron
<222> LOCATION: (70437)..(70767)
<220> FEATURE:
<221> NAME/KEY: exon
<222> LOCATION: (70768)..(70923)
<220> FEATURE:
<221> NAME/KEY: Intron
<222> LOCATION: (70924)..(73571)
<220> FEATURE:
<221> NAME/KEY: exon
<222> LOCATION: (73572)..(73695)
<220> FEATURE:
<221> NAME/KEY: Intron
<222> LOCATION: (73696)..(78101)
<220> FEATURE:
<221> NAME/KEY: exon
<222> LOCATION: (78102)..(78236)
<220> FEATURE:
<221> NAME/KEY: Intron
<222> LOCATION: (78237)..(79438)
<220> FEATURE:
<221> NAME/KEY: exon
<222> LOCATION: (79439)..(79525)
<220> FEATURE:
<221> NAME/KEY: Intron
<222> LOCATION: (79526)..(81222)
<220> FEATURE:
<221> NAME/KEY: exon
<222> LOCATION: (81223)..(81387)
<220> FEATURE:
<221> NAME/KEY: Intron
<222> LOCATION: (81388)..(82196)
<220> FEATURE:
<221> NAME/KEY: exon
<222> LOCATION: (82197)..(82319)
<220> FEATURE:
<221> NAME/KEY: Intron
<222> LOCATION: (82320)..(83196)
<220> FEATURE:
<221> NAME/KEY: exon
<222> LOCATION: (83197)..(83369)
<220> FEATURE:
<221> NAME/KEY: Intron
<222> LOCATION: (83370)..(86499)
<220> FEATURE:
<221> NAME/KEY: exon
<222> LOCATION: (86500)..(86641)
<220> FEATURE:
<221> NAME/KEY: Intron
<222> LOCATION: (86642)..(87803)
<220> FEATURE:
<221> NAME/KEY: exon
<222> LOCATION: (87804)..(87877)
<220> FEATURE:
<221> NAME/KEY: Intron
<222> LOCATION: (87878)..(88470)
<220> FEATURE:
<221> NAME/KEY: exon
<222> LOCATION: (88471)..(88565)
<220> FEATURE:
<221> NAME/KEY: Intron
<222> LOCATION: (88566)..(91783)
<220> FEATURE:
<221> NAME/KEY: exon
<222> LOCATION: (91784)..(91863)
```

```
<220> FEATURE:
<221> NAME/KEY: Intron
<222> LOCATION: (91864)..(92802)
<220> FEATURE:
<221> NAME/KEY: exon
<222> LOCATION: (92803)..(93033)
<220> FEATURE:
<221> NAME/KEY: 3'UTR
<222> LOCATION: (93034)..(93203)

<400> SEQUENCE: 1
```

| | |
|---|---|
| atttgaagtc ctcgttccac gccttctcat catcctgaac accgagctct gggactccgg | 60 |
| cggagaatct aaacgtaaag catcacccac ggtcgtgaac tgtaggctct cctggcatcc | 120 |
| gggatcttat tctggccttg gcggagttgg ggatggtgtc gcctagcagc cgctgccgct | 180 |
| ttggcttgct cgggaccatt tggctggacc cagagtccgc gtggaaccgc gatagggatc | 240 |
| tgtcagggcc cgcggccggg tccagcttgg tggttgcggt agtgagaggc ctccgctggt | 300 |
| tgccaggctt ggtctaggtg ggtggatcct tgtaagcagg attagcgagt cactccacgc | 360 |
| tcaggttctt tagcctgagg gcccgtgtgc cacagcatag ctaccccgcc cttccagcct | 420 |
| cgggtcccta atactgcctt gcttcggttc cagtttccgc cgcacaactt cactcattcc | 480 |
| aaatgttaat ttctgcgttt tttttcagcc ccaattctgt ttctccaaat cagggatgat | 540 |
| tgtcggcctt ccacagaccc tcgcgcttgc caggattagg gtgttcgcgc gcattgtggg | 600 |
| tagggggtgtg gaggaaggga tccagaaatc ttaagtatta acttagatta gtgttagcaa | 660 |
| ggaagccgtc acattttatt tagccgggac actctgacag tttgtgccga ctgctatttt | 720 |
| tgatcaaggc tattttgccc acttgtctat tttgtggccc aattgtctgt tttgctaaca | 780 |
| tcagaaagtt ataatgaaat aatctgcaaa aaatgtaagg tgctagaaaa ccaataatac | 840 |
| tgtgtacctt gaaaatgcta atatacacct gttttgttac agaggtggag cacagtgaaa | 900 |

```
gaattcaag atg cca cct aat ata aac tgg aaa gaa ata atg aaa gtt gac      951
          Met Pro Pro Asn Ile Asn Trp Lys Glu Ile Met Lys Val Asp
            1               5                  10 cca gat gac ctg ccc cgt caa gaa gaa ctg gca gat aat tta ttg att        999
Pro Asp Asp Leu Pro Arg Gln Glu Glu Leu Ala Asp Asn Leu Leu Ile
 15              20                  25                  30 tcc tta tcc aag gtgcttaatt ggtcaataat aatagatata tacattaact           1051
Ser Leu Ser Lys
```

| | |
|---|---|
| tatgattaat ttattaataa aatatgaatt tatttttttc agggacaact ataattgtca | 1111 |
| caatctggaa gtgttcttat attttgcttg aaggttataa aatataaaac agttgctttt | 1171 |

```
ctgtttactt ag gtg gaa gta aat gag cta aaa agt gaa aag caa gaa aat     1222
              Val Glu Val Asn Glu Leu Lys Ser Glu Lys Gln Glu Asn
               35                  40                  45 gtg ata cac ctt ttc aga att act cag tca cta atg aag gtttgtatgt        1271
Val Ile His Leu Phe Arg Ile Thr Gln Ser Leu Met Lys
 50                  55                  60
```

| | |
|---|---|
| agtaggtttt aactataggt ttggctatta gtggaactat aaaaatctgt tcttatataa | 1331 |
| ggtaatcttt gtgaaaatac ctggtaatat ctacatcacc actaaaaaat gcaatatatt | 1391 |
| taaatgtgaa ttaagtattt tagtgtataa aacattgcta gtttctactt aaagtttcta | 1451 |
| aaagggtgtg taggggaaat agaatgagta tgttgaaaag taacataagg aaatatatct | 1511 |
| tgaggtccaa atgacaaatg cagacaatga ctgctatagg gatttgttaa gaggggaaat | 1571 |
| gatttaagag atgtcagaag acttcacaaa ggatcaatac tgaggagtag tgttagataa | 1631 |
| gtggaaggca atgcagtggt aagatagtaa gggaattcta gagctgttgg ttaccataaa | 1691 |

```
taaatactga gaacaggaaa tatgtttatt ctttatattt gaggaaacaa ggtgcagcaa   1751
gtttgtagca gactgtagag aaaacaaatc ttgggtaagt actttgagat aggttgttga   1811
gggccttaaa ggtgtatttt atgctatcag caattgagaa ggcagtaaag gttttcgaaa   1871
cacaattgat aggtacaaaa atacacctta agaaggcaaa actgagtata ttatgtagga   1931
caaactgaag gaaattggag ctttgtagac atcacattat agcggagttt aaacctgaaa   1991
ttatggatta gaataatagc aattggaaca gaaaaaaagt agtggaaaga cattacaaag   2051
ggagatgttg cattactgga tataagactt gaggacttga ggtaaaaagg agaatcaaaa   2111
atgtttcatg ctattaaaaa tctagaaatt gtagtcttaa gtaagaaaat tgcctggcat   2171
ggtggctcac gtctgtaatc ccagcacttt gggaggccaa ggcaggagga ttgcttgagc   2231
ctgggagttc aagactagcc tgataatat agtgagtcct tgcctgtacg aaaaaatttg    2291
ccgagcatga tggcacacca agcatgatgg cacgccaagc atgatggcat gcacctgtag   2351
tcccagctac tcaggagact gagatgggaa gattgcttga gcccaggagg caggaggttg   2411
cagtgagctg agattgtgcc actgcactcc agcctgggtg acaaagtgag gccctatctc   2471
aaaagcaaaa aaaacaaaaa caaaaaccaa aaactattta ttcagcaaat atttactgaa   2531
cgtctccatg tgccagccat tgctggcact aaggatcata caaataaaaa cagaattttt   2591
attttcagtg cttacattcc agtataaagg catattgaaa taaccttttt ttaatgttta   2651
g atg aaa gct caa gaa gtg gag ctg gct ttg gaa gaa gta gaa aaa gct   2700
  Met Lys Ala Gln Glu Val Glu Leu Ala Leu Glu Glu Val Glu Lys Ala
                65                  70                  75
gga gaa gaa caa gca aaa ttt g gtaagcacct tggaaaaagt ttattatggt       2752
Gly Glu Glu Gln Ala Lys Phe
            80
attaaataat gaattccatt tgttcattaa actgtagaaa attaaattat attctataaa   2812
atatatatat tcagtttatt tttaatatat aacatttaat aataaatatt tctagactcc   2872
tattttatgg atctgccata taatacttt tgttaccta taatcatgat ggactctttt    2932
aaaagaatta atttttgttat tgaaatttat ttaaaagttt gttttgtggt aactaatcaa   2992
ttaaaacgtt tttcttttt tttaaaaaaa tag aa  aat caa tta aaa act aaa    3045
                                      Glu Asn Gln Leu Lys Thr Lys
                                              85              90
gta atg aaa ctg gaa aat gaa ctg gag gtatgtcttt ttgtattccc            3092
Val Met Lys Leu Glu Asn Glu Leu Glu
            95
taggatgtaa ttgtcattaa ttttattttg aattgttttc aaatttttaaa attattgttg   3152
gctggaaaaa ttataaggat gattgtaatc atggttattt gtttattctg tatatgttct   3212
acatgcctat tatgtgcctt atatagtact aaggactgag catatggttg tgaacaaaat   3272
aagaagttaa ctgctggatg gagcttatag tcttgggaaa tatacagaaa gattactagt   3332
aactgaggtg gagggtgggt ggggatttga ggaatagtga cgaaagggtg ttatagaagt   3392
aattttttgac aaagctgaag gctaaaatat gaatgtattg ttgaagaaca aaatacattg  3452
agattcctga gaaggtagga atgtgataca aatggatcag cctttgaaag gaggaatacc   3512
cttttccttt gtgttaggag aggaggatga gtggatgagc gtgggaagag tggatgtgta   3572
tagaggcttt tatgtttgta ggcataatgc ttggaagttg aggggttggt gatgacatct   3632
tctgttaaaa agagtgggaa atggtgtggt cacattttaa ggaaattagg taaaatttga   3692
aatatattgg agacaggact ggagagttgg ggatctggag tcagacagat ttgagttcta   3752
gtcctgattc ttctactcgt taactctctg aacttggatg acctattgtt tttgattgta   3812
```

```
tatccagctc ctgggaaaat gccaagcact ttcaataaat actaaatgaa ttatggagtt    3872
ggatcagttc tgtgttagtg tttagctagg tagctgctgt agaatagaag ggtagcacag    3932
ttgaagatat tggtaggaaa gtggttgaag tgatgattat gaagtcttaa ctgaatagat    3992
aaaatcaaga ttggggttgg gtgggcagaa gggtagggat atggagggag aagatgaggg    4052
gttagagtgt cctgtgaggt cgaaggacag gcatagtggg aataattgaa agaatgttct    4112
ggttggacaa ggatctgatg tgggtgtggg agtgagagac tatagtgaat tcaagaaaaa    4172
aatagactag aacaaaagtt atgtggagat tgcttagtgg gcatttgata gacatctgtg    4232
ggccacatgc ttaaattccc agtgcatttt gcggagttac tggaaggttg gtggcttgtt    4292
tctaccatga gtaggtaaag atggagagca ggatattttg tgagaaagca gctgaagttt    4352
ctataggatg atggaggaat gataggaatg atcacctgaa gttgcagggt ggggtaaacc    4412
tagaagcacc aacaccttct tctgaccctc atgtatttgg aatctgaaag aatgagcacc    4472
ttccaattga aagagttcca agggcattag tatactaaag gatccaaatt gcagctaagc    4532
caaggagatg gaaaggagga ttcagtaaag aatctgagga tgtgaaatat taatttatct    4592
tggaagagaa ttttagagag cacaatgaaa tgcttttttgg aggagagaaa gagtaagaac    4652
aatttggtta aggtagagga ataacagaac tataaggtga agaaatgaat gtgagacaca    4712
ttagatgacc aaatgatttg atgttcttgg ccatgacctg aattaacaag actgtgaggt    4772
aaaatggatt taatcggcta caaatcttaa gataaccaaa acctgagctg tttaatatgg    4832
tagcactagc actaaccact tgtagctatt tatatttaca ttggttaaaa ttaaaatgaa    4892
aaatttagtt cttcagttgc actagccaca cttcaaatgc ccgaacatag ctacatgtag    4952
cgagtggcta ttgaactgga cagcactgac agcatgtcca ttatgctaga aagtcctatg    5012
ggacagcact ggtctaaaca gtgcatggta tgagagaaag ggcaggttaa ggcactcagc    5072
ttcactgact ggggtggaga ttctgatggt ttgtactcag gttccagatc cctgaggctc    5132
aggaaccttt gcagtttagt ctggttacct gtggcccagt ggttacaaca gaatgattaa    5192
cagtcaattc tttgcatctc tgggtggctc aggaaaaatt taaggagtta ttagctgtga    5252 actaaccta agtaagttaa attaaaaaaa aaaagttct taagctaata tgattttaaa    5312
tatctgcact gaagtataat gcaaatttaa attcagcata attatttgct tgttgttgac    5372
tcatttgaac ctcaaaatat aatgggatta atttatactt tgggtttatt actttaag    5430 atg gct cag cag tct gca ggt gga cga gat act cgg ttt tta cgt aat    5478
Met Ala Gln Gln Ser Ala Gly Gly Arg Asp Thr Arg Phe Leu Arg Asn
100             105                 110                 115 gaa att tgc caa ctt gaa aaa caa tta gaa caa aaa gat aga gaa ttg    5526
Glu Ile Cys Gln Leu Glu Lys Gln Leu Glu Gln Lys Asp Arg Glu Leu
            120                 125                 130 gag gac atg gaa aag gag ttg gag aaa gag aag aaa gtt aat gag caa    5574
Glu Asp Met Glu Lys Glu Leu Glu Lys Glu Lys Lys Val Asn Glu Gln
        135                 140                 145 gtaaagcact ttttttttcc atgaatcttc actgttcaag ttacctggct ttttattatt    5634
attggtaaca atatcaattt ttatattgta tgttatattt gaaaaatgat gtacacttat    5694
ctctaaggtt ttatatcact gttcattttg tcatcaccaa ttttaaaata taatggtact    5754
tctagtgaat atgacttgaa gattaattct ttatatttgg aagtacattt ttctcaggac    5814
atcaaacttg ttacctaaaa ttaatgcttt tgtctggaag attggtatca agtaactaat    5874
agattttcat aaagaagtga tctttctagt gccatagttt attttgggta aaagttatat    5934
```

```
ttgttcattt caatgtattt atatgattag tagattcgca aatgaatctt tcgatatatt      5994
caataatggt taattaaata tcttgttttt ggttgtacct tattttatgt gagatatata      6054
tatatatgta tagtttttga aaagttgtgt tcatgtcagc agtttataaa tcacatattt      6114
aaaataacat tttaatgca tagtttttat tacctcgtta ttccttgtta taaactaata      6174
attcttgcag tgttcacttg aatttagttt taggaaaaaa gttttttgca gatcaacttg      6234
tatttcctgg aagaaaattt cctatttac ctcagcttcc tatttaatgt attatttatt      6294
tatttactta acatttattt gttttttatt tcacctgaac tgttagtaaa cttagtaaaa      6354
tttggtgcct acatgtggta actgtcctgt cccttatact cagaaacgtt ttccacctt      6414 gtgtcccttta ggtcattgtt gtgttatatt ccatttattt tattttgtcc attgttctct     6474
cagaaattga gggtcataca ttttaagaaa acaatgatat gctatttaag agaatgtatc      6534
ataaattgat ttgtaaggaa aagtatcccc attcttcatg tatgtatttt actctaaaat      6594
gttgaagaat catatagaag ttagctatga aaacaatgtg gtagagaaag tatggatcga      6654
tgccacttaa atgttaggaa gaagctctta gagcattatc tgtttagcta actgcaaaac      6714
atagcagaca tgtggatttt ttaatagtca tcaaggatct aacttataat atacactggt      6774
agaattgctt aggggggatgt ctgtggtttt ctggactttt gttcttctat atagacctgt    6834
atcagttgac ttatcattca taccacacac ccttagctaa tcagaactac cttgtccatt      6894
tatatcttag actattgtct tttttcatag tcacacacag agaaaacttg aatatatggc      6954
ctgtgttcct ttttggctgc tcaattcctt gagatgaaat atgggtatgg gttgctttgg      7014
caattacttc tttgccgtta accagtcatt cagttttatt gagtctttac agcataccag      7074
aggctgctag ttactagtga tatagtgggc aactatgttc tggttctcaa gaatattcat      7134
agtcaataat aagcataaca tagtgataat atgatactta gggagataca taaggtcata     7194
ttctggcata ctctggagag agataccgta atcagccttg aggtgcagga tgtgatctgt     7254
aaactgagac ctgaagtata gttagactgg taagaggaat gaggatatat atggtggtta     7314
ataaaagaac attctgggta gaagatatag catttgctaa gacctagagg taagagatgt     7374
tatggagtat ttaggaaact acagttattc attttgactg aaatataagt gaaaatagct     7434
ttcatagagt ccttactatg tgccaggcac ttcatatgca ttaattcatt attgcttatt      7494
tgatacttgt catatgagat agttgtcatt tctgccatga tacagatgaa gaatggaga      7554 cacagaaaga gtaattgccc atggttgcac agcttataaa tggtaaaggt aggatttgaa     7614
aacagtctta ctcaagagtc tgtgctatct tgccttccca gttttatttt ttatgatcct      7674
ctggagagat aagcaagggc cagttcctaa tgaatttggt tcttttcctg aaaggagcca     7734
gtgaagagtt ttgagcacag gatatcatga tcagatctat actttaaaag tttactgtac     7794
tttgtagaga gtggattgaa aagggccaag actagtaagg aaacatttgt gttaattcag     7854
ggaagtgcta atgatggcat ttgcctgaga aagacaagtg tgagagaagt agatgtaatt     7914
ggatgtggtg aatgtaattg gttgttggag gagagggagg atggagagtc tgcctaattt    7974
tgtgggttgg gccactaaat aggtagatag tgccattcat taaggaggaa cacaagagga    8034
atttggaaag cttgagatta tttcagtttt gtagatgttg agtttgaggt tcttctgggc    8094
atattcaaaa agggtatctg tggatatgga attcacaaga gaccctgtac agatgatgag   8154
gatttatgaa tcatcaatgt agacattatt gaagccagag aagtgattgt aaggcacgtc   8214
tctgagaaat gtctaataaa gcaatgaaat aggaagagtc cttcaaggaa aagctcaaga   8274
aaggagaaac agagtgtgat gtttgagaag acaagggaaa aaaacattaa tagcattaaa  8334
```

```
tgctttagca ttaagttctt ggcttctctt cttgtaaaaa tttcccaatt cagaacacag    8394
tgggattatt aactttcaat tgataataat aatgataggc aaacttctaa aatttgtatt    8454
gtagtttgca ttttattata aactttcttt aaatttttat tttgaaaaat gtcatatctt    8514
cataaagatt gtaagaaaca cactgttggt gttaatgtaa attagttcaa ccattgtggg    8574
agacagtgtg gcaattcctc gaagatctag aagcagaaat accacttgac ccagcaatcc    8634
cattactggg tatataccca aaagaatata atcattttc ttataaagat acttgcacac    8694
atatgttcat tgcagcacta ttcacaatag caaagacatg gaatcaaccc aaatgctcat    8754
caatgataga ctggataatg aaaatgtgga acatatacat catagaatac tatgcagcca    8814
tcaaaagaga atgagaggtc aagcgtggtg actcatgcct acagtcccag cactttggga    8874
ggccgaggca ggcagatcac ttgaggtcag gagttcaaga ccagcctggc cagtatggtg    8934 aaacccatc tctacaaaaa caaaacaaaa caaacaaaaa ttaactggtc atggtactgt    8994
atgcctgcag tcccagctac ttgggaggct gaggcaggag aatgacttga acccagaagg    9054
cagaggttgc agtgagctga gatcgcacca ctggactcta gccttagcaa caaaactaga    9114
gtttgtctca aaaaaaaaaa aaaaaaaaaa ccggaacaag atcatgtcct ttgcagggac    9174
atgggatgga ggtggaagcc attatcctca gcaaactcac acaggaacag aaaaccaaac    9234
actgcatgtt ctcacttata agtgggagct gaacaatgag aacacatgga cacatggtgg    9294
ggaacaacac acactgggac ccgtcaaggg gtcggggtgg gagaacatca ggaagaatag    9354
ctaatggatg ctgggcttaa tatctaggtt atgggttgat ctgtgcagca agccaccatt    9414
gtacacattt acctaagtaa caaacctgca catcttacac atgtacccca gaacttaaaa    9474
gttgatggga aaaagaaaaa caataaccac ccacataccc ttcatataga ttcaccagtt    9534
cttaatgttg tgccaacttt gctttatctt tttgtcagta ttttacaca cacatgtatt    9594 tctctgtctc ttgtttgttc aatcacattt tttgctgagt catttaagag ctaattgcag    9654
atatgatact ttgcacttaa atatttcagc ttgtctgttt gaaaagaaa gatgttctcc    9714 tacaatgaac acaatataat tgtcatgctc aggaatttta atattgattc aacaccatta    9774
tctagtccat aatgagattt cttctaatgg cccaataata tccttcagtc tccccacctc    9834
caatatccaa agttctgtca aggatcacat actacatttg gttctttatt atagactttt    9894
taaatatcgt tgtataccat tgtgattcta tcgtctcctt taataaagag gagaaccaga    9954
aaaatgaaag gtcataagag gaatgaggtt tggagaatag gtgaaaaaag gcatcataat   10014
gtttataata atgtttgcct gttcagagaa acaagaatca cagataaagt cacttatatg   10074
tagataagag aatgctgtat tacttttttgc tattctattc actgatcatt tttctaagaa   10134
ctctgtatgc ttcttgttta actcttatgt cagcatgtat gagaaaactg agttaaagag   10194
atgttaagta actcattcat gctttactag aaattggttg atgagggaca taaacctagg   10254
ccggtgtgat tttagattgc ttcttttaac cattgtgttg tattgcctta tatttctaag   10314
taatttatgt tcactgagag caaataatag tctagctatg acttagaaaa gtaaaataaa   10374
gatgttgggc agaaaaccat tttattaggg gttttttttgg aggagcagat taatttgttt   10434
ctgtattctt tggttagttt gtgtgtgtgt tcttttaat tctttaaaat gaaactgttt   10494
aatccttaaa tccttaagtt ttgaaaattt tggcctatta tttatgtgtt aggttgatat   10554
taaatcctta atagctttaa cattttctac tttgttagag aggatttaaa atttaagtag   10614
ataagctgaa tatctggctt tatattaaat tactgctgat ggccaggcac agtggctcat   10674
```

```
gtctgaaatc ctagcacttt gggaggttga ggcagatgga tcacttgagg ccaggagttc    10734
aagaccagcc tggctaacac agtgaaaccc cgtctctact aaaaatacaa aaattagcca    10794
gttatggtaa tgcatgccag taattccagc tactcggtag gctgaggtgg gagaattgct    10854
tgaaccggga ggcagaggtt gcagtgagcc gagatcgcac cactgtactc cagcctaggc    10914
gacaaagact ttgtctcaaa aaaaaaaaa attactgctg aattttatct tcttcttatt    10974
tatttttttt tttactatt ttag ttg gct ctt cga aat gag gag gca gaa         11025
                         Leu Ala Leu Arg Asn Glu Glu Ala Glu
                                    150                 155 aat gaa aac agc aaa tta aga aga gag gtaaaaaatt ttagtagttg             11072
Asn Glu Asn Ser Lys Leu Arg Arg Glu
        160                 165 tggtggttca acaaaggtac ttattaaaat aagtacctaa gtttacataa atttatattt    11132
taaccaggac tggagtcttc taagtaactg atgttttcag actgatttta tggtatgact    11192
ttgtctcagg gaaatagaaa acaaagcaaa atgtgaggcc attaagtatt acattcatct    11252
caggtctatg cgggtaaatc ttttttgtt gttttataag ccattctttg ctagttttct    11312
aattgaatag atgactggat ttctattctt atttctctta cccagaatcc tttaaaattt    11372
tttgttactt gtggaatctt ataaattctg attatcattt ggttctactg agccaaataa    11432
tgtttgtaca ttgtttattc tgatagaagt tcttaagttt ctaacataat gaaatatta    11492 tttgttttgg tagataatta gtattctttc tttggttatt caagataata tgcatcattt    11552
tcccaaaatt ttttttgtttt ctttagtttc tgattattat ttttaattat gtattacctt   11612
tctcatttct aattaccgtt ttcctgtcct tttctgtag aac aaa cgt cta aag        11666
                                              Asn Lys Arg Leu Lys
                                                              170 aaa aag gtgaggcttt aagtgtggtg aaatcttggg aatttaaaat atgttgtgag       11722
Lys Lys agcactattt agaggatatg atttttgttat tctgaatagt tttgtaattg aatgttgtgt    11782
ttggttacct tcag aat gaa caa ctt tgt cag gat att att gac tac cag       11832
                 Asn Glu Gln Leu Cys Gln Asp Ile Ile Asp Tyr Gln
                            175                     180 aaa caa ata gat tca cag aaa gaa aca ctt tta tca aga aga ggg gaa       11880
Lys Gln Ile Asp Ser Gln Lys Glu Thr Leu Leu Ser Arg Arg Gly Glu
185                 190                 195                 200 gac agt gac tac cga tca cag ttg tct aaa aaa aac tat gag ctt atc       11928
Asp Ser Asp Tyr Arg Ser Gln Leu Ser Lys Lys Asn Tyr Glu Leu Ile
                205                 210                 215 caa tat ctt gat gaa att cag gtaaaatggc tagaagtcaa ttcagagcaa          11979
Gln Tyr Leu Asp Glu Ile Gln
                220 tggttcctaa aaactttaat ttcattacaa tgtaaatata atatttagcc ctacatgtaa    12039 attccctggt ataaatctgt cactatgtac ttgtaaaatg tgaaataaat tacatctttg    12099 aagttgcaac ttttagcca ttttttatatt tgcctgtctt ggtcattaag aacaattgag   12159 gtccttatgt actattttct tgattcaatt tgatttaatt ggtcaatgcc aattagtaaa    12219 ggtctataaa gaattctctt ttttttctaga ggacacttat ggctgcgttt aatttttaatt  12279 tggtttaaat ttcagttttt ttaaaattac tttttaatta tagtgtcttt aacttttta    12339 g act tta aca gaa gct aat gag aaa att gaa gtt cag aat caa gaa atg   12388
  Thr Leu Thr Glu Ala Asn Glu Lys Ile Glu Val Gln Asn Gln Glu Met
      225                 230                 235 aga aaa aat tta gaa gag tct gta cag gaa atg gag aag atg act gat     12436
Arg Lys Asn Leu Glu Glu Ser Val Gln Glu Met Glu Lys Met Thr Asp
```

```
       240              245              250              255
gaa tat aat aga atg aaa gct att gtg cat cag aca gat aat gta ata    12484
Glu Tyr Asn Arg Met Lys Ala Ile Val His Gln Thr Asp Asn Val Ile
                260              265              270 gat cag tta aaa aaa gaa aac gat cat tat caa ctt caa gtaagaatta     12533
Asp Gln Leu Lys Lys Glu Asn Asp His Tyr Gln Leu Gln
            275              280 ctttttagaat aacttattta ttcagacttc atattatctc attactattt atttgacact 12593 agaaagtact ttttctagga tgtgaatttt tgtctgtctt tttaatagtg taatatcttg   12653
tcatgttggt atatttgtcc atatgtgttt ctccaatcac ctcacaaaca ctaattttg    12713 caatttagga tatataaatg atacttgaat gaatgtgtag atagcagtca ttatggggtt   12773
ttctataaaa gactactgaa aatcctgtgg atcataacat ttcattttat cttaaaataa   12833
atacattata aatgtattag aaaccaatac attgttcagt atttatgtgg attaaatttg   12893
tttaaaaggt agaataatgt ttaaaaataa aattttctag taatgaaaga taattatgca   12953
attataagat gcagaaacta ttaaatgtca cctataattc caggatgact tcaatgataa   13013
atacacatat gtaatgtaat gtatccgtat gtatgtgtat ataagtatga atacgtatgt   13073
gtgtgtatgt agatatattt atatatataa tgtatatgta aatatgcaca ggtgtaaata   13133
tatgttacat cagtttgcaa caactcttga ataactttg tctttttag gtg cag gag   13190
                                                     Val Gln Glu
                                                             285 ctt aca gat ctt ctg aaa tca aaa aat gaa gaa gat gat cca att atg    13238
Leu Thr Asp Leu Leu Lys Ser Lys Asn Glu Glu Asp Asp Pro Ile Met
        290              295              300 gta gct gtc aat gca aaa gta gaa gaa tgg aag gtatttttt tcaattgaca   13291
Val Ala Val Asn Ala Lys Val Glu Glu Trp Lys
        305              310 taataacttt ttcttttgt attttagatt taaattttag tcttattttt ctttaaatgt   13351
cttatactgg tttataacac gtttattagg gttttttaaac ataagtttat tttatttatt  13411
ggttagaaaa gctctagaac tgtccttttt gatctctagc taatttgtta ttgaatgacc   13471
tctttcacat caatgagttt aactttaaac ttttgatag aagtctaact ccaaaatata    13531
tttggcatct aaaatatata attcgaaata taatttaaat tttttttactt aactcatagt  13591 taccttatat acattagtta aatagttgca ggtttaattt tagttttcct aactaaatgt   13651
caggttcatc agtgggaatg ggaataagca aagggatcag ataacttgg gaagcctttt    13711 caaaatacac ttttcttcct caccaccact ctccaacctt aaccaaattg tcaggcctta   13771
ccatattaga agctgggatt atgatggttg tatacttgaa aaacatcaga gattattctg   13831
aatgaataat tctaattttta aaaactatca cttctagagt cattgctttc tagtatggtt   13891
cacataaatc ttgtgggcag tttggaactg gttagcatct agggagctca gataacctat   13951
attttaaaca aaagcattag caatggaaat aaggcctata gaatcagtca tgtctccata    14011
aactttatat aaagggccag acagtgaata ttttagacca cctggtctct gctataacta   14071
aactctgctt atagcatgaa agcagccatt gacaatacgt aaatgagtga gcaaggtggt   14131
tttccggtaa aattttattt acaaaagcag atgggaggcc agatttgacc tttgggccat   14191
agtctaccaa cccctggaaa aaacagttgt ctttaccaga ttgaatgttg gcagggtaaa   14251
tggtgacatg ttatatgtat tctgtacttt gttttgactt aataccattt cataattatt   14311
ttatatcagt acgtatagta ttgctgttct ttttaaaggc tatgtaattt ttctttttat   14371
acaggtgtta atttgataat ttgtgaagtt tatgaagttt ccaatttggg ggttgtaaac   14431
```

```
tgttttaatg aatatcctta tatatgttat tttgcaaatg tacaagtata tctgtggaat    14491
aaattgctgc aagtgttgta attgtcatgt atgttgcaaa tacattctaa cagtttgtca    14551 cttttttgc tttatggcat ttttgctgt gaaatatttc ttttatgct tagttaaatt      14611 tattatttt taatgactt tgacattgt tataatgaga aaggcttctg agtataaact      14671
tgttttctca tcttttctcc taatatcttg ttttgttttt gttttgttt tgttttga      14731 gacagagtct cactcagttg cttaggctgg agtgcaatgg tacaatctca gctcactgca    14791
aatgccacct cctgggttca ggtggttctt gtgcctcagc ctcctgagta gctgggatta    14851
caggcatgtg ccgccatgcg cagctaattt ttgtagtttt agtagacatg ggtcacact    14911 gtgttggcca ggctggtctt gaaccctgg cctcaagtga tcctcctgcc tgggcctccc    14971
aaagtgctgg aattacaggt gtgactctgc ctggcctttt tttacattta aatcttcgaa    15031
acatataatt cattttgatg taaggagtat catgtggatt caacagagct actctgttgt    15091
ccaaacatct tttattgatt atttcatctt ttattgaatt gattgatcta ttttctagca    15151
gtgtatactt gttttaattt gtgtatgttt taatatctaa aaacgttatt attttctgc    15211 ttttagactt ctttatgaat attttttaatg tgaattatag aactggcttg tccagttctt    15271
aaaaaatatc ttgtggattt ttattgggta tgtgttaaag ttataaattg ttttatagat    15331
tgatttagga taaaccttt tatgttattt ggtccttcta gctaaagaac aaagataccc    15391
ttttctttca ttcattcaag atattttatg cctcttggtt gcatttaat gcatacttca    15451 taaagatcaa ttgtataaaa cttttcacag ttgtatggaa gtacttcttg tttataaatg    15511
agttttgaaa ggttgaaata ttttttaaga ttgaattata aaaaagaaa attcggtata    15571 tattttaaaa tcattttcta tttgaatttc aggttgtata tacaaaagga acagagatta    15631
tgccagtagt tgctcatact ttctcatttc aaataatttt tattttctgt atcataaatc    15691
tactaacggt gttttattatt tatgataatg aagaatgttt tattaactttt ccttttgcat    15751 aacagattct attgtgttta tttctag cta att ttg tct tct aaa gat gat gaa   15805
                                Leu Ile Leu Ser Ser Lys Asp Asp Glu
                                    315                 320 att att gag tat cag caa atg tta cat aac cta agg gag aaa ctt aag      15853
Ile Ile Glu Tyr Gln Gln Met Leu His Asn Leu Arg Glu Lys Leu Lys
    325                 330                 335 aat gct cag ctt gat gct gat aaa agt aat gtt atg gct cta cag cag      15901
Asn Ala Gln Leu Asp Ala Asp Lys Ser Asn Val Met Ala Leu Gln Gln
340                 345                 350                 355 gtaaaatctt aacagaattt tgtttatcaa ccagttttat tacagttgga actctgaacg    15961
atgtctttta tttattatat catcagtgcc tagtgtagcg gctggtacta ccaagtgtat    16021
aataatgtct tttgaaattt cttctaccac ctggtcccaa taaaaaatta gaattaagtt    16081
tagatcacgg attagactta gaactagagt tactgtgttt attttctat gtttatgtgg    16141 atagtacaca cattgttttg gttagaaatt atttaacaag aaatgattaa aaacttttag    16201
aaatttaaaa taatttata ctcttttaag gtttatttta ctgtatctta gtcctaacat     16261
accctataca atgtgaaata agctaaaagc atggttataa tttgactgtg ctacctattt    16321
tatttttagt gaaaataacc caaataaaag gaagtaatac ttttattatt tgtgctgtag    16381
ttatagtcca caagtaagaa gatgatttga aaagtgtatg ctgaataaga acaattacag    16441
gggacaacat ttttaataa agtacgaaag gggaaaaagc taagttgaat aaaagagaaa     16501
gcacagagca aaacagaaac atacaaaatg gtaaaaaggt ggaattgaat ggaggatgag    16561
```

```
gaaagtaaca tataaggaag tatagaagcc ataaacatta gggagttctg gaaatcctat    16621
tttccagagt gttagccatt atatccatct ttcagtattg gagtaacagc agtgtaccta    16681
tcattgtgta ttacagttga agtgtacaaa atggtaaaag gcatacttgt acccacaaga    16741
aaatatgttc tacagtcttg ttgaaaaaaa tcagacgtac tttttccctt acctttttag    16801
gttaatattc atgaagggat atatattgtt ttaaaatatt ttatag ggt ata cag       16856
                                                  Gly Ile Gln gaa cga gac agt caa att aag atg ctc acc gaa caa gta gaa caa tat      16904
Glu Arg Asp Ser Gln Ile Lys Met Leu Thr Glu Gln Val Glu Gln Tyr
    360                 365                 370 aca aaa gaa atg gaa aag aat act tgt att att gaa gat ttg aaa aat      16952
Thr Lys Glu Met Glu Lys Asn Thr Cys Ile Ile Glu Asp Leu Lys Asn
375                 380                 385                 390 gag ctc caa aga aac aaa g gtattttat aaatatatag ttattttata            17001
Glu Leu Gln Arg Asn Lys
                395
```
tacaattatg tttttaacga ctttattttt attaaaataa aatgtcaagt caatattgag    17061
ttttctccat ttgaatttta tattttcaaa aaattgtaca agatatttat tattatactt    17121
atattactag tgcttacatt tgtaaatgat ggatgcattt tctattattt ttctcctctg    17181
gtgaaaatta cattaacgtt tattaccagg tcactggtat gaaagaaatg aaaaattgtg    17241
atacaattat ttttatttaa cttttttataa ttaacaaaga atggaagata ataaaatttt    17301
gaccagtgta acagcattgc agatagtttt cagaggtaat ttcacattaa tcttacccaa    17361
attaatgttt catcatattc tccttaccct gagccatatt acctttttta acacatcaaa    17421
ttctatgaat ataagttctt acaatatctg tgttgttata tttccatagc actacatact    17481
atagttatgc cagggcacac tagtgcgaac tgttcatggg aaattcatgg acatgtttat    17541
tataattggt gactatgtat atatgtatac actacattta tacacgcg catggaatca    17601 ctatttcttc ttcatgtcat atatatatac atatatacac atatatatac atgtcatatg    17661
tgtgtgtgta tatatatata tttgtatata tgacatgaag aagaaatagt gattccgtgc    17721
acatatgtgt gtgtaagtgt agtgatgtgt ttgcaggtac ggttgtaatt tcaaaaatga    17781
agcaaaagcc ttgctcagga gataattgaa ccaatactta aaggaagtaa aggagtgaaa    17841
catgcagatg gctctaagca gtgggaataa gttcaaaggc agtaaagcag gagtgtacca    17901
atcatgtctg agaacaacaa agaagtcttt ttggctggag tagagtcagc aagtgaggca    17961
gtgataagac cagagaggta aacagaggcc atatcatatg gggccttata gttcattgtg    18021
cagacttggc ttttaagtga aagggacac cggggaaagt ttctgaagat agaaatgata    18081
taatttgact taggctgtgt ttgcagtaga ctgtaggagt ggtaaataag aatcagggag    18141
acctgttaga agactattgc aataatctgg agaaaagtga tggtggtttg gggcatggtg    18201
gtagcagtgg agttactgga tgcagcagtt ctggatgtat tttgaaagtg ataaaaatgg    18261
aatttgctaa cagatcagat gtaggatgtg agagagagag aactcttggt ctgaaccaaa    18321
agttttggtc atggtggggt tgtgggaaga gcaggttgag agataatcag gtacttaatt    18381
ttagacatgt taggtttgag atgcttatta gacattcaag tgaaggtgtt aagtaggcac    18441
ttgtatataa aagtttaagg tttaggacaa caatctaggc taaagatatg tttggtaact    18501
gtctctgtaa aagtaattga aataatgagg ctggctaaga tcaccaaggg agtaaatgta    18561
ggttaagaag aaaaatctaa agagcttcta ctttagcagc tggggagata aaaggagct    18621 accaaaggag actgaaaagg aaagcccaga gagctaggag gaaaagcagg agtatggaga    18681

```
gccctgaaaa ccacatgagg aatgtaacca aggaagaaga aacaactgct ttcagagctg    18741
tgttcattgc tgctgatagg tcaagatgat cactaaaagt tgactattgg acttagcaat    18801
ggtcattttt ggttcaagag aaaatgggta gagaggaaat gtaataaaga aatataggaa    18861
ccctttccca ggactgtttc tataaagaga aggagaaaac aaggtggtag cttgagggga    18921
aagagggatt aagaaaacat ttttctcttt aagatggaag aaataactca tgattttagg    18981
ttaataggag agctccatta aagaagaaac attaatgaat caatgaagtg agagagaga     19041 acttctggaa caataatatt tttaagaatg caatgggatg ggatcctagt gtgccagtga    19101
agaggttggc cttaactagg aacacagagt tcatccataa ttgtagaaaa gaaggtagag    19161
tgtatagata tcgatgtagg tggcttggta gacatcctgg taatgggaat ttgtggaagt    19221
tctaaactgg ttgctgcttt tttctcagtg aacaagggag caaggttctt agctgaaggt    19281
gaggatagga gaagatgttt cataagtttg aggagaaaga agagaagtga aagtataaaa    19341
tggtcatctg aaagattgaa gacgtggaga atgtggtatg actgttgagt aacttcaaga    19401
gcccacgata tatatatgta tttctattta tgtgtttatt atatttgtat cagaacactt    19461
tgaaagtagt ttaaactgct ttaaaaggat gactaatagt atggattgtg cgtattctaa    19521
ttactaggag aaaaagtggc aattgatctc tgctgtcaaa taaggaaaag gacttatctg    19581
ataacacttt agtcagtccg tagttatata atccctaaag ctcacagaag gtgtgtgtac    19641
tagactgtac tctacatctt gaacttaact tgtaaaacgt aatggctaat ggtattcttc    19701
cttcataaga ttaggattag gtttagttat caggaacaga gagctgaaga ataatggcaa    19761
aatcaagata gacatttatt tctcatctat gtaatggcct agaattaagc attccagggt    19821
gttgccttca tctgccccat ccaaaatgga tggaatgcag ctttatctca tgtctgtgtc    19881
ccaaacagca agacagagga agaggggcaa gagttaaaag catgtgctga aggataggca    19941
ggtaaatata gtgtttattg tgtagggcca tgtggaagaa tgataggaga atagatatgt    20001
ggatggaagg gagaatagat actggggggac aactcagcct gtgtcatgtt ccacagctta   20061
gatgttagct ccagacagct gtgctcattt cttaaaaact tttgtgatct caaacgtact    20121
agttttatgc ctaagtccaa tattaaatat ataacctata tattagtaaa tgcttataat    20181
gaatgagtgt gagaatgatc tgtcaatcaa ttttggaatg atagcaatat tatgttttgg    20241
tcttttaaca atttagtaag atattacaag taggcattta ggaagttttt agcttagttt    20301
ggattaaatt tagctgcaag tgacagaaaa atcaagcata atacaataat ttaaacaaga    20361 tagaaaattta tttctctata atatagacaa agttgaagca actagggcag gatttgtgtg    20421
acagatgctc aaatatcccc tatcaggaac cctgtctctt gttgctgtgc ctatctcaac    20481
atgtggtttc taactcatgt gaagttgcca ccctcatatc catgtggatt tcagctagca    20541
ggaaggagga aagagaagag agattactcc tttatttaa aaacatttt tttttttttt     20601 ttgaaattca catatgaact ttgcgtttat attccattac tgacatgacc acacatagct    20661
gcttgtgtgt aagtggaaat ttagttcttt atttcaaatg gccacgtgtc aagctaaaaa    20721
tccatagttt tagtacagtg gacaaagggg aggttaaata ttaggaacag ctagcagtct    20781
gtatcacaat gatcattttt tgtaaagcag tattttgcaa cctttttaaaa tccatacccc   20841 ttcagctaag aaggttttac tgaacttcag ttttttagta aattgtatta gtaaaaccaa    20901
aacaaaactt tcatcttaca aatataaaat gacaacttta aaggattttt ttttaatggc    20961
ataccacttt tcttgccacc atgttgggat cactgatttg aaggaataag tagtcaattc    21021
aattcatgat ttttgttttt actctgtag gt  gct tca acc ctt tct caa cag     21073
```

```
                    Gly Ala Ser Thr Leu Ser Gln Gln
                                    400 act cat atg aaa att cag tca acg tta gac att tta aaa gag aaa act       21121
Thr His Met Lys Ile Gln Ser Thr Leu Asp Ile Leu Lys Glu Lys Thr
405                 410                 415                 420 aaa gag gct gag aga aca gct gaa ctg gct gag gct gat gct agg gaa       21169
Lys Glu Ala Glu Arg Thr Ala Glu Leu Ala Glu Ala Asp Ala Arg Glu
                425                 430                 435 aag gat aaa gaa tta gtt gag gct ctg aag agg tta aaa gat tat gaa       21217
Lys Asp Lys Glu Leu Val Glu Ala Leu Lys Arg Leu Lys Asp Tyr Glu
            440                 445                 450 tcg gtatgtattt ttatcttgtc attcaaggag cttagaatta ttcttgccat            21270
Ser tcacagacta ttctgtgcta tttactgcat accatttaaa aaacattcca taagtatctt     21330
ttgataaaga ttatcctcat taatttatac taaactattg aaacctttga gcatttactt     21390
tttgccagaa ttgttttcaa acttttgatc acagtgattt gtccaaataa tcagttttgg     21450
tgaagcagca ggattacttt tttttattat ctgtgttcat tgggccacca tgtagatgtg     21510
acaccactgg ccaatttgac agaatttatg acaggaacat actgtgtcaa tacaacctgc     21570
tctccacttt ttatactttt tcattggtta caactaattc aagcaactaa tgacttactt     21630
attctactgg tattgctgat ttgcttttac taattctttt agtattttgg taagtgtttt     21690
ttatatgtaa tgcatattca gagtcacttt gcctttagga tattatactg gaaagtttta    21750
actgttgcat attacatcat tattattact ggatttggtt tataaaagca caataaaaaa     21810
ccagtgtaat gatataaatt ataggcatat gtacattttc ctttagactt agtaaaaaaa     21870
aaatcatgaa cttgataaat ttattcaagt aaaccatgtt atattttaaa ttaaattgga     21930 tattttcag gga gta tat ggt tta gaa gat gct gtc gtt gaa ata aag        21979
          Gly Val Tyr Gly Leu Glu Asp Ala Val Val Glu Ile Lys
                    455                 460                 465 aat tgt aaa aac caa att aaa ata aga gat cga gag att gaa ata tta      22027
Asn Cys Lys Asn Gln Ile Lys Ile Arg Asp Arg Glu Ile Glu Ile Leu
            470                 475                 480 aca aag gaa atc aat aaa ctt gaa ttg aag atc agt gat ttc ctt gat      22075
Thr Lys Glu Ile Asn Lys Leu Glu Leu Lys Ile Ser Asp Phe Leu Asp
            485                 490                 495 gaa aat gag gca ctt aga gag cgt gtg g gtaagccatg ttttaagtta           22123
Glu Asn Glu Ala Leu Arg Glu Arg Val
            500                 505 catagtttgc gcaacctgat ttacaagtct tttttttaa tttaaatttt gtttattatt      22183
atttattaag tagtttaatg cttttttcaa atgcttttat aaaacattta atacaaataa     22243
aagtggagct aacctgattg aagtggaatc agatttatg gggttggagt ggtgggtggg      22303
cagggctgga acattgcttt atttggtcta gcatctcctc agtaatagct gcttgtttaa     22363
aaagatgaaa gtttattaat accacatatc agagattaac cttttttttt cccaacaaaa     22423
gtagggtctg tattacccat gtttgtttgc aaaatgctct tgtaacagat gagatattta    22483
aacttcttgc tctgtgttgt gattctcctg cctctgcctc ctgagtagct gggattacag     22543
gtgtgcacca ctatgcccgg ctaatttttg tattttggt agagatggga tttcaccatg      22603
ttggctaggc tggtctccaa ctcctgacct taagtgatcc acccgccttg gcctcccaaa     22663
gtgctgggat aataggcatg agccaccgcg cctggcctgt taaatctttt taaagatttt     22723
taagtacttg attttataa tttagactac ttacgtttta ctttgttcga gtattttaag     22783
gagtaattag taatatagct tgagagttta tatttattt ttaataaata gcctattagt     22843
```

```
taatattact aatttgagtg ttatgatagt gcagactaag ttgctgcttt aaaatgaaaa   22903
taaatatcta aatatcaatt tcattattgc taaatttcat ttaatgcttt cttagttaaa   22963
aatgatcatt tgtaaaaact attatctaaa gaaaagacaa atagacaaat aagtatttta   23023
tacagatata tatgtgtgaa aagtatctaa cttggatccg tagttgtgct aggaccccaa   23083
attagacttc tgatcaactt ggactatcag atcacagcct tctgatcaac ttggactatc   23143
agatcacagc caagaatctg gaagttccta aagatgactt ctggcccgtc taggtagctg   23203
tcatagacat catattttct gtgcttaaaa agctccaaat cttggtttat aatttcattt   23263 aggttttgt taggatttcc attaataatt gtgataaaat tttaacttgg gttacagttt    23323
aaatatctgg aaaattcttt cacagaaagt tacctcattc ttcagtgata ctggctaagt   23383
gaattataac cagttgcttg atggtatatg acatttttgc agcttatttg aatgttttta   23443 agttttaat tatattgctt tctattgtag gc  ctt gaa cca aag aca atg att     23496
                                    Gly Leu Glu Pro Lys Thr Met Ile
                                                510             515 gat tta act gaa ttt aga aat agc aaa cac tta aaa cag cag cag tac     23544
Asp Leu Thr Glu Phe Arg Asn Ser Lys His Leu Lys Gln Gln Gln Tyr
                520                 525                 530 aga gct gaa aac cag att ctt ttg aaa gag gcaagtgtgg tagtcagttg       23594
Arg Ala Glu Asn Gln Ile Leu Leu Lys Glu
            535                 540 attattttct tggctgaact atagagaaat actaataatt tatactttgc ag att gaa   23652
                                                          Ile Glu agt cta gag gaa gaa cga ctt gat ctg aaa aaa aaa att cgt caa atg     23700
Ser Leu Glu Glu Glu Arg Leu Asp Leu Lys Lys Lys Ile Arg Gln Met
    545                 550                 555 gct caa gaa aga gga aaa aga agt gca act tca g gtatactcag            23744
Ala Gln Glu Arg Gly Lys Arg Ser Ala Thr Ser
560                 565                 570 ttattctaaa cctttaaaaa gaattattga taagtgagtt gtctggatat gaaattattt   23804
gtgtcttagc tgtttttgct gttctattgt ggatctgcta caaatttaat aaatgacaat   23864
aataacctga aggagataag tgagtgtcag tgggttcagt cctgaatctg aaatagacaa   23924
aaacaaaaca aaacaaaata acaaaaacca agcaaacaaa aagaaaaaa accttagaat    23984 tatgaatttt tgaaaagtt ttatagtata gtatttaat ttctagacag caccaatatg    24044
ttgttattaa taataataaa acttagtagt ttttatgtta atatatgtta ctcaacattt   24104 tcccttttcct taaggactat gcattgaaaa gcttttcttg taagttatta ttattattat 24164 tattattaat atttgagatg gagtctgtct tgttctattg cccaggctgg agtgcactgg   24224
tgcgatcttg ctcattgcaa cctccgcctc ccgggttcta gtgattcttg tgcttcagcc   24284
tcctgagtag ttgagactac aggcgtgagc caccacgcct gacttatttt tgtatttta   24344 gtagaaacag ggtttcacca tgttggccca ggctggtctt gaactcctga cctcaagtga   24404
tccatccact ttggctcccc aaagtgctgg aattataggc gtgagccacc atgcctggcc   24464
ttaaattatt ctttttctaag tgaaagtaat gttttattga atataaatta acatctttct   24524 tgggttatt ttacttgagc taaagagaac agttggttaa gttttataat agccattgca   24584
gtgctttttt gtaagaagac cacacagaag gactgtcttt ttcacttgcc ccaaatcccc   24644
aagcacgtat atgagtaata gcagagtggt tctttttagc attatgattt ctataataca   24704
tccaaaactt tctcaagaaa aaacttcatg atttattagt acaataatca gtttactcat   24764
tactcatcat ttatatttac tttatatgtc ttttaactgg tgcttattaa gtagcacttt   24824
```

```
aatatagaat aggcaaagaa tggtagagaa gatgaaattc aaaaattagg ttctcacatt   24884
attaatagtt cattaaaagt gagctaaatg agaagcttgt attggctatg tagaattttg   24944
gagggatttt ggaaacaatt attctacctt tgcattaaaa cttgattgta ggttttaaga   25004
attaaagtgt tggaatagta ggagggttat tttaatgttt ttagtttgtt aattctctta   25064 tatatag ga  tta acc act gag gac ctg aac cta act gaa aac att tct     25112
        Gly Leu Thr Thr Glu Asp Leu Asn Leu Thr Glu Asn Ile Ser
                        575                 580 caa gga gat aga ata agt gaa aga aaa ttg gat tta ttg agc ctc aaa     25160
Gln Gly Asp Arg Ile Ser Glu Arg Lys Leu Asp Leu Leu Ser Leu Lys
585             590                 595                 600 aat atg agt gaa gca caa tca aag gtaatagtaa agtattgcaa agagagtaaa    25214
Asn Met Ser Glu Ala Gln Ser Lys
                605 ggaaaatatt ttttttttt ttttttttg agacggagtc tcgctctgtc tcccaggctg    25274 gagtgcagtg gcgcgatctc ggctcactgc aagctccgcc tcccgggttc atgccattct   25334 cctgcctcag cctcccaagt agctgggact acaggcgccc gccaccacgc ccggctaatt   25394 ttttgtattt ttagtagaga cggggtttca ccgttttagc cgggatggtc tcgatcttct   25454 gacctcgtga tccgcccgcc tcggcctccc aaagtgctgg gattacaggc gtgagccacc   25514 gcgcccggcc aggaaaatat ttttattgtg ttttcatttc ttccccgttt atctcattct   25574 tgaacatcta atcttattat tgttgttaaa taagtagagg gaaatatttg cttatttaac   25634 ctgttgattc aaagattgat taatgagaca ttatttactc tgaatacaga ttaggagttc   25694 agataaagca gagctgctgc ataggagatc atcattcaat accccacagt cagatcagaa   25754 tgagacagaa gagaatatga ccataggatc attatcaaga atgttatctg aaattcacca   25814 tagtgtagaa agtggaatgc atcctttgt ccctttaact agactttctt catccatgca    25874 agttaaagag aattcaactc cagaaactat tacaataaga gagattttta aagcaccatg   25934 tctgcagtct tcaagaaatc tagaatcgtt agtcagcacc tttagtaggg aaagccatga   25994 agaaataaat gacatatgcc ttttttctga tgactgtatg aagaaggtgt caagaagcca   26054 tcaagcacta gagaagacta gttttgtaca aaaaagcaat tcatcttttc atggcttatc   26114 aacagcttca gacataatgc agaagttatc acttaggcaa aaatctgcaa tattttgtca   26174 acaaattcat gaaaatagag ctgacatgga taaatcacaa gtagcaacat tagaagaaga   26234 acaggttcat tcccaagtaa agtatgctga tatcaatttg aaagaagata taataaaaag   26294 tgaagtaccc ttacagacag agatattgaa aaataagctt aaggttaatc ttccagaccc   26354 tgtgtctatt actgcacaat caaaattatc tcagataaat tctcttgaaa atcttataga   26414 acagttacgg agagagctag tatttcttag atctcaggtg agttttctc caaattatat     26474 ttctgtggtt gttctttat gacgtctcta caaagttct gtaacaatta tagttagaat     26534 attttgttt gcactttaac atcagttata cacattgtac ttttaaaat ctaaaatgca     26594 gtacattgat atgaactcat tgacttgtct aatttattaa attttctttt agaatgaaat   26654 catagcacag gaattcttga tcaaagaagc agagtgtaga aatgcagata tagagcttga   26714 acatcacaga agccaggcag aacaggtagt gtaaaggcag aacattaaaa gagatgattg   26774 tggtactaaa gacaaaaacc gttatatctt tttgcctctt accatggatg ttgggagagg   26834 gagaaagtgg gattaagatc accatctgct ttactgttta gatttagtt tattttatg     26894 attgctgcta tgtcttcata gctcgttttt ttgtttttgt tttgttatac ttaattgatc   26954
```

```
aaacttttct taacttgaaa attatagact tgtgatattt tgttgaaaaa aatcaatttt      27014
attctctctg ctttttttcag aat gaa ttt ctt tca aga gaa cta att gaa aaa     27067
               Asn Glu Phe Leu Ser Arg Glu Leu Ile Glu Lys
                   610                 615 gaa aga gat tta gaa agg agt agg aca gtg ata gcc aaa ttt cag aat        27115
Glu Arg Asp Leu Glu Arg Ser Arg Thr Val Ile Ala Lys Phe Gln Asn
620             625                 630                 635 aaa t gtaagttaca attatctttt acttttctgt tcttattttt cctatactta           27169
Lys aaatcatggg cctaaaaggg cgttaacaca ttctctgttt tctaatctgc tttactccta      27229
attacctctg tactgtatat acttcagtct gtcactatcc agttgatttg ccttgctgtt      27289
ttcattgtga gagaatgtta ctaatatgaa ttttttgtga aatatataa ctcctttttc       27349 ttgtgtgttc ttcaatcaaa atgaagttag aacaccaaat ttaaaatact ttaatataaa      27409
gcatagttta agtaaggca gaagtatgcc ttatatacgt gtgtatatgc acgtgatata       27469
aataggtctg tcatttaact caactattca cgttggattt atagttgaat tttttttgtat    27529 gtttatttac atttggattt ttccaatgat gtctttggta tatgtgaaat atttgtcatc     27589
tgtatagcat agtgtaaatt gtgaaaaaga tctgatcatc caatgagaaa actgtgtaat     27649 tacag ta   aaa gaa tta gtt gaa gaa aat aag caa ctt gaa gaa ggt atg    27698
           Leu Lys Glu Leu Val Glu Glu Asn Lys Gln Leu Glu Glu Gly Met
               640                 645                 650 aaa gaa ata ttg caa gca att aag gaa atg cag aaa gat cct gat gtt       27746
Lys Glu Ile Leu Gln Ala Ile Lys Glu Met Gln Lys Asp Pro Asp Val
            655                 660                 665 aaa gga gga gaa aca tct cta att atc cct agc ctt gaa aga cta gtt       27794
Lys Gly Gly Glu Thr Ser Leu Ile Ile Pro Ser Leu Glu Arg Leu Val
670             675                 680 aat gtaagttatt tttttcatgt taatgttttt ccctatcac tttagagaga             27847
Asn ttttctgctg tgtacagatc tccatagttt ctgatgagat attttttagtc atttgaatca    27907 ttgtttccct gtatgtaaag tgtagttttt cttgagctgc tttcaatact tttcttctac     27967
caattggata attgttatta atctgtcttc aagttcactg acattttcct ctttatctgt     28027 gttctttttgg ttcaagggtc agcttgagac cttgaggagt ttttttacacc gactttggag    28087 ctcgttttttg ctgactcttt tcttattggg attttccttt cacttatccc atggctttgg    28147
gctgtatcct gtggttttct agatgagaaa gatgatagat ctctgcaatt gcaccctgcc     28207
ctatgactaa atctttaaaa atggcaaagt caatctttgc tggtcctgtc ttccgtattt     28267 gagggggtttt ttcccaaaat ctgcttgctt ttgttcattt tctagaacat ctaggtagtt    28327 tttttttcatt catttttttat ttatgggagt gtagatctct taggaactta tgccatcaga  28387
agtattatga aatggcttta ttctaaatgt ttaaagattt actcattgct acaagaaaga    28447
tttagccatc actaatattc tatatatatt taccatatag ggacttgaga atttcacagg    28507
attcagtatc tgtatataaa cttgaataat atacacattt tagattgtta atatttaagt    28567
atatgtcatt tatgttatct gaacatattt agcgtacatt gtcatattat ttcccaaatt    28627
tgtgcttgat ttcaaatggg aaaaaaattc ttattattta ttgaattgtt ttttttaaaaa   28687 aatcatgatt aatcagtaat tggatacttt ttaaaataac actataattg ttaacagaga    28747
atgagagtga tactggtatg ttaaaaaactt cctgaggcaa gaaaataatt tgattcccat   28807
tatatctttc tcatactgac tttccttctc tgattggtga ttttgtttttg cctctgccac   28867 tttgaatgtc taaaatgatt ctttatgctt tttttatgtg aacatctttt gtccgtgatg    28927
```

```
atgcccacta ctgatactgt gtcccagatc aaacttaatt ttccaagggc agctctactt    28987
agtgaccaaa tgaaaacaca gtgaatagcc caagaaatcc taacttctat ttatgttgac    29047
aatctctgga ccttcctgaa gccactgttt gcatagactt catttacttt tatccgggat    29107
tgtcattgtt ttttcagatt cataggccct atctgaaatt cacaaatcac ctagcaatac    29167
ttctctaaga aatcttcaga atccatgaca atttagacca gacaatgctg gattatgcac    29227
ttcagttcac ttttttgttac tacaaggtat ttttcagtgc ccccaacagc tatcttaact    29287
cattctcatt ttaccaaagt ccatgtagac acggcactat tcctcaatga gacaactaac    29347
tagaccacct tgttgtcagt cagagtacct tcctctacct acttttatct tccttatatc    29407
ctctttgagt tagtataagt tattactctg catgacctgc tctaatctcc ttcaggggaa    29467
ggcttttaca aatctactac ctagagttaa accccagatc accttcctga gtaggagatt    29527
gcatttggtt ctattcattt taccttattt ggcttctacc ttcacttttt aagacttact    29587
ttgcctttaa cagtttttttc catacagttc atctaaagtc caaatatatt tattagatgt    29647
gtgcattgtg tgtatatact tagatatgcc actgttggag atttcgggcc agtgatgcca    29707
ctctgataat attttaatat ttgacatatt attttttgctt actcattatt cttagataat    29767
atcatgttat gataccttgc ctttattttt atttatgctt caactatgtg gagaggaagc    29827
actgaaaaat tcacttaatt gaatgttgta ttgatcaatt gttcaatatt gtattccatt    29887
cctttgcgca tgctttgaat gcaggtgcta tataatttca gagaaaaata cctcattttg    29947
actgtacaaa aacccccatgt agggagcaga gctcacattg ttttccccctt ttagagacaa    30007 gaaaactaag atacagagaa tttaagtcac ttgcccagct gttaagtgac tgattaaaat    30067
ttgaaccctg gtcatcttat tcccgtctgg ttgttttttct agtctaccag tctattaaga    30127
ttagctaggt gttttttaat tgttttaatg aagtaattac tatgcttggt aatgtaaatg    30187
aaagttttat agattcataa ataagaattt gaattggcat actttattat catgcttggc    30247
aatgaaaata ggaaaatgct taaatgtcca ttttatttaa agacagactg tttttttacta    30307 tgatttttact gtttttctcc acatttctaa tatataatat aaatttgcta g gct ata    30364
                                                             Ala Ile
                                                                685 gaa tca aag aat gca gaa gga atc ttt gat gcg agt ctg cat ttg aaa    30412
Glu Ser Lys Asn Ala Glu Gly Ile Phe Asp Ala Ser Leu His Leu Lys
        690                 695                 700 gcc caa gtt gat cag ctt acc gga aga aat gaa gaa tta aga cag gag    30460
Ala Gln Val Asp Gln Leu Thr Gly Arg Asn Glu Glu Leu Arg Gln Glu
    705                 710                 715 ctc agg gaa tct cgg aaa gag gct ata aat tat tca cag cag ttg gca    30508
Leu Arg Glu Ser Arg Lys Glu Ala Ile Asn Tyr Ser Gln Gln Leu Ala
720                 725                 730 aaa gct aat tta aag gtgagaattt tattaaataa aagaaaatgc taaacataag    30563
Lys Ala Asn Leu Lys
735 aatgtagatt taataggaaa ttttttaattt tttaaaaaga atgctttatg agaaaatgcc    30623 ccttgaatta attctttcaa tattaagaaa ctggatttct cttataaaat tataagtgga    30683 aaataagtgc cttataagat tgaaagaat acaaaaattc taaatctcat acctaggcat    30743 ttctaagcag aaactgaagt atggttgagg taaaattcct ggcagggcat tcacatatct    30803 gtcaatttgt ctttctttgg gtgtaagagt tgtgattctc attgctggat ttttttttcc    30863 ag ata gac cat ctt gaa aaa gaa act agt ctt tta cga caa tca gaa    30910
                Ile Asp His Leu Glu Lys Glu Thr Ser Leu Leu Arg Gln Ser Glu
```

```
                        740                 745                 750
gga tca aat gtt gtt ttt aaa gga att gac tta cct gat ggg ata gca           30958
Gly Ser Asn Val Val Phe Lys Gly Ile Asp Leu Pro Asp Gly Ile Ala
755                 760                 765                 770 cca tct agt gcc agt atc att aat tct cag aat gaa tat tta ata cat           31006
Pro Ser Ser Ala Ser Ile Ile Asn Ser Gln Asn Glu Tyr Leu Ile His
            775                 780                 785 ttg tta cag gtattgaaaa ttttgttaca ggtattgaaa attttacatg                   31055
Leu Leu Gln tgaataacaa aaatcattgg tagtatgttt ctttatgttt ttatttttat tttactttat         31115
tttaattttt ccatcaccaa agcatgcaga tagtactttt ctcaatattt agtcttcatg         31175
tattcctgag ttctcaaaat agtaacagtg aaatatattt tttatggatt ttgatgttag         31235
atggattata aataaaagca atttatacca ttcattccat tcatctgcat gagcagcatg         31295
ttcatacatc ttgttcgcac acctgtcatt catgtgaaat atatggttca caagcagaac         31355
aacaagcagc tattataaag cagtgttaag taaatgagca cttttatttc ttgctgggtg         31415
gaaaacaaaa gaataaagtc tgtcaaggct ttttagtgtc atgatagaat tgttcccctt         31475
tttgcattca caagtaaaaa ctacttttttt tttgagacag agcctcactc tgtcactcag        31535
gctggagtgc agttgcgcta tcttggctca ctgcaacttc cacctcctga gtttaagtga         31595
ttctcatgcc tcagcctcct gagtagctgg gactacaggc atgcatccct ggctaatttt         31655
tgtattttttt tttagtagag atggtgtgtc gtcatattgg ccaggctggt ctcaaactcc        31715
tggtctcaag tgattcgcct gccttggcct cccaaggtgc tagggttaca gacgtgagcc         31775
actgcacaca gccataagca aaaacttcta aaccaaatta ttcttcatct ttgtcttccc         31835
tttacgcaat aaaatgttaa tctaccacca aagaggaaag ggtactctac tatactacct         31895
gccctgggtt tctcagttttt gctgtctata taatggtcgt tatgaatgtc ctaatgacag        31955
atccttttca ttattttatt tgaaatttga ctatctataa catcacatac attataaata         32015
taattacaaa tatatgttca gaatcaatga aaatatattt ttgattatat gggccactat         32075
ttctctctgc taggtgatcc atttgtgagt atacttgagt tataattatt aagtactcat         32135
ttttattttg gaaattacag taattcatct tttttctcaat attgggattt ttattattat        32195
tttatgttgt ctaaggacag ccttaactac ttattagaat attgctttgt atgtgatatt        32255
attatttta aatgtataat tttaacatta ttatttctct tatttacctg aggtataggg          32315
acactatcag caaatattgg tagtatggca ttgtcgtatt ttttgagata aaattcatga        32375
ttttaatct ttgtataaga aatatatcag aagtttgtag tagattagag agtaccaact          32435
gggagtctga aaagctgtcc aaagtggcaa acaggtact tagactctca atcctaaggc          32495
tgtatagagc tataaacgtg gcaagacctt tggagtcaga cagacccaaa ctcaaatgtt         32555
ggatccatgt atatggaaag cacctgacaa caagcctagc atatgtactt ggtaaaaatg        32615
attgccaagt gtagtgttaa tgagttttttg gatattgagt aagttattta aatttcaatt        32675
tcatctttaa aatgaaataa ttggaaagga taatttgagt gagggtatga aattatgtgt        32735
tcataagaga gggtatgtgg ccgagtgact agaggcgagt ttataactat tctatctaat         32795
aaaactttgt aatctggtaa tttgtgtgct aaaaataact ttacctgttg tatagtactc        32855
ttttttttatg ccttaaacta aagtgttcaa aatatcatgg aaaaatgatc tgtgttgctt       32915
acagatttgg tgacttttaa ctttcctata atgttgtcag aatatgaatt tatactttca        32975
aattcagcat ttattctatt gtgtttttttt ttgcattctt atttctaaac cacttttcag      33035
```

| | |
|---|---|
| gaa cta gaa aat aaa gaa aaa aag tta aag aat tta gaa gat tct ctt<br>Glu Leu Glu Asn Lys Glu Lys Lys Leu Lys Asn Leu Glu Asp Ser Leu<br>790                795                800              805 | 33083 |
| gaa gat tac aac aga aaa ttt gct gta att cgt cat caa caa agt ttg<br>Glu Asp Tyr Asn Arg Lys Phe Ala Val Ile Arg His Gln Gln Ser Leu<br>810                815                820 | 33131 |
| ttg tat aaa gaa tac cta ag  gtataggtat tagcaaaact ataaatataa<br>Leu Tyr Lys Glu Tyr Leu Ser<br>              825 | 33181 |
| ttgcagtata ttcttgttaa ttgtgaaagt aacgtaagaa taatttatgt tttgttcttc | 33241 |
| ccttcttctt cttcctttgc aattgtattt tttttactc tggtaactac tgttaggaac | 33301 |
| ttatttatgg agacagtgta gcttaatgat tacattaagc ctgggattat cctgcctggg | 33361 |
| tttgagtcat ttaacgtttg cttttttgtaa gagcttgagc aagtcatctt acctatctgt | 33421 |
| gtctcagttt ccttatctgt aagttacttt gtaagtaata ccctttttcat aggattattg | 33481 |
| taaaacgtaa atgaattatt agatgaaaat gctcggacta gtgtgtggca catatgaaca | 33541 |
| gtttgtaaat gttagctgtt gttagcatca ttcatcatca tcacaatcat cattgttcat | 33601 |
| atatgtttat agggaactaa catatttctc cttatttctg tcatctcatc taaatcaata | 33661 |
| gaatgatttc cttaatagga attagaatac ctaatcaaag gtgatttaaa cactaagaat | 33721 |
| aattattatc tgacctaacc agaaccacaa agctagttgt agggcaggtc atatttgaag | 33781 |
| gttgttgtta tcgcctatga tggttgtaaa atagctgcat gaattcaaga aagatgatgt | 33841 |
| gcccattgaa gaagaggagc atttttttct acatagcttt tattttttaaa taaacatttt | 33901 |
| tttctggtga tacctggcag acattgactc cgatctcatt tgctagaatt ggatcacatg | 33961 |
| tccaagtctg aaccattcag ttgcaaagag aatgataccg ctatactggg tttatgccaa | 34021 |
| gaacattaca catgtttgtg gaatgctcat gtgtagacaa cagtgtctta cacaacttca | 34081 |
| aaaaaataat ttatatataa atatgtttta aattactttt taaattcaca agaatttatg | 34141 |
| gtatacaaca tggtgttcta tatatgtata tactatgcta tacaacatgg tgttctatat | 34201 |
| atgtatatac tatgctatac aacatggtgt tctatatatg tatatactgt ggaatggcta | 34261 |
| aatcaagcta cttaacatat gtattacctc gcatactttt ttttttttt ccttgagaca | 34321 |
| gagtcttgct ctgtcaccca ggctggagtg cagtggcgct atcttggctc actgcaacct | 34381 |
| ctgcctcctg ggtccaagtt attttcttgc ctcagcctcc caagtagctg agattacagg | 34441 |
| catgtgccac cacgcctggc taattttgt attttggta aagacggagt tttgccatat | 34501 |
| tgtccacgct agtctcaaaa ttcctagcct caagcaatct gcccaccttg gcctcccaaa | 34561 |
| gtgctgggat tacagcatac ttcttcttat ttttttttt ttttgcacta agaacactta | 34621 |
| aaatttactc tcttagcaat tttaaagtat ataatatact gttattaact ttggtcacta | 34681 |
| ttttaattag acttaagatg tgtttgtatt caaattattt tgtaagcatt taacacccaa | 34741 |
| atttgagagt ggggtcagaa tgttggaatt tgatttctag aattagtata gggtattatt | 34801 |
| ttcctacttt ttttctgtgt tcaataaaat gtttataaga ttcagcttca attatattat | 34861 |
| aacccattta gtggtgaatc agggaagaat gaaaataatt tgataacttt gttgccttgc | 34921 |
| atttatttaa aaaattttta attctaggct aaaccctttt taaatgaaag tttaacttct | 34981 |
| tgtgttttca gatactgaat agctatgata cctcttgtgt tgagaaaact ttaaatttgc | 35041 |
| ataatctgaa gttatctttt cttataaaca ttttattagg tttacagtat tgtctttttg | 35101 |
| ttttgttttg tttttag t gaa aag gag acc tgg aaa aca gaa tct aaa aca<br>                         Glu Lys Glu Thr Trp Lys Thr Glu Ser Lys Thr<br>                         830                835 | 35152 |

```
ata aaa gag gaa aag aga aaa ctt gag gat caa gtc caa caa gat gct      35200
Ile Lys Glu Glu Lys Arg Lys Leu Glu Asp Gln Val Gln Gln Asp Ala
840                 845                 850                 855 ata aaa gta aaa gaa tat aat gtaagtaaaa cattttaac attagtatgc           35251
Ile Lys Val Lys Glu Tyr Asn
                860 aatattgtac aaagtaggat agctagattc aacaagtaat atggatgtgt ctttgtgcag     35311 aat ttg ctc aat gct ctt cag atg gat tcg gat gaa atg aaa aaa ata      35359
Asn Leu Leu Asn Ala Leu Gln Met Asp Ser Asp Glu Met Lys Lys Ile
        865                 870                 875 ctt gca gaa aat agt agg aaa att act gtt ttg caa gtg aat gaa aaa      35407
Leu Ala Glu Asn Ser Arg Lys Ile Thr Val Leu Gln Val Asn Glu Lys
            880                 885                 890 tca ctt ata agg caa tat aca acc tta gta gaa ttg gag cga caa ctt      35455
Ser Leu Ile Arg Gln Tyr Thr Thr Leu Val Glu Leu Glu Arg Gln Leu
895                 900                 905                 910 aga aaa gaa aat gag aag caa aag aat gaa ttg ttg tca atg gag gct      35503
Arg Lys Glu Asn Glu Lys Gln Lys Asn Glu Leu Leu Ser Met Glu Ala
                915                 920                 925 gaa gtt tgt gaa aaa att ggg tgt ttg caa aga ttt aag gtacatctga       35552
Glu Val Cys Glu Lys Ile Gly Cys Leu Gln Arg Phe Lys
        930                 935 ttcttatttt gctttttctg actatgaaaa atttcaaata tgcagaagat aggatggtat    35612
caataatgct catcacctga attaatagtt aacatttatt aacattttgt cataattgct    35672
tcttctgatt tttgtgggat gtttgaattg cagacattcc tccctaaat atttaatgta     35732 ccctttttgaa aaaggctttt ttctttaact aaccatagta actttattat acctaacaaa   35792
atgacagtaa ttttctaata tcgcctaata ccctgattat agtcacattt tttacatttt    35852
ttgatcaaag aataagcatt tggatgttac atctcataaa tcttttaat atagaatccc     35912 cttggttttc tttttctcca aaaatgttt gaagatgtat ctaacttttg tgtgtgtgtc     35972
attttacttg ttcctgtgtc ccttgtatta ctaaaagtta ggtcagaacc ctaagttaca    36032
ttcaggttta acatttttg gcaagaatac ttcataagta gtgttctata ctttatattg     36092
catcacttca agagtatctg gttgttccat gttttgtaat tgattactct gttaaggaaa    36152
agacaagcag accaagtatg gtggctcatg cctataattc caacattttg gaaggcccag    36212
gcaggaaaat ttcctgagcc cagaccagcc taggcaatat agtgagactc cgtctctaca    36272
aaaaatgttt ttttttttgt ttgtttgttt ttaattagct tggtgtagtg gcacatgctt    36332
gtaatcccag ctacctggga cattgaggtg ggaggatcgc ttgagcccag gaagttgggg    36392
gctgcagtga gctgtgatca tgtgccactg atctccagcc tatgtgcctg tataacagag    36452
cgagtctctc tcttaaaaga aaaaagaag aagaagaaga agaaaagata accatatacc     36512
tccattatta agcaatttag ctaactggtg atattttggt accatacaaa taacaaatta    36572
tttgtcagtc ctaatgattt tagcatctgc tgatgattgt tgcctaaccc aattattaaa    36632
agttgcaaac atcataattt tctagttata ttatgcactt acatttatta acagacatgc    36692
ttttgtaaaa taaatagcgt ttcctcatta gcccaggcta tttgtttatc ttgaagttta    36752
gctcctacta caaaggcaag ataaatgctt ttctctttaa ttaccagttt tcagaataca    36812
cacttggtgt actctgcact acctgctttt tttgtcccct ccgctttctc tttttaagt    36872 atcagattag actcacagat ttttaaatat tccatgtgtt ttagtggag tcatattctt     36932 ttgtctcaac tttagccaaa gagagtcctt taaagttgac tcttatattg tcttgacaaa    36992
```

```
aattcattag tcttttgaac gaagcctcaa agcttgactt gttttctagc ataagatgtc    37052
ttagacttac ctacatactt catgcccata cttggaataa accatttctt taaagagccc    37112
aggttccttt tagtggggaa ggcatttaga taccaaaaac tggccactgg gcatcattgc    37172
tctcagagta tcattgccac tagtctctca gtagacaagt tagaaaaata tgtatatatt    37232
taaaccatga gttcatattg ttatttccag tttaattata acattatggg gtaagtaaat    37292
agtatcggat tttactaag cttctttgat tttgcacttg tattttttc ttacatagaa    37352 aacctttatt attaacatta aaatatttgt tttatcctac aatatacata caataatttg    37412
aaaaataata cttgaattga tattaatagt aacaacaaca gcactgctgc caaacatagt    37472 ttaaagttttt atttcaggtc ttatttctt cagaatatat cttgctgaga atgtataggc    37532
aaagtattct acacttactt gaaataattg tcttcatgcg gttatgttat acatttgata    37592
tatagttagg ctcattgtt tttcattttt tttattttag ggattttttt cctttattga    37652
attttaatat atacaatatt tatatatgca aaatatttaa tcagagaaat cttaattctg    37712
gtcttacgcc tttcatatta ttctgctcca ccctctgtag gtaacttatt atcttctca    37772 tgtttccttt tggaaacat aaacaaagac aagacaggtt acatgacatg tatacccttc    37832
tgcacctagt tttatacctt accttgtagt ttattttaa gcatgtaaat gttcaatgtt    37892
catgactaaa tttggacagg atcataggaa cacagaattc aaagtgaaat taaaatgggc    37952
ttgggttctt tactttccac tttaaaggtt gtaatgggtg atgtcaggct aataaaccta    38012
ttttcagctt gatctaaagc ttaatactga gcatcaagaa attctttaat aaatataagt    38072
gatatttatt cagacatgta ataaggaaat gttcatgtct tatttttgtg ttagattttt    38132
ttagaatcta cttttgttag agttttataa atacagttag tgtttgagat agaaagagaa    38192
aagaattagt tttcttcctc ttctacctgc tcatgaactt gatttttttc tcccaacaat    38252
tgaagagcca agaaaaaggg agattcttaa gagatgggaa atagaatctc atctacccct    38312 gtttcccca gaacagtgaa actgaatctt aagggtaaga tagaatagtg tgtacttaac    38372
ttagatggag aagaaaggct gccaaaatga gatctgaagc gctattacaa atatttccat    38432
cgttactgta cttcagaatg aattacaacc gtaagttttt ttacttcctc attcataaat    38492
ttgattattc cttataccac ttctcagctt tcatcattct ttattgtact tttctatgta    38552
atgtttgcct attatacagc aacttaagag aactgtaagt ttggacattt cattttggtg    38612
ttgataatag aatatctttg aatagttcta tagttgatga gtagaaccat gaaccaagta    38672
acttaaagtc cttgatgtta tttattacag agaactataa tagaagctct cccgctaatg    38732
tttccatcat gtgtacaaaa agtttcttg ttattaaagc tagtccgttt aacttacaat    38792
aagcataaat agctaagctg tgaaagttac ctgtgataat gctaattttc ccatttatta    38852
aaaggcaagt tgttttccga tcataagaaa tttagaaaag ccatccaaag ataaattccg    38912
agtgatatat tcctgctgtt tgttatgttt tctcaaatta attgagtttt attttacaat    38972
gacaggagtt attaaagtat tttatttta ttatgattaa gattttcaaa gtaacatttc    39032
ttatatgaaa gaattatgt taatgcatgt ttttcttaca tgggaaatca tatatttaa    39092 aaatgatttt aaaattcgtt ttactttaag ttgtattatc tttctcaaaa gtggctagtg    39152
cttgaccaga aaaaagaca ccagcataac tcagtgtatc tttatttaca tag gaa    39208
                                                             Glu
                                                             940 atg gcc att ttc aag att gca gct ctc caa aaa gtt gta gat aat agt       39256
Met Ala Ile Phe Lys Ile Ala Ala Leu Gln Lys Val Val Asp Asn Ser
        945                 950                 955
```

| | | |
|---|---|---|
| gtt tct ttg tct gaa cta gaa ctg gct aat aaa cag tac aat gaa ctg<br>Val Ser Leu Ser Glu Leu Glu Leu Ala Asn Lys Gln Tyr Asn Glu Leu<br>960                       965                         970 | 39304 |
| act gct aag tac agg gac atc ttg caa aaa gat aat atg ctt gtt caa<br>Thr Ala Lys Tyr Arg Asp Ile Leu Gln Lys Asp Asn Met Leu Val Gln<br>975                       980                         985 | 39352 |
| aga aca agt aac ttg gaa cac ctg gag gtaagtttgt gtgattcttg<br>Arg Thr Ser Asn Leu Glu His Leu Glu<br>990                     995 | 39399 |
| aaccttgtga aattagccat ttttcttcaa tattttgtg tttgggggga tttggcagat | 39459 |
| tttaattaaa gtttgcctgc atttatataa atttaacaga gatataatta tccatattat | 39519 |
| tcattcagtt tagttataaa tattttgttc ccacataaca cacacacaca cacacaatat | 39579 |
| attatctatt tatagtggct gaatgacttc tgaatgatta tctagatcat tctccttagg | 39639 |
| tcacttgcat gatttagctg aatcaaacct cttttaacca gacatctaag agaaaaagga | 39699 |
| gcatgaaaca ggtagaatat tgtaatcaaa ggagggaagc actcattaag tgcccatccc | 39759 |
| tttctcttac ccctgtaccc agaacaaact attctcccat ggtccctggc ttttgttcct | 39819 |
| tggaatggat gtagccaaca gtagctgaaa tattaagggc tcttcctgga ccatggatgc | 39879 |
| actctgtaaa ttctcatcat ttttattgt agaataaatg tagaatttta atgtagaata | 39939 |
| aatttattta atgtagaata aaaaataaaa aaactagagt agaatatcat aagttacaat | 39999 |
| ctgtgaatat ggaccagacc ctttgtagtt atcttacagc cacttgaact ctataccttt | 40059 |
| tactgaggac agaacaagct cctgatttgt tcatcttcct catcagaaat agaggcttat | 40119 |
| ggattttgga ttattcttat ctaagatcct ttcacaggag tagaataaga tctaattcta | 40179 |
| ttagctcaaa agcttttgct ggctcataga gacacattca gtaaatgaaa acgttgttct | 40239 |
| gagtagcttt caggattcct actaaattat gagtcatgtt tatcaatatt atttagaagt | 40299 |
| aatcataatc agtttgcttt ctgctgcttt tgccaaagag aggtgattat gttacttttt | 40359 |
| atagaaaatt atgcctattt agtgtggtga aatttatttt ttttccattc tccatgtcct | 40419 |
| ctgtcctatc ctctccagca ttagaaagtc ctaggcaaga gacatcttgt ggataatgta | 40479 |
| tcaatgagtg atgtttaacg ttatcatttt cccaaagagt attttcatc tttcctaaag | 40539 |
| atttttttt tttttttttg agatggagtt tcattctgtc acccaggctg agtgcagtgg | 40599 |
| cacgatctcg gcttaacgct tactgcatcc tctgcctccc agattcaagc agttctcctg | 40659 |
| cctcagcctc tgagtagctg ggattacagg tgtgcaccac cacaccagct aatttttttt | 40719 |
| tttttttttt tttttttgag gcagagtctc gctctgtcac ccaggctgga gtgcagtggc | 40779 |
| gccatcttgg ctcactgcaa gctccacctc ccgggttcag gccgttctcc tgcctcagcc | 40839 |
| tcctgagtag ctggtaccac aggcacccac catcatgccc ggctaatttt tgtatttt | 40899 |
| agtagagatg gggtttcacc ttgttagcca ggatggtgtc gatctcctga actcgtgatc | 40959 |
| cacccgcctc ggcctcctaa agtgctggga ttacagatgt gagccaccgc acctggcccc | 41019 |
| agttgtaatt gtgaatatct catacctatc cctattggca gtgtcttagt tttatttttt | 41079 |
| attatcttta ttgtggcagc cattattcct gtctctatct ccagtcttac atcctcctta | 41139 |
| ctgccacaag aatgatcatt ctaaacatga atcctaccct gtgactccca tgtgactccc | 41199 |
| cgccttaaaa actgtcaaaa gctaccggtt acctgaaggg taaaagtcaa gtcccctact | 41259 |
| tacctcatgt catctagagc aagagatgaa ctagctgagt tttctgacca cagtgttctt | 41319 |
| tcttatgtat gttcttttgt acgtgctctt ttctatatat agggaaccat ttctctcttc | 41379 |

```
cagttgtttt gctcagtgaa tttctattcc tgtttcaaaa cttgttcagg cattacctttt   41439 tttttcttaa gcatacttttt tttaatggaa caaagtcact cctgtctaca ctagttctgc   41499
atcttataca taggttttgt acatagtaca tatttatatc acatcaaatt atatgtgttt   41559
acatatctgt cttccttaat ggaatataag tcttttgata taaggaacta tttaatttgt   41619
ttctgtgtgt tgagtatctc ctgtttggca cagagttcaa gctaatacat gagagtgatt   41679
agtggtggag agccacagtg catgtggtgt caaatatggt gcttaggaaa ttattgttgc   41739
tttttgagag gtaaaggttc atgagactag aggtcacgaa aatcagattt catgtgtgaa   41799
gaatggaata dataataagg aaatacaaaa actggatggg taataaagca aaagaaaaac   41859
ttgaaatttg atagtagaag aaaaaagaaa tagatgtaga ttgaggtaga atcaagaaga   41919 ggattcttttt tttgttgttt tttttttttga aacagagtct cactgtgttg cccaggctgg   41979
agtgcagtgg agtgatcttg gcttactgca acctctgcct cccaggttca gcgattctt    42039 ctgcttcagt ctcccgagta gctggaatta caggtgccca ccagcacggc cggctaattt   42099
agtagagaca gggttttgcc atgttggccg ggctggtctc aaactttgga tctcaggtaa   42159
tccgccagcc tcaacttccc aaagtgctgg gattacaggc atgagccact gtgcccagcc   42219 tgttttttttt ttttaaagg agaccagtga gtttcagga ggagggaaag aaaatttaga   42279
gttactaggg agagagtgat gaagataaga gatgaaagtg gtaataaggg aaatagcaaa   42339
atatcagggt aggtgggaga aaaagagatt tgtaacaaac aataggatta tcctgtgaaa   42399
aaggatgaaa ggaagaaaaa aatggataga aagatattta aaacaccctc agcctcctgt   42459
tttccctcct gtgtattcat agtatataaa actataatta tgtactttac ttaaaaaata   42519
tattattatt accttatcgt gcttatttaa tcatagcatg tcctcttttt agtctcatta   42579
ccctgtttgt attattcttc ataacactta atacctgaca ttgtattata tattggctta   42639
ttttccaggt actccactca aatataagtt ctaggatata atttatttat cactgaaatc   42699
cattgcttag agtacctggc atgtagtaaa taggcattct gttttttcaa ataaaaaata   42759
aaggaactta agatatatat ttatgttata tcgccagcct ttttcctcac agctctattc   42819
tgttgtacag aattacctac tttacaattc ctgtgtttca aggggatctc aaatttaacg   42879
tgtccacaat gaactcctga tttctgtttc tctcctagtc attcttattt caatatatgt   42939
tcagttacct aaccagctag tcaaggcaga tactttagag ttattctgta gtcattcttt   42999
ttccctacca ttttttgtttt ccaaatgtaa tttatgtgtg tcttcttcat cctcgcagct   43059
ctaacccttg tccaaaccag catcatcact catctggagt tccacaatgt ctttctggct   43119
agtttccctg atttctctat tgacccctttt attctccaca gtgcagccag aatgattgtt   43179
taaaacttcc tccttaaaat cttaaattg ttttctttta tcgttaagt taaattccag   43239 ttccttgtct tggcatgcca tgccctgcct ggtgtggccc ctgatggtct ctccaacttc   43299
atgttttact actattgact cttatttttg cttactctgc ttgggtgctc cagtcctcca   43359
aatcatttcc tgctccaatc atttcaatca tttttttcctc tcagatctta tagtattcca   43419
aatgctttct tcctttggag catctggggt tactaataaa tacttcgtac ctcacagttc   43479
agcttaaata tcaattattt ggtggttaag acatccttca accgctctat ctaaatgttc   43539 cttttctatta ttcactggct cagtactctg ttttatttt cttctaaat gtcaacttt    43599 ttttttttga gtcagggtct cactgttgcc caggctcgag tgcagttgca caatcatagc   43659
tcattgcagc cttgccctcc tgggatcaag taattctccc acctcagcct ccaaaatagc   43719
tgggattaca ggtatgcatc accatgctca gctaatttttt tgtgtttttt tgtagagatg   43779
```

```
aggtctcact tgttgccca ggctggtctc aaactcctgg actcaagtga ttctcccacc   43839
tcagcctccc aaagtgctgg ggttacaggt gtgagccact gcacctggtc gatactgact   43899
tttttttttt tttgagatgg agttttgctc tgttgcccag gctagagcgc agtggtgtga   43959
tctcagctca ctgcaacctc cacctcccag gttaaaggga ttcttctgcc tcagtctcct   44019
gagtagctgg gattacaggc aagtgccatc atgactggct aattttttgta ttttttagcac  44079
tatgtttagt actgtgttgg ccaggcttgt ctcgaactcc tgacctcaag tgatccaccc   44139
acctcagcct cccaaagtgc tgggattaca ggtgtgagcc accgtaatcg ccaacattg    44199
acattttag tagacttttt gtttgtttac ttgcttatta tctgctgcct tccacactct    44259
ggcgaaatcc tgccacccac ccacacacac ataggcactg aatgggcaga actctgaagg   44319
ccagaatttt atatttcttt tcactgtaaa catcatcatc tgtcactgat ggcacactag   44379
gatgctcagc aactgtgtgc atgaaggaag taagcactag tttgtgaagg ctgcaaaact   44439
cttgagtatt ctaagagttt tggccaaaat gaatgtacag ctttagtggc agaagctaat   44499
actcagaaat tgaggccgta tattggataa cacaggattt ggatgattat tttaaaataa   44559
tattttacat tgtatatatg tgtgtgtgtg tgtgtgtg tgtgtgtatg tgtgtgtgtg   44619
tgtatatata tatgtatgta tgtgtattag tccgttctca tgctgctatg aagaaatacc   44679
tgagactggg taatttataa aggaaagagg tttaattgac tcacagttcc acagagctgg   44739
ggaggcctca gaaaacttaa cagttatggc agaagggaa gcaaacacat ttttcttcac    44799
atggtggccg gaattagaag aatgtgagcc gagcaaaggg gaaagcccct tataaaacca   44859
tcagacatcg tgagaactta ctattatgag aatagcgtgg gggaaaccac ccccacgatt   44919
caattacctc ccaccaaatc cctcccatga catatgagga ttatgggaac tatgattcaa   44979
gatgagattt gggtagggac acagccaaac catatcagta tgtatatgta tacaagtatt   45039
atatatatat gtatgtgttt gtatgcatac atgtattata tatggaggaa attctaattt   45099
tgtaaaaaac tggattgtga gttttaagga gatgttatat aaagttaaga caatgtcatt   45159
ttgtggtatt ggtctgaatt acaatgtagt ttcttagtga tattttttcct ttattcag    45217 tgt gaa aac atc tcc tta aaa gaa  caa gtg gag tct ata aat aaa        45262
Cys Glu Asn Ile Ser Leu Lys Glu  Gln Val Glu Ser Ile Asn Lys
        1000                1005                 1010 gaa ctg gag att acc aag gaa aaa  ctt cac act att gaa  caa gcc       45307
Glu Leu Glu Ile Thr Lys Glu Lys  Leu His Thr Ile Glu  Gln Ala
    1015                  1020                   1025 tgg gaa cag gaa act aaa tta g gtaagtttta tgactctgat aatataaaat      45359
Trp Glu Gln Glu Thr Lys Leu
        1030 gattaacatc taataatgaa tatttcttat ttaaagttcc ttttttatgc tagattaaaa   45419
ggaagtattt tgactaaaaa aagaaagaac tttctgccta ataatttaac ttaggcagat   45479
gaataatcct gtacttaacc ccaccaaagt ttagttttca gtcctaagt tagatttgtt    45539
tctaatgaaa tcatatatgt taaaaattta tgactaagta ttagctactt tgaaccgttt   45599
aacaattaaa actgatgata ttttattaat ggtattatga gttctttcac tgagtgcaag   45659
ttatattagt tatatatcac ttgatatttt taaattaaaa gataccagga aacagcaaag   45719
aaaatgtgaa aagaagttgt atttctcata gttttactac tatattactg tatattttg    45779
ctcctatatg cttacatatt ttatatattt taaattatta taaacatggt tttatactgt   45839
atttagatag taatatcaaa aatattttta tggccggcgc agtggctcac acctgtaatt   45899
```

```
ccagcacttg ggaggctgag gagagcagat cccctggggt caggagttcg agaccagcct   45959
ggccaacatg gcaaaacccc atctctacta aaagtacaaa aattagccag gcgtggtggc   46019
agttgcctgt aattccatct actcaggagg ctgaggcagg agaattgctt gaacctagga   46079
gtcagaggtt gcagtgagcc aagatcatac cacagcactc cagcctaggc gataagagtg   46139
agactccgtc tcaaaaaaaa aaaaaaattt gttttattca tcatacttat aaatacttat   46199
acaatagcct aatgtgtttg agtgattaaa tcactagctt tttatatttt tgctattgct   46259
tatagtgcca cagtgaacat tttcatgtat atctaacaga gatattactg tctcagaagg   46319
tattgaaatc tttgttgctc tcattagagt tttccatatt aattttcaa acagttatat    46379
agtttataag attttcataa ttttatctca tatattgtgc ttcataattt tcaaataaat   46439
ttgctgcttt cgataatgta ttttcatgta tttgtttcct agacgttaga gctattcaag   46499
gttttttatta ctaaatagag ctgttctctt aaattggtaa tgagatactt ggtttagaga  46559
agcctaacac tgggaaatct tacataagct actttttagaa atgtaatttt tagctcaata  46619
agagattaaa tatgaattga cttttgtgta gtatttgcat ggaagaaggt accatttaaa   46679
tgaagacatg agagtattac gtacaatttt agtaggttct ttttatttta tcatctttat   46739
ttttaataaa tgctgaattc cctacagaaa ttctttaatt tttacatatc ttgatctctt   46799
tcatatatgg atttatatca ccgaagtttt aagagtgttt ccctattccc tgttgcccctt  46859
atatctttgt ttaaaaatgt cacatcatta gcttttttc atctaggaat ttgttagtgt    46919
tgggctgttg tgctctaccc tctctttaag aaaactccaa acccaaaaac atacaagatg   46979
gctagtctgc ttcagccttt gtgatgtgct tttctcttct aatcagagtt tagcacaata   47039
cagaatggag aaggactcct ttatatattg gtatttattg cagtattttt ctacatggtg   47099
cctaaggtta cttgaatgag tctttattcc ataatgaact gatttactaa tgcttttagc   47159
acctgttagt gatccattat tgttagttac ttgattactg cttgccacag ctattctaaa   47219
ataatacatt ttaaagataa atacagaaca taatgaagta ctttttaaaa ctgagatagaa  47279
gaccaatttt tttttcagga aatgtatatt actttgagaa aactcagtta taaaacttga   47339
acttatgaag ctggaaaaac aggagggggc attattggta ttgtaaaagg ctgtttacaa   47399
agtgagttgc tgcttagttc cttttaagtaa ttggctaccc taaacacatc agttttaagt  47459
tgctgaaaag caaaacactc taccaaattt tgttttttttt ctagaccatg tttacaaagc  47519
aaaagtatgt tttcttcccc cccctcaaa aaatgactaa tgacactcct atgcgatgcc    47579
tttttatggt aaattgaggc ttttagttct cttttccattt agccacagac ttttgtgtcc  47639
aaagacaagc tgcgtaactg catatataag gttaaggcat aactactaat aaaagaatgt   47699
aaaatatttg atattaggtc tgtacaaaga ccaaataata ctcatgatta gacaagatta   47759
tatttggtag aatctatcca tcatatggct tcagatttta cttttcagct tggctttgtg   47819
agactttaaa aatcaagtca ttgcacttat attcacaaag tcacattgct ttactgcatt   47879
gcttctcata cagtttatct cctttcagta aaatgtttac ttgccatttt taaaatttct   47939
tatatgtgac acttctacac taagtccttt atgttgttag ttccacaatt ctgtgaggaa   47999
taggtttttt tttttaatca tttgattgat gaagaacatt aagttccaca gagattaaat   48059
ggtacaggca tcacacaggc aggaagtaac agagctaaga ttagagtcca ggtctgatgg   48119
aattcagaaa gctaatgtgc tttccatgga actataatgc tttctaatat acagcatcta   48179
aaatatctga ggtaatttta atataaacag catgagatta acttaaatat tattgcatgt   48239
       ag gt    aat gaa tct agc atg  gat aag gca aag aaa  tca ata acc aac   48285
```

```
       Gly Asn Glu Ser Ser Met Asp Lys Ala Lys Lys Ser Ile Thr Asn
       1035                1040                1045 agt gac att gtt tcc att tca aaa aaa ata act atg ctg gaa atg      48330
Ser Asp Ile Val Ser Ile Ser Lys Lys Ile Thr Met Leu Glu Met
1050                1055                1060 aag gaa tta aat gaa agg cag cgg gct gaa cat tgt caa aaa atg      48375
Lys Glu Leu Asn Glu Arg Gln Arg Ala Glu His Cys Gln Lys Met
1065                1070                1075 tat gaa cac tta cgg act tcg tta aag caa atg gag gaa cgt aat      48420
Tyr Glu His Leu Arg Thr Ser Leu Lys Gln Met Glu Glu Arg Asn
1080                1085                1090 ttt gaa ttg gaa acc aaa ttt gct gag gtttgatatt ataagtttta        48467
Phe Glu Leu Glu Thr Lys Phe Ala Glu
1095                1100 tcatacaatt atagaataaa gaattagttt tggtagacat tgtattattg ttaagtggtt 48527
tgtctggatc tctgaaatat cttattaata tagtgcctat gttttgtgta ataaataaat 48587
aaaagattta aatctgaatt gtttaaaagg aaagcagata tttctgtaag tttttctcac 48647
caatgttata ttattagatt taatttatga aatgttattt actaaacaat ggaattgcct 48707
ttcaccacca tcccttcatt taacaaatat ttattcattg cctattacat gtcagaccct 48767
gtgttgggac tggcagtata gcaagaaaca aaatagacaa taatctctac tttcagggac 48827
tttacattct aattggtggt tttatatatt tttgatgtgg tcagaatcat taaactgtgt 48887
ggcagtaaat atagtttgca agtatttaac aatttatgat taaacacaac tcttacagtg 48947
tttgcttacc ttgagattta atatattttc aaagcattta tatcatttt gttttaacta 49007
tgtcactaaa tctatatgag taagatttta ttaactcatt tggattatt tatagatgat 49067
acaattgaag taaatataaa tgagcagatt gcattctaag caaagtaaga atattgcaag 49127
ttcagatatt attagataat gagttgccta ataaaaatga cttttggtgg attggaatat 49187
aaccagagtt tccatagttt gtttctgatt cttttcatatt ttttaccctc cttcagtctg 49247
ttcttaacac ttcacactta atataatatg tgaactaagg ccaagtaaag aggattgcag 49307
tactttaaaa gctaaattac aaagaaaacc tcaccaaaaa ttgatgtatc tgaacatttt 49367
ttgttacatt tccttag ctt acc aaa atc aat ttg gat  gca cag aag gtg  49417
                Leu Thr Lys Ile Asn Leu Asp  Ala Gln Lys Val
                    1105                1110 gaa cag atg tta aga gat gaa tta gct gat agt gtg agc aag gca      49462
Glu Gln Met Leu Arg Asp Glu Leu Ala Asp Ser Val Ser Lys Ala
1115                1120                1125 gta agt gat gct gat agg caa cgg att cta gaa tta gag aag aat      49507
Val Ser Asp Ala Asp Arg Gln Arg Ile Leu Glu Leu Glu Lys Asn
1130                1135                1140 gaa atg gaa cta aaa gtt gaa gtg tca aa gtaagtgcat ataagcattt     49556
Glu Met Glu Leu Lys Val Glu Val Ser Lys
1145                1150 tagccatttg actagatgta tcttctttaa tttgtcttta agaaacccaa ttacaggtat 49616
acaattctta gtagtaattg atactgattt cttttttataa gaacaggatt aagtaatatt 49676
aagatcggtt ttaacagggt taaataataa tattgacgag aataaatttg ttaaagagga 49736
agtgacctct caagatttgc attttttaga gttcaggaat attattgcag aaaggtccag 49796
ttcctccaca tattgatttt ttggggaagg ggtgatggag gaggaatggt tgtttattgt 49856
atttaaactt aagtttcttc attttaataa gggagtaata gtacctcttc tacctgtttc 49916
ataaggttgc tgtaagaata taataaaaaa ttcagatttt gatttagttt acatttatcg 49976
```

```
ggcatctact atgtactagt cacggtgcaa ggtattaaac atatattgac ttgtacaatt    50036
atacttaacc ttgaggttat attttttgttt tcattttaca tgaagaaata tgcccagcta   50096
gtttagaaca caaaatatat ataaggagta aatactgcgt gctggctggg cgtggtgaca    50156
tgtgcctgta gccccagcta ctcgggaggc agaggcagga gaatcgcttg atcccgggag    50216
gtggaggttg cagtgagccg agatcgcgcc actgcactcc tgcctggtga cagagcgaga    50276
ctctgtcaaa caaacaaaca aacaaagaaa aacaaaacaa aaaaaccgtg tgccagctat    50336
atgctgtatt ttcattctct tttgtaatta ggtgatattt cagtagaaaa gtataaggag    50396
cacttagtta atctgtcaag cataaatagt aaaaatattt tatggcctac tcataaaaat    50456
ataaccattc ctttggagcc ttgatagttc tcttgggaat atcagttttt gacatctttt    50516
tcactatgaa agacccctttt ttttaaaaaa attgatcctt tcttctcatg gacctctttt    50576
gatataaact aacttataat agttcatttt aatcatattt tgttaatcat gcaactggca    50636
atgagagcct ctcatcagta tgaggaaacc tgccttatct ataatactga actaaaatta    50696
ttctaaccca aagcaaagaa actttacatt ttgctttgcc tgtattagct tatcacagta    50756
ttcatgaggg aatttgaagg acttattacc attaggctat ctctttttttt ttttttttgt    50816
aattttatta atgcatgtt ttgtttcttt tcacattact gataacttgt agattaaaac     50876
aaatcaaaac atgcattaat ccatctaagg atcctagaaa ttttacattt ctgtgttctt    50936
aactgtgtga tggtcttaga taaatgtact aaataccta tcctagcata ttccaaatta     50996
tgacaataaa tgttttatgg aaaaaagtat gggaacagaa gttctttggc tatatacatt    51056
tggaaaatac tatatagtaa gtatgatttg agataattat atatgataga acctctggga    51116
gcactgaata tatgttagga atattcaaga gggaggaggg atgttgagaa tgaagttttt    51176
tttatatagc aaacatgata acctctgatg gaattatgtt tcatgaaaca gtttaggaaa    51236
tcctgttttta atatttcata caaagaagag atagatgctg aaaacgaatg gcttttgaa    51296
aaagggtcta gaaattttga attttggcat ttacttagaa agtgtactta attgttcctg    51356
aaataccta tcatttccta g a ctg aga gag att tct gat att gcc aga         51405
                         Leu Arg Glu Ile Ser Asp Ile Ala Arg
                         1155                   1160 aga caa gtt gaa att ttg aat gca caa caa caa tct agg gac aag          51450
Arg Gln Val Glu Ile Leu Asn Ala Gln Gln Gln Ser Arg Asp Lys
    1165                1170                1175 gaa gta gag tcc ctc aga atg caa ctg cta gac tat cag gtatgtgcag       51499
Glu Val Glu Ser Leu Arg Met Gln Leu Leu Asp Tyr Gln
1180            1185                1190 tattggctct tctacataga atccactttt ttccctaaat ttacattaga tgttgggagt    51559
gggatatgtt atactttttg tttgtttcga gatagggtct cattctgttg cccagggtgg    51619
agtgcagtgg tacattcaag gctcattgca gccttcacca cctgggttca ggtgatcctc    51679
ccacctcagc ctcttagaca gctgggacta caggcacgtg ccaccacacc taatttttttt   51739
gcatttttttg tagagacagg gtttcaccat gttgcctagg ctggtcccaa actcctgggt    51799
taaaatgatc tgcccacctt gacttcccag aatgctggga ttacaggtat gagccaccat    51859
gctgggccat tgttacattt ttaatcaaaa gatataccaa ccagaggctg ttattcttgt    51919
tagttggaac ctgattagaa agctctttaa tttgaaatat tgttcagtaa tccagtacag    51979
catttaaatg cctatagatg aattatgctg ctgatcaaaa ttaggacact gagaattgta    52039
gttagtaaat ctttaataac aatatttttct cttgtattta tatgtaactt tttacatatt   52099
cttacgttat atatgttggg aattataaaa acatacacat tgtcctgatc agtattatgt    52159
```

-continued

```
tacttgcaat ggaggttaaa aaaaaactgt aacagtcagg catggtggct cacgcctgta    52219
atcccagcac tctgggaggc cgaggcaggc ggatcacgag gtcaggagtt cgagaccagc    52279
ctgaccaata tggtgaaacc ccgtccctac taaaaataca aaagttagcc aggcgtggtg    52339
gcatgtgcct gtaatcccag ctacccagga ggctgaggca ggagaattgc ttgaacccgg    52399
gaggtggagg ttgcagtgag ccaaaatcac gccattgcac tccagcttgg gtgacagagt    52459
gaaactctgt ctcaaaaaaa aaaaaaaaaa acaccagtaa catacccact gttattcagt    52519
tacatttgga tttttaagttt gtttgattct aggttttttc ttttacagtt ctttggtaat    52579
tatttgtatt aaagcaaagt tacatttttg tagatctcat gtgccactgt gttaaaactt    52639
tgcttagtaa attgtgaatt ttaaatctgt gataactttc actggaaaaa tttgaaactt    52699
actacaaata tattttttt ttaatatcag gca cag tct gat  gaa aag tcg ctc    52753
                                Ala Gln Ser Asp  Glu Lys Ser Leu
                                                 1195
```

| att gcc aag ttg cac caa cat aat gtc tct ctt caa ctg agt gag | 52798 |
|---|---|
| Ile Ala Lys Leu His Gln His Asn Val Ser Leu Gln Leu Ser Glu | |
| 1200             1205                 1210 | |

| gct act gct ctt ggt aag ttg gag tca att aca tct aaa ctg cag | 52843 |
|---|---|
| Ala Thr Ala Leu Gly Lys Leu Glu Ser Ile Thr Ser Lys Leu Gln | |
| 1215             1220                 1225 | |

| aag atg gag gcc tac aac ttg cgc tta gag cag aaa ctt gat gaa | 52888 |
|---|---|
| Lys Met Glu Ala Tyr Asn Leu Arg Leu Glu Gln Lys Leu Asp Glu | |
| 1230             1235                 1240 | |

| aaa gaa cag gct ctc tat tat gct cgt ttg gag gga aga aac aga | 52933 |
|---|---|
| Lys Glu Gln Ala Leu Tyr Tyr Ala Arg Leu Glu Gly Arg Asn Arg | |
| 1245             1250                 1255 | |

| gca aaa cat ctg cgc caa aca att cag tct cta cga cga cag ttt | 52978 |
|---|---|
| Ala Lys His Leu Arg Gln Thr Ile Gln Ser Leu Arg Arg Gln Phe | |
| 1260             1265                 1270 | |

| agt gga gct tta ccc ttg gca caa cag gaa aag ttc tcc aaa aca | 53023 |
|---|---|
| Ser Gly Ala Leu Pro Leu Ala Gln Gln Glu Lys Phe Ser Lys Thr | |
| 1275             1280                 1285 | |

| atg att caa cta caa aat gac aaa ctt aag ata atg caa gaa atg | 53068 |
|---|---|
| Met Ile Gln Leu Gln Asn Asp Lys Leu Lys Ile Met Gln Glu Met | |
| 1290             1295                 1300 | |

| aaa aat tct caa caa gaa cat aga aat atg gag aac aaa aca ttg | 53113 |
|---|---|
| Lys Asn Ser Gln Gln Glu His Arg Asn Met Glu Asn Lys Thr Leu | |
| 1305             1310                 1315 | |

| gag atg gaa tta aaa tta aag ggc ctg gaa gag tta ata agc act | 53158 |
|---|---|
| Glu Met Glu Leu Lys Leu Lys Gly Leu Glu Glu Leu Ile Ser Thr | |
| 1320             1325                 1330 | |

| tta aag gat acc aaa gga gcc caa aag gtaaacattt aaacttgatt | 53205 |
|---|---|
| Leu Lys Asp Thr Lys Gly Ala Gln Lys | |
| 1335             1340 | |

```
tttttttta agagacagta tcttgatctg tttcccaggc tggagttcag tggtgcaaac    53265
atagctggaa ctcctgggct caagggactc tctagcctca gcctcctgag tagttgtagc    53325
tggcagtaca ggtgcacacc accataccta cctaattttt taaaattttt aaatttttt    53385 gtagagacaa ggtctcactt tgtcacccag gctggccttg aactcctggc ttcaagtaat    53445
cctcctgctt tggtctctca aaagtgctga gattacaggc atgagccact gtgcccagcc    53505
aattttaaat tcattatctt caaaagagtt acatgataat ttcttaatat atgcctatat    53565
gaaaaatgct taagatacaa attccaatta tgattcatta atttagattt tataacttag    53625
cagtgttggc tatttgaatg tctattatac gtaaaaataa aattaggctt ttctaaccaa    53685
```

-continued

```
agattttagt gggaatgttc agattgtata atagcaaaga attttaatta ctataggaaa   53745
atttatatta attaaacact aattattata tttaaacatt gtagtagtta tcagttgatt   53805
tctactgttc ataattatct ttgatctaca agtagtgggc ccacatttac ttttaatatg   53865
gtttaatctt catttagaaa gaattaaatg aaaataatt atcttgcaac tacatcctgt    53925
tctctaggct agaaacattt aggatttctg tttttgaaag taataccaaa gttccaatga   53985
cctgcttata gtcagtgttc aataaacgta taacaaatga aagtgaatat tagtgatgtc   54045
cattccaaca taatttgaag attttttattg taaaatccca catatttgta gaaaagtcta  54105
tggaaatcct aaataagatt ttgtcatgta gtttgacaaa agataacatt gtgtcttatt   54165 ttatttttaga atggccatta ctttcaatta aaatcattat catcaatgga ggaatgttat  54225
ttgttaatat agcatttata tttgtgtata taaattgtaa atcttag gta atc aac     54281
                                                    Val Ile Asn
                                                          1345 tgg cat atg aaa ata gaa gaa ctt cgt ctt caa gaa ctt aaa cta         54326
Trp His Met Lys Ile Glu Glu Leu Arg Leu Gln Glu Leu Lys Leu
        1350                1355                1360 aat cgg gaa tta gtc aag gat aaa gaa gaa ata aaa tat ttg aat         54371
Asn Arg Glu Leu Val Lys Asp Lys Glu Glu Ile Lys Tyr Leu Asn
        1365                1370                1375 aac ata att tct gaa tat gaa cgt aca atc agc agt ctt gaa gaa         54416
Asn Ile Ile Ser Glu Tyr Glu Arg Thr Ile Ser Ser Leu Glu Glu
        1380                1385                1390 gaa att gtg caa cag aac aag gttttatttt atatttattt cattttttc         54467
Glu Ile Val Gln Gln Asn Lys
        1395 cctaagtttt ttttttttt ttttttttt gagatggagt ctcactctgt cgcccagact     54527 ggagtgcagt ggcgtgatct cggctcactg caagctctgc ctcccgggtt catgccattc   54587 tcctgcctca gcctcccaag tagctgggac tacaggcacc cgccaccgtg cctggctaat   54647 ttttttgtatt tttagtagag acggggtttc accatattag ccaggatggt cttgatctcc  54707 tgacctcatg atccgcccgc ctcggcctcc caaagtgctg ggattacagg cgtgagcccc   54767 taagatttta aacaagaata ttgcacaaat gactatgtta tccttctaat taagtgcacc   54827 ttccattact aattgattat ataataattt gttttttattt ttctaaacta ttctaaaaat  54887 tcatatttat ttagctttta taacagtagt cttaatctta aaaacggcaa tacataagca   54947 acctcatttg gtaagttaat ttttattttg atattggtta tttgactttt cacagttcca   55007 cgtttctact ggctctcact gatagagtaa gaagtcagct tcttatagaa taaagtatat   55067 acttcagaga cagatgaaat tcgtcaaaca tatgactgtc tcagagattg ttccccctgc   55127 ttaaattgtt cttaccctag atacctttgg tatttacact gtcagtgcct gcaggtctta   55187 gctcaaatgt cttaccttat cagtgtatcc ttcaccagcc acctaatata caacagtaaa   55247 tcctactatc cagattccta aatagagatt aattaactta attttctcc aaagtgcttg    55307 taaccttctg acgtattaca tacttactgg tttattattg actgtctttc cttcgccaga   55367 atgcaagttc cgtggtgaca cggacttggt tttgtttact gccatgtttg tatttcctag   55427 aatgatgctt ggcacataat atatgtcatc aaatatcttt cgtatagctg aacggatgga   55487 tggatggatg gatggatgga tggatagact gaaatcctta cttcacatct gcctttgtga   55547 tcttacacaa gttacttcac ctctctgagt ttgtattttt ttccataaaa ggaaaataat   55607 tacagtttct tcaatgtgtt gtgaggatta gataagaaaa tatatataaa atgcctgtta   55667 tgtgcctgat gtcttcgtgt atgtgtctga cacaaattgt cctttttta g ttt cat    55724
```

|  |  |
|---|---|
|                                                                      Phe His<br>                                                                        1400 |  |
| gaa gaa aga caa atg gcc tgg gat caa aga gaa gtt gac ctg gaa<br>Glu Glu Arg Gln Met Ala Trp Asp Gln Arg Glu Val Asp Leu Glu<br>                    1405                         1410                       1415 | 55769 |
| cgc caa cta gac att ttt gac cgt cag caa aat gaa ata cta aat<br>Arg Gln Leu Asp Ile Phe Asp Arg Gln Gln Asn Glu Ile Leu Asn<br>                    1420                         1425                       1430 | 55814 |
| gcg gca caa aag gtatgaatga ttaatcttgt tgttactct gtagcatagt<br>Ala Ala Gln Lys | 55866 |
| ctagagtgtt aactcacaga aatatttcct gtatcagatg taattttaat tgatgttata | 55926 |
| ttgtatattt aaaatataag aggggtttaa tctatgtttt atcatacagc tgtaaaaatt | 55986 |
| aatagttact ctcaatgctg caactgcttt tttaaaaaac atactatttc ttaatag | 56043 |
| ttt gaa gaa gct aca gga tca atc cct gac cct agt ttg ccc ctt<br>Phe Glu Glu Ala Thr Gly Ser Ile Pro Asp Pro Ser Leu Pro Leu<br>1435                       1440                       1445 | 56088 |
| cca aat caa ctt gag atc gct cta agg aaa att aag gag aac att<br>Pro Asn Gln Leu Glu Ile Ala Leu Arg Lys Ile Lys Glu Asn Ile<br>1450                       1455                       1460 | 56133 |
| cga ata att cta gaa aca cgg gca act tgc aaa tca cta gaa gag<br>Arg Ile Ile Leu Glu Thr Arg Ala Thr Cys Lys Ser Leu Glu Glu<br>1465                       1470                       1475 | 56178 |
| gtaattagaa gaatttgcat tttgattagt gtattatttg gtatgtttgg ggggctttct | 56238 |
| aaataatatt tctttatgag ggcaatgcat agaatgatga atctattgct aatttcacta | 56298 |
| tttttctatt ctcctataat gtttctaata gccaataatg aacagcagat atagttaatt | 56358 |
| tgaattcact atttaattat tagttggtac ctttcggtac actgaatatg aaaggaaata | 56418 |
| aaaagcattt aattgtagtt ctatgagcaa tatattctct tatatgatct ctttattctt | 56478 |
| acttttttgg ttttatttg aagtgcatgt tacataatct atgaatcaat tttcagttca | 56538 |
| ttgcctttaa tgcatggtta aagggttgaa ggtaaattag aaattacttt ctgttttaac | 56598 |
| ctagatcttg aatttgatta gtaggtgatc aaatctgtca tcttcattaa attattcaga | 56658 |
| aaataatgta aactgaatgt gttttcattt tagttttcat ctaaataaac tgcaaataca | 56718 |
| tttaaaatat acataaagaa gttttcaag taaaactgta cattttaat catttcagga | 56778 |
| aacgtagatt tcttcagta attttaagat ttgtcattta tgtgaattgc cattgaatta | 56838 |
| cttaatttaa aatactcacc ttaatcctct tgaagagtaa aaattttct gttttttct | 56898 |
| ctttgtttta ataagctgcg gattttatat tcgtaattta ttgagttggg cctctaaaat | 56958 |
| tccagttttg tacttaactg acttatagat tagtctccta atgctctgct agtcaatgga | 57018 |
| ccaaaataaa agaaataatt tattacatat tcttcctaaa tctagtacca ccatacatgt | 57078 |
| ataattctaa actgtaatat ctcaataaag taccttaatt aaatttatg ttcatcataa | 57138 |
| caatgaagtt tctagcatat gtaatagtct tataaataag catgcaaata actgctgtca | 57198 |
| attagaatta gtcagtttaa ccttattaag tatcaaatgg ctattgtaca tatgatgtga | 57258 |
| aaaataaagt gaattttttt tggctaataa ctaatctaaa attcagatga agcattttaa | 57318 |
| agggaaaaag atactttaat gatttattat aatttaatca ttgcag aaa    cta aaa<br>                                                                      Lys    Leu Lys<br>                                                                                1480 | 57373 |
| gag aaa gaa tct gct tta agg tta gca gaa caa aat ata ctg tca<br>Glu Lys Glu Ser Ala Leu Arg Leu Ala Glu Gln Asn Ile Leu Ser<br>                    1485                         1490                       1495 | 57418 |
| aga gac aaa gta atc aat gaa ctg agg ctt cga ttg cct gcc act | 57463 |

```
Arg Asp Lys  Val Ile Asn  Glu Leu Arg  Leu Arg Leu  Pro Ala Thr
        1500              1505             1510 gca gaa aga  gaa aag ctc  ata gct gag  cta ggc aga  aaa gag atg        57508
Ala Glu Arg  Glu Lys Leu  Ile Ala Glu  Leu Gly Arg  Lys Glu Met
        1515             1520             1525 gaa cca aaa  tct cac cac  aca ttg aaa  att gct cat  caa acc att        57553
Glu Pro Lys  Ser His His  Thr Leu Lys  Ile Ala His  Gln Thr Ile
        1530             1535             1540 gca aac atg  caa gca agg  tta aat caa  aaa gaa gaa  gta tta aag        57598
Ala Asn Met  Gln Ala Arg  Leu Asn Gln  Lys Glu Glu  Val Leu Lys
        1545             1550             1555 aag tat caa  cgt ctt cta  gaa aaa gcc  aga gag gtattttatt              57641
Lys Tyr Gln  Arg Leu Leu  Glu Lys Ala  Arg Glu
        1560             1565 atattatgag ttatgctgtt atccattagt tttttaagc aaatgctaaa tattatttta      57701
ccctaaagtg gtatttcttt tcttgctttc aaatgattct atttaagaat tgttacttgc     57761
atgtgattgg attacacctc tgtcagtaaa actggaagtt tgtgtacatg tatctttcta     57821
ttatacactg actaaaccac gagtagctat catggtgaaa tcatatgatt ttgaaaaata     57881
ttttaattga gttataggt gaggattgag gcaataggt ggaatgaaat atatcacacc       57941
ggtaatcagt agaaatcaga tttgttagaa cttcgtgggg gaaagctaac atttaatttt     58001
ttctagaagt aagttaaaag atgatagata catgtcattc taatgttaag aataaattat     58061
gaactgaggc tgggcttgtc aacttgaaca ttgtctgagg gacatgcat accagtctag      58121 atacatacat atatggagat actgtttctt cctcatctca aaggaatttt agaagattga     58181
agagaaaata tataaggtct tcaaaatgtg aatttgtttt aatcacaatt taagatatag    58241
tttcgatttt ctgtaaaaca g gag caa  aga gaa att  gtg aag aaa  cat gag    58292
                       Glu Gln  Arg Glu Ile  Val Lys Lys  His Glu
                              1570             1575 gaa gac  ctt cat att  ctt cat  cac aga tta  gaa cta  cag gct gat      58337
Glu Asp  Leu His Ile  Leu His  His Arg Leu  Glu Leu  Gln Ala Asp
    1580             1585                            1590 agt tca  cta aat aaa  ttc aaa  caa acg gct  tgg gtaagattct            58380
Ser Ser  Leu Asn Lys  Phe Lys  Gln Thr Ala  Trp
    1595             1600 aagaactttg ttccattctt tattgattt tgtgaccatg taaattaaaa ttcagctctc     58440 ttctttttg gaatggaagt tacccttttt ggttgccaaaa taatcttctg aaaacatagc    58500
tctgatcatt cttcctcctg tagctcaccg ctgttcacaa aattatattt ataattctta    58560
gccatgtact caatctgcta tgaacctacc tgcctttctt ttcaaattct actcactgtg    58620
agtttagcta tatctaactt ccagaattca gctcatattt gcctctttg accattctgt    58680 tccatatgta tgaaatgaca tgtctttcat cttttaatgt gtaacttag catatttgag    58740 cattacctcg ttaattcggt caacacttat tgatctcctg ctacgtgcag acattttgct   58800
agctattgta aatacaaata ataaagtctg catttcctgt cttctttaag ccttcattgc   58860
ctattaaatc attcatttt agattagata ttatatttttg atcatttgag gaaccaaatt  58920
aaaaatatgg aataagtatg gcattgaatt atacatgcct attgctaata tattcatatt   58980 ttatag gat  tta atg aaa  cag tct  ccc act cca  gtt cct  acc aac aag  59028
       Asp  Leu Met Lys  Gln Ser  Pro Thr Pro  Val Pro  Thr Asn Lys
            1605             1610             1615 cat ttt  att cgt ctg  gct gag  atg gaa cag  aca gta  gca gaa caa      59073
His Phe  Ile Arg Leu  Ala Glu  Met Glu Gln  Thr Val  Ala Glu Gln
    1620             1625             1630
```

| | |
|---|---|
| gat gac tct ctt tcc tca ctc ttg gtc aaa cta aag aaa gta tca<br>Asp Asp Ser Leu Ser Ser Leu Leu Val Lys Leu Lys Lys Val Ser<br>1635                         1640                        1645 | 59118 |
| caa gat ttg gag aga caa aga gaa atc act gaa tta aaa gta aaa<br>Gln Asp Leu Glu Arg Gln Arg Glu Ile Thr Glu Leu Lys Val Lys<br>     1650                       1655                       1660 | 59163 |
| gaa ttt gaa aat atc aaa tta ca gtaagtcttc gaaatgtatt<br>Glu Phe Glu Asn Ile Lys Leu Gln<br>1665                       1670 | 59206 |
| gtaaaaatag gcaaatgata agtgatataa tgaagataaa cataagtgtt tgctatgcca | 59266 |
| ggcactgttc taagactttt aagtatattg tctcattttt atcctcagga ctgctggtta | 59326 |
| catatgttat cattttcccc attttaaaga gaggatatgg cctcaggaat gcttaatagc | 59386 |
| atgtctgggg gtagatggga aagccataat ttgaaactag tcagtctgac tcaaaagcca | 59446 |
| atacaaattc ttttccagaa tctcattttt accttctttg agcctcagtt tcatcttatt | 59506 |
| tatttatttt tattttgag acaaggtctg gctctatttc ctaggctgga gtgcagtgac | 59566 |
| ataatctcag ctcactgcaa ccttgacctt ccaggctcaa accatcttcc cacctcagcc | 59626 |
| tgcagagtag ctggcactac aggcaggtgc caccacacct gggtagtttt tttgtatttt | 59686 |
| tgtagagaca aggtttctcc atgttgccca ggctggtctt gaactcgtga gctcaagtga | 59746 |
| tccgcccact tcggcctccc aaagtgctgg gattacaggc ctgagccatt gcacccagcc | 59806 |
| tcatcatctt taaaatggaa ataataatac ttaccctggc cctttcaggg tggttatatg | 59866 |
| aaggtcaaat tataccgtgt atgaaagtaa tttgaaaact gtaaaataac atacagatag | 59926 |
| aaaactttg attacacact tataagagtg tctgtcatat aatagagatt ctaaacattg | 59986 |
| ttcaaccact ttatcagaac gtagatttta aactcaaaat aggtttatag ttaggtagtt | 60046 |
| tctaatcatt ataatattat ctctatgggc ctaaatttta ttatctgaaa aaacatgaga | 60106 |
| aaattgaact gcttgactta taattccatt tcagctctca agccctgct agagtctttg | 60166 |
| attctttact cacttattca aatgcctctg acagaattaa cactattttt gctttgctaa | 60226 |
| ggagctgcca ctgttaagaa attactctct aaaagaaaga aaattggcaa cagcatatgt | 60286 |
| gtattttcag tctcttttcc tcactctatt aaattttgta caagagatgt tatttttggt | 60346 |
| ctagtaaatt tctgtcatgt tttggagtat aaaattactt gtgcttttgc atctaatttg | 60406 |
| tgggtgtaga aaatcataat cttttgaaat accttatata atacattttt ttgccacagg | 60466 |
| aaatacttga agttattgtt gtgtaccttac cgtcatttta gtccaaaatt atacttgtgt | 60526 |
| tctctgtgtg catattttga tatgtattag gagattatgg atctgtgtga tttcttaagt | 60586 |
| aaatcctgat attttcacaa tttgatgatg actctttaaa gttagactta agttttgcca | 60646 |
| aaagcaagaa gcctcaaaga gtaacatttg ttcatgtctt aacactatct ccctcttatt | 60706 |
| ggtcagaatc tcagtatgga tgcagtgtcc atatgcacaa caatatatta attcagttta | 60766 |
| acagacttaa tgctgaataa gcaataagat taattgaatt aactaaatct tttgatagta | 60826 |
| tccacttcca tatatatagt tatagatata atgctagtga atttgaacca taaacaaatt | 60886 |
| aataatacat gtgatttctg tgaaaattta tattagtctt ttcaatatgt caatataggg | 60946 |
| cagtatttct caaatataga ggatcagttt ttcaccattg tccctcttgg ggacatttgg | 61006 |
| cgatgtctgg agacattttt gattgtcatg gctcggggt gctactggta tccagtgggt | 61066 |
| agaatcaaaa gatgctgcta acatcctat catgcacaag gcagccccac caccaacaaa | 61126 |
| gaattatcca gtcaaaaatg ttactagtag tatggttagg aaactatcat atagaggaag | 61186 |
| caatcacatt ttacaagagc cataatattt aaaatgcctt tttgttcatt ctctgtatat | 61246 |

```
ttgactagag tcacaaaata acttgataag attgttgcca aaatattag aaactagaag      61306 aaaaatgtgt tgttaagtct aagagtagtt aaatgaaata aagaattatt cttctttgga    61366
tttggatgcc tgcatcaaga tttagattgt aaggatactt aggactgaac atttgctcta    61426
tatgaaattt gtattaatca aggtatgaat tgcagcaacc actctattaa ttacatatgt    61486
ttggccaggt gtggtggctc acacctgtaa tcccagcaat tgggatgcc aaagcgggct     61546 tatcacctga ggtcatgcgt tcaaactggc ctggccaaca tggtgaaacc ccatctctac    61606
taaaaataca aaaattagct gggcctgatg gtgcacgccc gtagtcccag ctactcagga    61666
agttgaggca aaaaaatcac ttgaatctgg gaggcagagg ttgcagtcag ccgagattgc    61726
gctgctgcac tccagcctgg gtgacagagt gagactgggt ctcaaaaaaa ttaaaaatta    61786
aaaaacacac acacacatat gtttatttac atcag g ctt caa gaa aac  cat gaa    61840
                                         Leu Gln Glu Asn His Glu
                                                              1675
```

```
gat gaa gtg  aaa aaa gta aaa gcg  gaa gta gag gat  tta  aag tat        61885
Asp Glu Val  Lys Lys Val Lys Ala  Glu Val Glu Asp  Leu  Lys Tyr
1680                  1685                    1690
```

```
ctt ctg gac  cag tca caa aag gag  tca cag tgt tta  aaa  tct gaa        61930
Leu Leu Asp  Gln Ser Gln Lys Glu  Ser Gln Cys Leu  Lys  Ser Glu
   1695                 1700                     1705
```

```
ctt cag gct  caa aaa gaa gca aat  tca aga gct cca  aca  act aca        61975
Leu Gln Ala  Gln Lys Glu Ala Asn  Ser Arg Ala Pro  Thr  Thr Thr
   1710                1715                      1720
```

```
atg aga aat  cta gta gaa cgg cta  aag agc caa tta  gcc  ttg aag        62020
Met Arg Asn  Leu Val Glu Arg Leu  Lys Ser Gln Leu  Ala  Leu Lys
   1725                1730                      1735
```

```
gag aaa caa  cag aaa gtaagtaaca acagaaaatt atcaacattt aggaaaaata     62075
Glu Lys Gln  Gln Lys
             1740
```

```
tgtggtagat tgcttttaga gaagatttgt aaatttataa aagatggtag tataaatctc    62135
cgtgttgtaa taaaaagtat gagctttatc ttatgctgtt aaacaaggta ttttagacaa    62195
tgctgttttt gtgggcagat atagtccaat ttatcttttt atgttttcgt caatctgatt    62255
tgtgaattat ctatatgaag ttaggaaaaa tcttaatgta cattacaaaa atataatata    62315
tattacattg tattttcttt ttttctactg gaatttatg ctactgaggc tattttaac     62375 aaatgaacaa ttttgaacaa tttgagggat tgagggaagt atgataatga caaaaggga    62435 tgaaaaaagg gggtcataga gatgttttg tgagaaggag ttggtcagtg tattctgatt    62495
tattagggtt ttttttagtt tatctcagat ttgatctatt taaattgttt tagaagatgc    62555
tggtgttttt ctgtgctagc tatgaaattt atgggtaaac tttaagcctt tcctagtcct    62615
tttgttgtct acctaaattc aattaattc atatggaagg atgtagtaag tgagtaatat    62675
aaatatctaa aattggatgt tgaaaacaa acatacctg ttttttgtaa tagcttgatt    62735
taatgctgag ttctcaaaat cattattaag attttgaact ttcacattca atgtggaaag    62795
aattgagtgt aattacaaaa gatttatttg aaaaagttga gttgttaatt tgtgaaatat    62855
gttccattaa actcataata ttttagaaaa atagtaggaa gtaataaagc ttgtttattt    62915
tttatatcat atattcatat aaaatgtcag ttttccttta aaaattacat tttttttttg    62975 gttaatttt ag gca ctt agt  cgg gca ctt tta gaa  ctc cgg gca gaa        63023
             Ala Leu Ser  Arg Ala Leu Leu Glu  Leu Arg Ala Glu
                 1745                            1750
```

```
atg  aca gca gct gct gaa  gaa cgt att att tct  gca act tct caa        63068
Met  Thr Ala Ala Ala Glu  Glu Arg Ile Ile Ser  Ala Thr Ser Gln
```

```
                1755              1760              1765
aaa gag gcc cat ctc aat gtt caa caa atc gtt gat cga cat act        63113
Lys Glu Ala His Leu Asn Val Gln Gln Ile Val Asp Arg His Thr
1770                1775                1780 aga gag cta aag gtgaacatca acacgtgtta atgtaacaaa atttctgata        63165
Arg Glu Leu Lys
1785 attcctattg gaagagaatt cactatgata tatagtaatt ttgttgatga ataggaatt   63225 tataatgcac tgttggtggc tagacataga cacacacatg cattttttcaa caataagtct 63285 ctttatgata ctcatttact gattatcatc ttggggatta ggaaaggata ggccattatg  63345 aactactgtt tctaatgaaa ttaaatttaa gaaatatttt acttaggatt ttttttaaga  63405 ctttattatt ttttagagc aattttaggt tcacagcaaa attgagagga aggtacagag   63465 atttcctgta tatctcctac cctgaaagtg gtacatttgt taaaattgat gaacctatat  63525 tgatacatca taatcaccca aagtccaagt ttacctctat tttagctctt ggtattttac  63585 actctgtgtg tttagacaaa tgtataatga tatgtatcca tcattatagt attatacagg  63645 gtattttcac tgccctaaaa atcttctgtg cctctcttct tcattccttc ctctgcacct  63705 caccaaaccc ctggcaacca gtgatctttt tactgtctcc atagtttcac cttttccaga  63765 atatgttata gatggaaaca tacagtgtgt ccccatcatt ctcaccatag gacagctagg   63825 aactcctttc tagtggcata catattgtct agtattgtaa gttaccctt tatatcttat    63885 ctttgtaaac taggttagaa attacttcaa gtcagagatt tgttctgtac tactcttatg   63945 cttcatagtg tttaaaacgt tgtcatatat attgttatat acttgtttgt ttaattaatt   64005 cagccaaaat gaaacgtgca tatttgataa aattttgttt gtgggtgttt gttgaagatg   64065 aattgcttta cactagtttt tttttttttt ctcaaagtcg acttttttcc tcaaggtaga   64125 cttgacatga atatggaaaa atatatgtag tttgtggtta tttttttttct cttgtgtact   64185 taaaaattca gactgaattt ttcttataat ggtatatttt ctgttttatg ttccttttat   64245 cattgatact tcttgaagag tcatgaataa tacctttctt tttctcttat tag aca      64301
                                                             Thr
caa gtt gaa gat tta aat gaa aat ctt tta aaa ttg aaa gaa gca        64346
Gln Val Glu Asp Leu Asn Glu Asn Leu Leu Lys Leu Lys Glu Ala
1790                1795                1800 ctt aaa aca agt aaa aac aga gaa aac tca cta act gat aat ttg        64391
Leu Lys Thr Ser Lys Asn Arg Glu Asn Ser Leu Thr Asp Asn Leu
1805                1810                1815 aat gac tta aat aat gaa ctg caa aag aaa caa aaa gcc tat aat        64436
Asn Asp Leu Asn Asn Glu Leu Gln Lys Lys Gln Lys Ala Tyr Asn
1820                1825                1830 aaa ata ctt aga gag aaa gag gaa att gat caa gag aat gat gaa        64481
Lys Ile Leu Arg Glu Lys Glu Glu Ile Asp Gln Glu Asn Asp Glu
1835                1840                1845 ctg aaa agg caa att aaa aga cta acc agt gga tta cag gtaatttat      64530
Leu Lys Arg Gln Ile Lys Arg Leu Thr Ser Gly Leu Gln
1850                1855                1860 atttaactct gataatgtct gatttacaat atagaggtag tagtttattt ctactttatc  64590
attttatcta tggtatttgt taaaactgac tttcaaatca ctttgattaa tgtaattaat   64650
ttcttttgtg acttctattg tgtttatagt tctagagtag catattagta tgttgtatta   64710
aaatgcagaa gcagctacca gattatctta tgtattaagt gtcatttaga aagtatggtc   64770
agtgatagct tcagaaagtt gctattatat aattgaaata tttactgtct attttgtttt   64830
```

```
acatttattt gtaaaaatat aaagttacat tttatttttt ag ggc aaa ccc ctg     64884
                                                Gly Lys Pro Leu
                                                            1865 aca gat aat aaa caa agt cta att gaa gaa ctc caa agg aaa gtt        64929
Thr Asp Asn Lys Gln Ser Leu Ile Glu Glu Leu Gln Arg Lys Val
            1870            1875                1880 aaa aaa cta gag aac caa tta gag gga aag gtg gag gaa gta gac        64974
Lys Lys Leu Glu Asn Gln Leu Glu Gly Lys Val Glu Glu Val Asp
            1885            1890                1895 cta aaa cct atg aaa gaa aag gtatgtgaag aaacatactg acttatatgc       65025
Leu Lys Pro Met Lys Glu Lys
            1900 ttaaggtagt gacagagtaa gttaaataca tagctgatta acagttaata tactgcctta  65085 atttgatgac ctggctgtat taattctgta ttaattttga ggactataag cagtattgaa  65145 taacgtagaa aagtctaagt ttctgttctg taggaattta gagtctactt gaggagatac  65205 ctataatgta actcttattt ggaaattact acatcaattt cattcatctt tctgacatta  65265 gagtacctct gaagttcctt cacaccttaa catattcaac tgtgtatcat ttctctccaa  65325 agtaatcatt tacacaggtt ggtgcttttg acttttggga cagaaagata gacattttaa  65385 gatacccac tttgacccaa ataggtcctt tttaatcctt caggagacta ggctgttatt   65445 tcagatagca aagttatttg aatatcttc agtatttgca gtaataatca gtaaccaatc   65505 tgctcataga ttaattctgt gggagaaatt gcttaaaatt ttatagttca tagtaaactg  65565 ttttgtaata aaaattactg attgaaataa ccccaaaaaa aactaaaatt ggctaaaatg  65625 cgtgtaatta aatttgttat ggacaataaa ttggagataa cttgttggta acattcaaaa  65685 tatcgaaagt gaactgggaa atgttgatgt tagcagtaat atttgccatt gaagaaaatc  65745 agtatggagg agctatggtt aggaaaattt ttattataaa atttacccag aaaatatta   65805 atgtctataa aataatttca atcacatgaa aatggaaaag aaaattctgt ctttaaaggc  65865 attgaataga aaataggtaa tggaattcaa atttcttaat agagtatgct cccaaaatta  65925 ttttctatga aaattcatta atgtcagtgt aatttattga cactatttgc gtggagtcac  65985 aacatgcttg ctgtcagaag ctttgctggt gaaaactgta agatcaaagt gtccttaatc  66045 ttttggattt ccatctttct aactccctaa ttggggatag gcctgatctt atccctaaat  66105 ggggataggt tagaaactgg tatgtttgtt cctaactggt gtgtttctat accagtttct  66165 aacctgattc ctatcagaat gttttaagag ccttgtggct ttgcctggac tcttctatgc  66225 tacagtttat ttagtttatt tattcagttt attcctcctt aaagtgggaa taatactatc  66285 tgtattgcca gtttctcagg attattttac ataaaatgat atgatatgcg gaagtctttt  66345 gtaagccatc acatccatag cagtataaga tattactact aactagaaag agaaaacagg  66405 ggtctatgcc cagtattaaa attggcattc aggaatctag tgagaatatt ttttcaggtt  66465 cattgcttgg gcatttctaa tttatactca agaaatgctt tcatattgtt tggaaatttt  66525 agtacccttt tctctgtaaa cagaatttgt agtctaccta tgtaacaaaa cccaccctg   66585 tgccttgcat ttcattctcc ttagcattta ttactatctt aacatactag acatgtactt  66645 gtcttttgtt catctttttt ttttcttttt ttattagacc ataaactttg atggcaggaa  66705 ctttgcctat tttatttatt attgtattcc cagcacctag aacaatcgct ggcacatagt  66765 agatgctcag tatttgttga atgaaataaa attttttaaat gttataataa tattattctg 66825 aaatctatgc atacgaagct tttggtacag aaaacatgaa aagagaacta ctgccttatc  66885 atccagtctt cttccctctt ctcattcagt ctagaacata acctgttttg gaaaaagttc  66945
```

```
tcaaaccata tgtttatctt gccctcaaac cataacaaca atcaatgcaa aagacttctg    67005 tgaccccag  aatatgtggg gatttctcca catcagcaag caagcagttg gttttgtagc    67065
agacaccaac tgggtgtcgt ccaattcaat tcatcatcta cctggagata gtgtcagatc    67125
ccacagatat cttacttcga tcaaatcaca agtccaggcc tccgtgactt ccgaagttcc    67185
cacatcccca gccccagct  ttgggtttga ttaatttcct ggagtggctc acagaactca    67245
gggaaacatt tacttacatt taccagttta taataaaggt tattacaaag gatacaggtt    67305
aagagatgtg taagaagaga tatggggaa  ggggtgtgga ccttccatgc ctttctgggg    67365
tgccaccttc ctctagaaac ctccacatgt tcagttctcc agaacctctc tgaacccagt    67425
cctcttggtt tttagggaag cttcatgaca tcagtatttc ttctcctagg gtatggggca    67485
ggaccccctc gtatagggt  tttaagaccc acagtcagaa aggcagggga agattacagt    67545
cctgccttag ggcaggtgaa aggaggatgg gagaaggtca gagagactct tttctgaggt    67605
gtgctcggaa ggcctaacac actcaatatt ataactaaag atgaggacaa gggctatgag    67665
agttataagc caggaaccat ggaaaaaagc ctatatgtaa taacaccaca atacccatgg    67725
taccattcac gtttgttgtt tttctgtttt tcaattgttc tttcagtctt ggttcccta    67785 atcttaattt agcaagtaat gccaggtggg ataaaattgc ccaaacccaa caaagtactg    67845
tgtgctgcag gattatttaa tgacatacct tatgtccccc actagtattt acatttctgg    67905
gagtacagaa aaattcttgt acatatttca gaaaaaatga aattaataac tatcaaccac    67965
ttagtgaagt ttttactttt tttttttgaga tggagtttta ttcttgtcac ccaggctgga    68025
gtgcaatggc gcaatctcag ctcactgcaa cctccgcctc ctgggttcaa gtgattctcc    68085
tgcatcaacc tcccaagtag ctgggattac aggtgcctgg caccacgact ggctaatttt    68145
tgaattttta gtaaagatgg ggtttcacca tgttggccag gctagtctca aactcctgac    68205
ctcaggtgat ctgcccgcct tggcccccca aagtgctgga ttacaggtat gagccaccac    68265
acccagactg aagttttac  atttttaaa  gggcacttat tagctgaatt aaataaggta    68325
aaaaattgac tagtattaga gacaagaatt ggagaatata gttctctagt attcgagaaa    68385
gtcgttttga taggacaact aatcttagtg agaatttggc tttatttcat atttttttaa    68445 tttttttgaga tgacgtctta ctatgttgcc ctggctggtc tttgaactct gggctcaaac    68505
aatcttcctg cctcggcctc ccaaagtgct gagattataa gcatgagcca tctccccagg    68565
aatttgactt taaccatgg  ttctcaaccc tttcagattc aacattccct ttaataaaaa    68625
atataatgtt tcataatttc ccctttacta ttataattga aatgcatagt taacataaac    68685
tctacctact tacataattt caaaaatgtc attatgaatg tcctaaatga aatatatagg    68745
gggaacataa aaggaatatt catatttcaa catgtaaatg ctttggcatg actccattgg    68805
aaaatataat gaactagtca tgtgcttgca ccttcattaa tgtgagttca aagctacgat    68865
tgcagactga cacaaatgtg ttctattggc aactgatggg tcatgatggt attgccattt    68925
gtaatttgat ttccaaaatg gtaaacaaat tgttggtgca gttctcagca aaacaatgtc    68985
tataatctta ccttttataa gactgttgta ttcctagaaa acttagtgta tagtaaaacc    69045
attaaaaaat tacttagtgt gaatatgtta gttggagata aattcttagc tcagaccagt    69105
gtaagcagaa ttttttactg tattaatatc cagtagaaca tttgaaagtt gttcagtgca    69165
tgagactatt ctgcattgga taggcttct  ttggctccct tatcatagtt ataataaacc    69225
atgacaccta cccctgaaat gccctaattc ccttccgttt cttttctttt tttctttta    69285
```

-continued

```
gcacttaaaa ctagctaact tactacaaaa tagatttaga tttatttctt gttttgttat    69345
ctgtatcgtt tgctcccttc tccccaatct atctaaccaa ctagtataaa ctagatagta    69405
agattcatga agatacactt ttttatctga ttttattcat ttgttctatt cctattgcct    69465
ctagagtagt acttggcaca tggttagcac taaataagta cctgtcaaat gagtgaagta    69525
atgtgcattg aagacttgaa ggggctctga tgctaggaaa ttgtcatggg ataatagatg    69585
aggttggtcg tttgtacaga ggattcttgt tagaagctta ctctagtcat gattgtatta    69645
gaatcttcat ttaaaggctc ctgaagggtg ttggcattag tcagaactgt ctcccagaat    69705
tttatttgtc ttgtgataga ataaagcata gttagcctaa agagcagttt tcctaatagc    69765
tcggcatgcc caaagattct aggagttata caggttgaac atctaatcca aaaatctgaa    69825
atgctccaag atacaaaatt ttttgagcac caatatgatg ccacaagtgg aaaattctga    69885
tgtgacctca tatgatgagt cacagtcaaa acacagtcaa aactttgttt catgtacaaa    69945
attattaaaa aatattgtat aatactacct ccaagctatg tgtagaaggt gtatgtgaaa    70005
cataagtgaa ttttgtgttt ggacttggga cccatcccta agatatctca ttatgtatat    70065
gcaaatattc caaaaatatt ttttaaaaaa atccaaattc taaaacacgg ctggttccaa    70125
gcgtttcgta agggatactc aacctgtata gcaaaatgaa catatttaca tattctctag    70185
gaaatattag tttacaattt ttctaggcaa attataattg ataaatcata aagaaaattt    70245
aaaataacac tggtaatttt cctacctcct tcgttattgt tacag aat gct  aaa       70299
                                                  Asn Ala Lys
                                                           1905 gaa gaa tta att  agg tgg gaa gaa ggt  aaa aag tgg caa gcc  aaa       70344
Glu Glu Leu Ile  Arg Trp Glu Glu Gly  Lys Lys Trp Gln Ala  Lys
             1910              1915              1920 ata gaa gga att  cga aac aag tta aaa  gag aaa gag ggg gaa  gtc       70389
Ile Glu Gly Ile  Arg Asn Lys Leu Lys  Glu Lys Glu Gly Glu  Val
             1925              1930              1935 ttt act tta aca  aag cag ttg aat act  ttg aag gat ctt ttt  gcc       70434
Phe Thr Leu Thr  Lys Gln Leu Asn Thr  Leu Lys Asp Leu Phe  Ala
             1940              1945              1950 aa  gtgagtttaa atatcattat aaaactaatt atgtgtaaaa tcctttagtg            70486
Lys acctggaaat tatatagctt tatcatagtt gataatatga gaaatggtct agtttaaatg    70546
atcatttatt atctatgatt tacttacttt ttatttttctt taaaatctgt tttaaatata    70606
ttgtaacaat tatagatgga ttttcctgtg atctcgttgt aaattagctt atgacaaata    70666
tagggtgtta caattattgt aatttggttt ggtaatgagt atgcaattga aaagccaaac    70726
actgaatggt atatttcatg attctatatt aaattccaca g a gcc gat aaa  gag     70780
                                              Ala Asp Lys  Glu
                                                      1955 aaa ctt act ttg  cag agg aaa cta  aaa aca act ggc atg act  gtt       70825
Lys Leu Thr Leu  Gln Arg Lys Leu  Lys Thr Thr Gly Met Thr  Val
             1960             1965              1970 gat cag gtt ttg  gga ata cga gct  ttg gag tca gaa aaa gaa  ttg       70870
Asp Gln Val Leu  Gly Ile Arg Ala  Leu Glu Ser Glu Lys Glu  Leu
             1975             1980              1985 gaa gaa tta aaa  aag aga aat ctt gac  tta gaa aat gat ata  ttg       70915
Glu Glu Leu Lys  Lys Arg Asn Leu Asp  Leu Glu Asn Asp Ile  Leu
             1990              1995              2000 tat atg ag  gtaagctatt atgtggaaat gtgccaccca ttgtaatgaa              70963
Tyr Met Arg aaactggttg accCctagaa attgaaataa taaatgtgtg ttgtcttaag cttgggttat    71023
```

```
gttttcttttt cccatgtgaa ttgagatatt cctggttctt catatgccac ataattttgg    71083
tgtatttttg atcttttgaa tattatattg tgagactctg gttcttgttt aaattctatg    71143
ggaaaatgta gatactttg ttttagcatg caatcggtct aattaggttc aggccacaag    71203
ttccaacctc atttcttggg ctgtggttcc attttcaaa gccttttcaa tactcttcag    71263
atctgtcctg cctgtgtacc tcacaatagg tgatctggta tgtgagctat gtaccattag    71323
ttcagttctt agaactttg gtattctgat taggatcgat ccatacattt gcagctcaag    71383
agtgagccca gaagttcata aacaactta tagggtccct ttcttgagct cctccctctt    71443
tgccatctct ctgatacttt gtttccctag ggatttccat ttggggcttt agttacccag    71503
tgatgccatg tacttcagga attgcacact tctgcagcca agcaagcaag aggagagtag    71563
aaagaggaag aaaaaacga cttttacctt accctcttag tatcatagct ctaccaattg    71623
gagatttccc tcccaaaaaa tattagcttc tgtgagttcc cattgcagcc tctattacca    71683
ctgctatggg atggcttaag ggttggggca tgaaagaaca gatagaagaa aaaaaagtg    71743 aggtgtttc atattgtctc ttgagtgtta aaagattccc tttctcttta ctcgagctag    71803
aattagaagg tttacctgga gctctctctg tcagtgcaga cacccatctt caggtttcaa    71863
ataatgttgt cttcagggca ggcagtaaca gaataaaaga aaaggtaaat tcatcacctg    71923
tttgctgcta ctttaagtcc tggtattcta ttgtaatctg ccttctactc ctttgcaaag    71983
tcctcaaatg gttgctccat gcatttagga gagagaagat tgaatgtatt tactccattg    72043
tacctggaac cagatgccct tgccctgcat caccccatgt catttcttag cagagccttt    72103
gagatttttg tgtgtgtgtg ctttacaatc tctttccaag ttatatcttc tgatacagtc    72163
atggtcgtga aaagcaaaat aaaatcatgt gttaacattt aaaacttttt aattttattc    72223
tgacaacagc taaaactatt taatcttctg tttcgctcat ttcttccaag gtaaacttca    72283
gttggtttta cgtgatttgc tatttcttct tctttgcatt tacaaatgat ctgtgatcat    72343
attactgatc tttgtaaagg gctaatatct acctgcaaca tttggatatg acagtattta    72403
ccctttgtaa atacacattt tctatttatc ttcaaaaatt accattcatt agtctgtgtt    72463
aatgtctgtt tactattgtg tcattatgaa tgtgatgtga acatacgaag ttgaacttat    72523
ttaaacgaac actctcatga gcttctaatc cacattcctt cctttccctt ctaagttacc    72583
atttcttaaa aatcttttag aagtttcctt gatagggaaa acacaaatta ttgaggaatt    72643
tttctttctc ttgacatctg tttatagtta ctctcttgtt ccagcagtgg atatttcccc    72703
tccatgtttt tctttgtcta aacatatgtt caaaacaaaa cacttttatt cttctttgca    72763
ggttttacaa ggatcaactt ttagttttga aacctgctat tactttaga ggccattttt    72823 tttttctcta ataatgtgag ttcatgcggg ctgaagtaat tggaatactt tatagaaaag    72883
attgaatttg tcttctctct gaactctagt ttgaatttct aaatttatg aatcatctag    72943 atattaaaga ggaggggcat atcaaagagg agaaccctag cagagataag aggcaagagt    73003
aaatgtttca tgtatgggta agagtggatt tgtatttacc taagtaaagg tagaccctgg    73063
acaataaggt tggatagatg tggaggtggc aaaccatgga gggtcttgta ggtcaagtgg    73123 atgttttag acttgaagtg ttaaattatt atctgaaatc attaagagtc ttttttagatc    73183 cttgagcttc ttgagaagac catggatatt atgcagttat tatataatgt tttaaaatag    73243
taagtatttt agtttaactg tcttatgtaa ttccatataa atggatgcat gttcttttaaa    73303 aatgttaatg tatttcagta aatcaaaata tacttttga ctcatcattt aaaggaggcc    73363
```

```
ttcagtgaat gctctgtaga ggattatttt ataatactaa ttttgatatc ctaatttatt     73423
tgttataaag tttagaaggt ttgaagaatt taaaatatag tgttaataaa cacactgaac     73483
ttttcttttt ttatcttgta tttttatata gtacaacaga aaaagatga aatgtgaata     73543 gtaaagagtc tgtgattgtt gttcatag g gcc cac caa gct ctt cct cga          73593
                                 Ala His Gln Ala Leu Pro Arg
                                 2005                    2010 gat tct gtt gta gaa gat tta cat tta caa aat aga tac ctc caa           73638
Asp Ser Val Val Glu Asp Leu His Leu Gln Asn Arg Tyr Leu Gln
            2015                2020                    2025 gaa aaa ctt cat gct tta gaa aaa cag ttt tca aag gat aca tat           73683
Glu Lys Leu His Ala Leu Glu Lys Gln Phe Ser Lys Asp Thr Tyr
                2030                2035                2040 tct aag cct tca  gtaagtgtat atctttatt attttttct tttttccatg            73735
Ser Lys Pro Ser
            2045 ttaaaatgca tgaaagtgaa atcaacttct tcttaatct ggccaaaagc attacatctt      73795 tctcattaat agtaatacag taaattcaac ttttattttt aacaggtagt gatgtgtaat     73855 aatttattta atccttttta acataataac agtaaactta agattcttaa gcttttcata    73915 aagctcataa atgattccta gaaattttaa atatgtagtt atcattatgt attttgctgt    73975 agcagcagta tacagttaaa taaaatagga aaacatgttc caagactgtt ttcattcaaa    74035 tatttatgct atatttttag cttataaaaa ctcattaatc attaatgtaa aattatttgt    74095 tggatttttt aaatatttag tgtattattt ttgtttcttt tttctttcca tgtttcttca    74155 ttcttccacc ttaagcagaa tcaggtgtgt gacacaacta tgttttctat ccttgttacc    74215 attattaata aatacaaggg catgatattt ttcacaaaag aaacactttg ttcagaacca    74275 aaaaagatca tggcaacagt cagaattaaa aatggtaaaa gactaggtgc caaagatgac    74335 ttacataatt gggtacctag aaatattcta tggtattaca gtaatgatga aaaatacaaa    74395 ttagaacaca ttttagatcc tattgagtta aataaatcag agtcaagacc aaacaataaa    74455 taaagtcaat ttacgtcaac aaatggtaag ttggcagatt ttaactccct ttttgaaaat    74515 gaaccatgat cctaaggttg gtaaaattaa tcaagaatgt tgtcaaaatg ataaagataa    74575 aaatgaggaa gagaataaga taggcaagag tgagaaagga aagagacaca tagctgaaaa    74635 tgtgagtcac aacaactaca tagatccgta gaatctgcta tggaggactg tgattatgtg    74695 acagttgctg atgccgtggc ttagtgagct gagggtgatg cacaggcagg cgatgtaact    74755 gatgcgtcag tccagccaag aaaggacgcg tccctggttt ggctacgtgg ccgtcctta    74815 tttctttgtt aactgaattt tcttatagta agtagcttac gtacatatat agtgcaaatg    74875 ggaaagtgtg taagatttag aaaaagcatt aactattagt aaactttatc ttaagctcta    74935 acttttgatt agttcctaca aaaattagtg aatatgcatt ttctaattta gtgctttttt    74995 ttttttaca attggtgttc acttaatgtt atattagata aatgaatagc aaaataagg      75055 tactttagag ttgattgttt tgccttacaa acttctaatc catccagctg tatttagaag    75115 taagatctca ctacagcgaa ttatatcagt aaaattttgt tacagtgttg tgcagtgtcc    75175 taagatgtat actaagttcc ttcagtggct ttttttgcca tgtttataa cagataattt    75235 tgttataatg agaaaaggaa acttggatgt gttgctgtct atattgtgtt aggctcaggc    75295 aggatgctgt ggcttactca tttaatcact ttgggaggca ggggcaggaa gattgcttga    75355 ggccaagagt ttgagatcag cttgggcagc atagccagac cctgtctcta caaaaaattt    75415 agacagatgt ggtggaacac atttgtagtc ctagctatta gggaggctgt ggtgggagga    75475
```

```
tcatttgagc ccaggagttt gatgttacat tgccctattg cactccagac tgggcaacag    75535
agtgagacct gtctctaaaa taataataat gataatgata aatggtgtta ggctctgtgc    75595
ctaagtatat ttttcacata ggctgggtaa agtggctcat gcctgcaatc ccagcacttt    75655
gggaggccaa ggcagcagga gcatttgagg ccaggagtca aagaccagcc ttgagagacc    75715
ccatctctac cagaaaaaaa aaaaaaaaga aacaattagc tgggtgtgat tgtgcacacc    75775
tgtagtccta gctactcggg aggcagaggt gggcagatca cttgagccca ggagtttgag    75835
gttatagtga gctaagattg tgccactgca ctccagactg gcaacagag caagactgtc     75895 tcaaacaaaa acaaacaaac aaaaagcact ttgcagaata tcagtctaac tctacagttt    75955
atggactttt tatgtacgta ctacttttgg ctagcttaca ttgagataca gaataaaagt    76015
ttgttcatag catttatcgt tttttttcttt atactgtcca cctgagatat tccagtcacc   76075
taagtcatgg aaacatcaac taaaattaaa tatctatgtt aagagaaaat ggctgaaagt    76135
gatttaattc ataacacttt ttttcacatg ctaataaata agagtttgag acttccacta    76195
ggcattatct ctaactccta tccactaaga atttgatttt aagtagttga tggcttttaa    76255
ccggattatt cttctgtaag agtttggaag tctcgtgaag ttcgttatac aagaattctg    76315
tttacaagag agcattacat tagaatttgt ttttcagaaa tttggactat ctcaacgaat    76375 accttttagtt ttattatttc aaaatgcaag ggaaaaaatg agccataatc actaatagta   76435
actgcatcat attttagtga gaaatgtgtt aaaaatatcc tcatgtgaga tcttccttag    76495
atagaattac cctctactct aatatttaat atattttata tctaccaatc agtgatatta    76555
ataggtgttt atcatttgct gaatcaaata ggtacaacag aagacaggaa gtttgggaga    76615
tagaagagct cagggacagg aaatcacaga tgtccatatc tgaaataacc ttaaaagtta    76675
tcctgtctaa tgccttcact tataaactgt agtggtagaa tttgcctagt attaacctaa    76735
tagtggtaga tttgaatgta tacttgggct ttcttattaa gtggaaatgt attcctgtga    76795
tttacatata tcaacaaaaa tgtttgtctt cttttttttg ctacgacata tgtgcatgtg    76855
cacacacatc tcctcaaaca aaatcagat ggacacatgc agtcattgga tctaaaagat     76915
gttataaagt tgtgtataat aggtattta taataatata ttttaagacc cataatgtcg     76975
gtggagtaac tgactttaca gcccatcaag ccaatagaga gagaaaggag aaaaaaatga    77035
aagttgtgct gaataattaa aaaaaattat ttcctatgat gcttataaca gtcctatgag    77095
gtaggtggta ttctaatttta tagaaaaaat gcatagaaaa atataattaa gcacagttaa   77155
aaaaaataaa gtttagaatg agaagtaaca acataaaataa tgacccaatg tagattcagg   77215 tcaaagaaa tgaaaatata atattaatgg ttttcaaaga gggaaccatt actttagctc     77275
aaagaatgaa ggagggcttt ccgaaggagt aaagaattat ggcagttctt ttgtagccta    77335
gtgtattcat ttgctaaggt ggctgtaaca gactactaca gatttggtgg cttaaacaat    77395
agaaatttat ggtcttagtt ctggagacct agaagtccaa aatcaagaca tcagcagggt    77455
tgatttcctc tgcacaatca gagggaaaga tctttcccaa tcctctctcc ttggcttata    77515
aatgtccatg ttttcctgt ttctttttat catcttcctt ctgtacatgt ctctgtgtct     77575
aaatccccaa attttctctt ttcataagga taccagtcac agtcgaatag ggtttaccct    77635
gaaatctcat tttaacttga atacctctgt aaagacccag tctccaaata aagtcacatt    77695
ctgaggtact ggaaattatg actttaatat ataaatgtgg agggtaaggg gaacacagtt    77755
caacccataa cggttagata acaatcgtgc tttattttgg actagtaaaa ccaccataga    77815
```

```
tcagtttaac cattatgaaa ttatacatga aggcattata tgtatggaca ttattaagtc   77875
atacttgctt tgcttccatt gtaattaaaa caaaccatac tacctttgtt ctgcaagttt   77935
tgtattctaa cttatttatt tttggctttc accagaacac tccgattttc tcatattcct   77995
ttgaggaaaa aaagttacct tttgacagta ttttcttatc cagtatgtct tttatggctt   78055
ttatttatta aactttaaaa atattcctaa tttcatttcc ctgaag att tca gga       78110
                                                  Ile Ser Gly ata gag tca gat gat cat tgt cag aga gaa cag gag ctt cag aag          78155
Ile Glu Ser Asp Asp His Cys Gln Arg Glu Gln Glu Leu Gln Lys
     2050                2055                2060 gaa aac ttg aag ttg tca tct gaa aat att gaa ctg aaa ttt cag          78200
Glu Asn Leu Lys Leu Ser Ser Glu Asn Ile Glu Leu Lys Phe Gln
     2065                2070                2075 ctt gaa caa gca aat aaa gat ttg cca aga tta aag gtgaatttaa           78246
Leu Glu Gln Ala Asn Lys Asp Leu Pro Arg Leu Lys
     2080                2085                2090 tgttttttat taggaaatct aatgcctaaa actccttcct tagttgttat gtttactttt   78306
attagcttat taagaagtca aaaatgcata ttcctaatat atcatggtga tggtatactt   78366
tatacatttg ctctttagca tttatttgtt gaaggcctac tttatattaa acactcctcc   78426
agatgctggg aaacagcagt caaaaaattc cttatactca taggacttac gttctagtgg   78486
agaagactga caataaacaa gtcactaaat agtatgtcat ctgatgttag tgctaaggag   78546
agaaataaag catgattggt gtaaagagta tggggagaga aagggggtgt aactgaaaat   78606
agagtagtaa gggaggtctt ccttaataag atgatatatg aacagagagc taaggagggg   78666
taaaggaagt gagtcataca gatactagaa aaataattac agacaacaga aatagcaagt   78726
tcagatgtcc taaggtggga ggatgcgtgg tatatttcat taaaaattat cacactgtaa   78786
aatataagaa taatttgttt cttttagaaa ttttacttta ttctgatatt aataatgatt   78846
ttttaatctt tggttttcca agtcttaccc tatttatggg aatcttttt ttcttttggc    78906 tagctaattg cttcagtttt gttttctaat ctagaatgtt agcaatctgt taattccact   78966
ggtaatgata tagttaagct atgtcttgct tctcacactt tatttattta tttactcagg   79026
gcactaatct gccatttttt cgcacttttt ttccttttt tttttttgg tactgcttct     79086 tattctggtt tttacattga tagaaccaat gttagacgtt catttgcctt ttgctgtgta   79146
tatttgggta aggatctata tgtgcaatat atgggacagt taaaatcaga attctaaatt   79206
tgtattattg catcaggcaa taatgtggga aataccttga catttcatat acacaatatt   79266
cttgtattaa tttaacgtct tagttcaaaa tcttccttgt taatatagag accctattat   79326
ttggtttggc aatacagttg aagagattga tggttcttat gaattgtttg ccttttcttt   79386
tcaatggctg tagctatgtt aaattattac atgtttgctt gttatctttc ag aat caa   79444
                                                          Asn Gln gtc aga gat ttg aag gaa atg tgt gaa ttt ctt aag aaa gaa aaa          79489
Val Arg Asp Leu Lys Glu Met Cys Glu Phe Leu Lys Lys Glu Lys
     2095                2100                2105 gca gaa gtt cag cgg aaa ctt ggc cat gtt aga ggg gtatgtgaga           79535
Ala Glu Val Gln Arg Lys Leu Gly His Val Arg Gly
     2110                2115 atttaccata catttgtttt ggtttcagca gtgataagcc agaaatgaaa agtttagata   79595
tgttgtaaaa gtactgatat gcctctacaa gtgccctgta gtttcagtgt ttattctgca   79655
tctgtaatat aaaacagtaa gcatttctat gtgtctcaaa gtattttatc atctgttata   79715
ccttacatac tttcatctct cttttttattg aatatgcctc cataccttga aaacatttaa  79775
```

```
cttccaggaa tcctttgtt tatggaggta actgctaact ggtccttggt ccaatgctgc    79835
catttgtaa ccatttgtta tgatatcttc ccagcttggt ataatgtttt ataattacat    79895
tgttcctccc cctcttttt tgtgttcttg taatttctc cctatgttat tttgtattca    79955
ttttatataa tgaataaatg ttgcttatga ggtcaaggcc aaagacttaa gctcctgttg    80015
atttcatgtt gctgagtgtc ataaatggaa gcaatcataa tgcagagtca ttctggtagt    80075
aatattaaat atatgatgga ttcagtgaaa atattatgtg ttattagaaa aatattcaga    80135
acaggccggg ggcagtggct cacacctgta atcccagcaa tttgggaggc cgaggcgggc    80195
agatcactgg aagtcaggag ttcaagacca gcctggccga catggtgaaa ccccatctct    80255
actaaaaata tgaaaattag ctgggcatgg tggctcatgc ctgtaatcct agctactcag    80315
gaggttgagg caggagaatt gcttgaacct ggcaggcgga ggttacagtg agccatggtc    80375
acacaactgt actccagcct gggcgacaga gcgagactcc atcttttaaa acaaaaaaaa    80435
aaaggaaaa atattcagaa cagtatcttg ctggcagcaa catttgtttc atcaatgaaa    80495
atatgtgtta atttgacctt ttctatctaa gttaattatg aaagtgcata ctaaaatgat    80555
gtaaaagttt atatttcagg attattctta ttcatggatg attaactaaa atgcaaaaag    80615
aaattaagca tactgtttgg ctaaactgtt aaaaattatt tttattttaa atgataagca    80675
gttaaactta ttaagtgatg actcatctct gctgatatat ttatgcaagg ttttttattt    80735
cagataactc ttctatttat attaaacaga aactgtattt ctaagcaata gcatttctta    80795
gagaaaattg cctctattat gttgcaatta aaatttaatt actcatgagc tctttaaaga    80855
cacaattct cttgtgtggt tttatttcat ataagaaaa actctgatat actggagaga    80915
acattagcta aatagactat ttagacttaa tcattttgat cagacatcaa ggctagacta    80975
tttaagctgt tacttattag ctgcatgatt ttaggaatgt caaatttcct aagtcttggt    81035
tttcttgtat ttaaaatgga aattataatt cctatctcat agaattgttt taaggatgaa    81095
ttgaattaat acagttttga cttcaaatat taggaattat tgagtataat aagcctgttg    81155
tattgttggt acttcgtatt atacttacta aaatatttga ttaaagattt aacatattct    81215
```

| | | | | | | | | | | |
|---|---|---|---|---|---|---|---|---|---|---|
| ttcgtag tct | ggt | aga | agt | gga | aag | aca atc cca | gaa ctg | gaa aaa | | 81261 |
| Ser | Gly | Arg | Ser | Gly | Lys | Thr Ile Pro | Glu Leu | Glu Lys | | |
| 2120 | | | | 2125 | | | 2130 | | | |
| acc att ggt | tta | atg | aaa | aaa | gta | gtt gaa aaa | gtc cag | aga gaa | | 81306 |
| Thr Ile Gly | Leu | Met | Lys | Lys | Val | Val Glu Lys | Val Gln | Arg Glu | | |
| 2135 | | | | 2140 | | | 2145 | | | |
| aat gaa cag | ttg | aaa | aaa | gca | tca | gga ata ttg | act agt | gaa aaa | | 81351 |
| Asn Glu Gln | Leu | Lys | Lys | Ala | Ser | Gly Ile Leu | Thr Ser | Glu Lys | | |
| 2150 | | | | 2155 | | | 2160 | | | |
| atg gct aat | att | gag | cag | gaa | aat | gaa aaa ttg | aag gtaattttt | | | 81397 |
| Met Ala Asn | Ile | Glu | Gln | Glu | Asn | Glu Lys Leu | Lys | | | |
| 2165 | | | | 2170 | | | | | | |

```
ttaatgtgat catttttagg ggaatatttt acgttttgtt actatttagg aaaatttcaa    81457
atatgctcat tactatataa aatggcttta atgaatacaa tacatatttt ataaatatag    81517
aaaaaaactt atgagaggca aggctaaggg ttatagagta ggtctacctg atctttcttg    81577
ttatttcaag accaatactt ttcacttttc tctctgacag catagattaa ttacctgtgt    81637
ctctcttttt tttttctttt gagatggagt actgctttgt cacccaggct ggaatgcagt    81697
ggtgcaatct tgactcactg caagctctgc ctcccgggtt catgccattc tcctgcctca    81757
gcctccccca gtagctggga ctacaggtgc ccaccaccac gcctggctaa cttttcgtat    81817
```

```
ttttagtaga gatggggttt caccatgtta accaggactg tctcgatctc ctgacctcgt  81877
gatccgccca ctgcggcctc tgtgtctctt tgtgaaaata cagatgccca agctcccatc  81937
cctgaaattg atttaattat tttagggtgg gtcctgacac agatatgtat gttgttgtta  81997
ttttaagtca tcaatttatt ctaatatgta gccaacgttg ggaacttcgt tctcactaat  82057
attcaaatga agactttaat tctaatcata tcaaatatgg tttctaaaac tactttgaag  82117
atttatgagt ttataagatt atctttattt tccttgtttt gataatgtat acttttattt  82177
ttgtttgttt ttttactag gct gaa tta gaa aaa ctt aaa gct cat ctt      82226
              Ala Glu Leu Glu Lys Leu Lys Ala His Leu
                  2175              2180 ggg cat cag ttg agc atg cac tat gaa tcc aag acc aaa ggc aca       82271
Gly His Gln Leu Ser Met His Tyr Glu Ser Lys Thr Lys Gly Thr
2185              2190              2195 gaa aaa att att gct gaa aat gaa agg ctt cgt aaa gaa ctt aaa       82316
Glu Lys Ile Ile Ala Glu Asn Glu Arg Leu Arg Lys Glu Leu Lys
2200              2205              2210 aaa   gtatgacttt tatgactgat tataactttt gattttatt ttacttaata       82369
Lys
2215 cctcttggaa aaactggaag tagatccttg atgagagtgt ctgtaaaggt agatattaag  82429 agattgagga attgtgtttc tatgcctgct gtcatcacat tccaccatga aaaacattga  82489 taataaaagt taatacattt aggctgggca cggtggctca cgcctgtaat cccagcactt  82549 tgggaggcca aggcgggtgg atcacgaggt caggagatcg agaccatcct ggctaacacg  82609 gtgaaacccc gtctctacta aaaatacaaa aaattagccg ggcgtggtgg cgggcgcctg  82669 tagtcccagc tactcgggaa gctgaggcag gagaatcgct tgaacccggg aggcagaggt  82729 tgcagtgagc cgagatcgca ccactacact ccagcctggg caacagagcg agactccatc  82789 tcaaacaaac aaaaaaaaga aatgatctac gttgcttaca catacccttat gcttatagct  82849 aggtctcgta agcattagga agtcaaaaca aagaatcttt tacatgtgta aaggtataaa  82909 ctatcccatt tttctaaaaa tatagaggaa caaagtgtca aatttaaagt aatcactagt  82969 aactaaatat attcctctga cctcattttc gtgatctgtt gttctaatta ttattggcca  83029 tattgctgct ttaaaggaga gatgttgaat ttgttgaaat tttaatcagc atttagagcc  83089 ccaggttatt tttgttttcc aatttgtaat gataattttg aatacactga atctatgaga  83149 acagtattat gttttctcat aaaatactaa ttagcattta atgatag gaa act gat   83205
                                                  Glu Thr Asp gct gca gag aaa tta cgg ata gca aag aat aat tta gag ata tta       83250
Ala Ala Glu Lys Leu Arg Ile Ala Lys Asn Asn Leu Glu Ile Leu
    2220              2225              2230 aat gag aag atg aca gtt caa cta gaa gag act ggt aag aga ttg       83295
Asn Glu Lys Met Thr Val Gln Leu Glu Glu Thr Gly Lys Arg Leu
    2235              2240              2245 cag ttt gca gaa agc aga ggt cca cag ctt gaa ggt gct gac agt       83340
Gln Phe Ala Glu Ser Arg Gly Pro Gln Leu Glu Gly Ala Asp Ser
    2250              2255              2260 aag agc tgg aaa tcc att gtg gtt aca ag gtaggaacag agttttaaac      83389
Lys Ser Trp Lys Ser Ile Val Val Thr Arg
    2265              2270 ttgtacaaag tttaatcatt tcaaattttg gcattgtttt aaaagacaac actattctgg  83449
ataacctggt ttcttcctga tgaacagttt gtttggttgt tgtttaaca taatactttt  83509 tttctgttgt agtattgttg gagactttt cttccttgaa atgtttaact tgtttaacct   83569
```

```
tgtttgggtg gcagggcatg gaacagtgta gagctggggc tgggcgaagg agttggagct    83629
gtgtgtgcgt catgaagctg tcatcagcta tgagcctggg ctgaggctgc tcagcttctc    83689
ctgggtgcta ttttctcca actgcagctt cagcttcttg attgtataat ttgcttcctc    83749
aagtatgagc caggaataat tgagctgtct tgtcacaatg tgtggcatac tggatctagg    83809
ctgtgctgca atgcttttag agttatatcc tgggcaactt tctcttcaga tagccccaag    83869
agatgaattc agcaccagct tgatgtttt actagcttct gctttctggt acttgatttt    83929
ctcccacccc gaacacatgg gattccaacc tgtgaaacta attttgtgg ctatgaaaga    83989 ggtagtggta gtttatgagt aaacattcag tctgttgcca ctatcatcat gtgtggttca    84049
tcatgactgt gatgagtagg taaaaggctc tttgtgtcat tctcatttcc aattttaagc    84109
agctgcttca aggagtctgg aagtcattga ccagtgggat cctgcctgtg tcttttccca    84169
ttaaagccat cctgtatgaa gtggtatcct ttaccatcta gcacatctgc cgccccatt    84229 tcaaaaggca tactcatctt tatctcaaca ttctcataca gttccttatg tccatgcacc    84289
tccaatgtcc cctttgatgt ctttgaggtt ttcatcttcc atgtctgcta tttggaatgg    84349
tcttgatggg aggcaagata gtgatcacta caactaggat gggagtctta gtaccgtgag    84409
gctacagcaa gtcccacaga gggcctgctg cactgtactt gcctctgtca accaagtcta    84469
aggagaaaga ttaagcaggc atattaaagg acagcccaga tggacatgaa gtcctggagg    84529
aggccttggt tcctgtccta atactaaacc tagagtaccc agaatccaca cttctccact    84589
ctagctctca cttttcccat ctacacactg ggaaaaatta ttctgtcaga aagccagtgt    84649
caaggtgaga acaaataaca aatgtgatga tatgagtgg gagaagggt ctcttctact    84709 gtcttattgg accctagcag tggctctgag ccagcagtcc tgtcagttga tttcttggtc    84769
gttcctttgt tttcttctat aatcacatgt ggactcagaa tgaattttga gttactctga    84829
aatctattta ttcaacagat atttacttag tacctcctat tgccagactc tgctttatgt    84889
tggatattat ttttaaaag cccaccttgc ctagattcc tcaaaggacc aggtggcttc    84949
cctggttttg aaagacccta attcttacta tgatcttaag taaattatat cctttctgtg    85009
ggctcaagtt cttcctaaga gggctctttg gggctacaaa agaaattgtt agtgcaaaaa    85069
gagtttataa ggtttataaa tggttagtag aggtgatgat gatatttaac cataattgaa    85129
gatgactttg catttagat catatacgtg ttttcgtct gagaacgata caggtcactg    85189
agcataccat aagccttcag taaatcattt gcagaagaca ttcagaagaa cataagtcta    85249
agtagaaatc tcttgacaga gagaaggctc gttttgatcc ttgacctcaa atttaggttc    85309
cctaaatcca ttaaaaaaga gaaagaaaaa gaaaaaaagt tactaaagtt taaatctggg    85369
aggattatat acccttctca ataaagcagt ttagagagat ctcttttggg acccatgaca    85429
caggtcttgc tcatgctgac atctttatag ttgctttatt atttattcaa caaacttagt    85489
aacacgtatt ctatgtcagg cctttttcctg actactggga caaaccaggg tgatgtgggg    85549
gctgttttag atagggtgat cagaggaggc ctctctgttt gggtggcttt tgaatagaaa    85609
attagatgaa gtgaaggagt aagcttctga tatttcactg tttacttgtg gtagatctgt    85669
gataatctct gtcaggttaa aaacattccc ttctaatcta agtttctaag atctatcaaa    85729
agctgtttga atatatttag acaatcataa ttttccttc ttgtattatc ctagcagatt    85789
ttgttgccaa agctatactg gccatttaa cttagaatgc agtctttcta ttcatttctc    85849
tggaaaagtt tggatattgt aagcattatt tttcttaagg tatgatgaac ctgcagaact    85909
gtttggttca attatgaatt tttttttct ggagtctgta ttttttgaa ctattaatca    85969
```

-continued

```
tttctttaat gattataaat ctattcagat ttttacaagc tttatccctc tcccatcata    86029
cactattttt cttacccatg cttttgcaca attttttcct ctcccttagt gttttcctac    86089
ctagatacct cctatgtgtg tctgtgtatg tgagaaaagc ttttatttg ccatctttat     86149
atttctaaga atatctagta atacagaatt ttatattctg aagaatttta ctttgcattt    86209
tcttattttg tgattgaaaa aaggtattaa tttaaaatg gtcaaatcag gctccatcct     86269
tggaaaatac ccaaatcctt tatttgatt gggccatctg ttaattaggg ataccttatc     86329
tcttgccacc acttttaat gctaaataaa tatgtagcta aaactttgac tagaagaaac     86389
agtaaaataa gatattcttg cttattttta gtacagttat ttgaactgac ttttaaatca    86449
gtgacataaa ttatttgcca tgtctatact tttttccttt atactttag a atg tat     86506
                                                         Met Tyr
                                                         2275
```

```
gaa acc aag tta aaa  gaa ttg gaa act  gat att gcc aaa aaa aat       86551
Glu Thr Lys Leu Lys  Glu Leu Glu Thr  Asp Ile Ala Lys Lys Asn
            2280                 2285             2290
```

```
caa agc att act gac  ctt aaa cag ctt gta  aaa gaa gca aca gag       86596
Gln Ser Ile Thr Asp  Leu Lys Gln Leu Val  Lys Glu Ala Thr Glu
            2295                 2300              2305
```

```
aga gaa caa aaa gtt  aac aaa tac aat gaa  gac ctt gaa caa cag       86641
Arg Glu Gln Lys Val  Asn Lys Tyr Asn Glu  Asp Leu Glu Gln Gln
            2310                 2315              2320
```

```
gtaagtaacg taattttttct ttacatgata aaataatgca taatatcgca agatgttcct  86701
tgcattgtct tatatagata aaaatggact ctattaagaa gacccatcta actgaagggc   86761
accccattca cccatttgct taagccagaa actttggatc atcaacgact tcattctttt   86821
cattctccac atttttctatc attaaatcat gtcagctcta ttttcaaact atatcctaaa  86881
tatgaccact tcttggtatc ttgagacatc actaccagtc ttgtccaagc tattgtttta   86941
tacctgaata actgcaataa tttccaagct ggtatctcag cttccactct tggattattt   87001
cacccctattt ctatttctgg gctgtctcca cacagttgcc aggtaaccct tttaaaacat  87061
aaagcacatc acaaagcaca aagtcctatc ctcagaatct tccagtggtt ctccatcacc   87121
ctaaaataaa acttaaaagt tcttttcata tcccaaaaca acatatgagg tctggcaccc   87181
agttttcttc ccaatctcat cttctactac ttttcccttc atttcattca caatgtttta   87241
accacagtaa ccttctttca gtactttaaa caatccaaac tcgtttaagc gtcaagtcct   87301
tatacttgtt tccttgtttt agaatactgt tcacccaaat attctcatag cttgctccca   87361
gacttcatgt ctctgctgaa atagaggctc cttagagaga ccttccctaa ccctaaccct   87421
aaccctatac tacttgccat cactctttat cctcttaccc tggattattt tttcttgata   87481
gctcttccta ccatctggca ctatattaca tcatatcata ttaaacacac attctttgtg   87541
cttccccact aaacaaggac catgcaagat ggaacattgc cattttgttc actgctgtta   87601
gcctctgtgc ctaggacaat gccagttatg cagtagttac tcaatacttg ttgaatgaat   87661
ggtgaataga acatagaaat ttgcctatgc gtgcttttga aaaccatatt ttaatattac   87721
gctttgttaa aaatgtgtat ctttataaat cctcatattt ccatggcaaa ccttatcttc   87781
taacttttca ttgtcctcaa ag att aag att ctt aaa  cat gtt cct gaa       87830
                        Ile Lys Ile Leu Lys  His Val Pro Glu
                                                 2325
```

```
ggt  gct gag aca gag caa  ggc ctt aaa cgg gag  ctt caa gtt ctt      87875
Gly  Ala Glu Thr Glu Gln  Gly Leu Lys Arg Glu  Leu Gln Val Leu
2330                 2335                 2340
```

| | |
|---|---|
| ag    gtacatcatg tattcatatg actactttgt ttttttcttt aaaaaaaaaa | 87927 |
| Arg | |
| 2345 | |

| | |
|---|---|
| ttattagttt ttatatactc cgaattgcta caactagaga caagcatttt tcgactttac | 87987 |
| tgcctaacag gcttattagg tccttatttc ttccctctaa tgctaatcac tcttttcat | 88047 |
| aatacacact agaaaaaaag gataaaccca actctaagtt tccagtttgt aatttagttt | 88107 |
| aaactttct aagagcatag aatgagttaa accttagctt cccagaggaa aatactaatg | 88167 |
| aaagagaaca agtaatttt ttactttcag gggtctctgt agcctgcttt cattaagctc | 88227 |
| ctcttataac gaaaccacac ttgcaaatgc catcaggtca gatattaaga aaacgtgaa | 88287 |
| ggcttttgta ttccaggctt tttgtttgag aatggtgaca ttgtagcatt gagagtaaat | 88347 |
| gtttacttcg ataaaggcta gcttgttctg attactgtac atcactagtt cataagaaat | 88407 |
| gcccatatat tttatgaagc aatatctgct ttattttttt aacacattat cattgtgttc | 88467 |

| | | |
|---|---|---|
| tag a tta gct aat cat cag  ctg gat aaa gag aaa  gca gaa tta atc | | 88513 |
|     Leu Ala Asn His Gln  Leu Asp Lys Glu Lys  Ala Glu Leu Ile | | |
|              2350                    2355 | | |

| | | |
|---|---|---|
| cat cag ata gaa gct aac  aag gac caa agt gga  gct gaa agc acc | | 88558 |
| His Gln Ile Glu Ala Asn  Lys Asp Gln Ser Gly  Ala Glu Ser Thr | | |
| 2360                2365                       2370 | | |

| | | |
|---|---|---|
| ata cct g gtaatgtatt ttaaaaaaca tgttagctac ccccaagttt ttgaatttgg | | 88615 |
| Ile Pro | | |
| 2375 | | |

| | |
|---|---|
| gtttgccttt tttttttttt tttggctcag atttctgatc attgtctccc tgtaaaatcg | 88675 |
| aattcctgat aagctttggg tcttttgtct ctctgtgcta ttaatataaa aatattccca | 88735 |
| tttttctctt tgtgttgttt atactataga gtagcaagta cccaagtgtt cttctctttg | 88795 |
| ttctccatct gggtgttaca gatttaatca caatacagtg ctaagcaatg aatactaaat | 88855 |
| ctgttgcttc cagtttctaa gtataggctc tttcaagtcc tctgaacatt tttaaaaact | 88915 |
| gcaaataagt aaatactgcc tatattttt tccgtttaca aagtaaaaag aaaatctttc | 88975 |
| tgctccctc cattcccatt caaaagtgat tactaatcat tcctcattcc tgcatataca | 89035 |
| tacacacata ttttgtatac atatatatca cacatatgca tacatgtgtt tgtatgttca | 89095 |
| tatgtacaat gtacatatcc tcattatttg tggattctgt attttctaaa tcacctcctc | 89155 |
| actaaagtgt gtatgtaatc ccaaatcaac actcgcagca catttgcaaa catccacaga | 89215 |
| gccttggaaa gtttgaataa tccaacctac atgtccccag cagaagtcca acaaggcagt | 89275 |
| gctcagtatc ctcatttcag ttttcataga gaaatgagca gaggatggag acagtagagg | 89335 |
| gcagcacagc atagtgcaag aagctgtggc tctggggcct ggtggaaggg atttgaatcc | 89395 |
| caattctgag gcttgttact gctctagcct taggagagtc atgtaacact tctgaatctt | 89455 |
| gttttcttat gtaaataaat agaatttacc aggatgagtt atctttagga tttaagatta | 89515 |
| tcatctgtgt gagatatgta ggtgtatgta tatatgcg tgtatgtata tatgcgtg | 89575 |
| tatgtatata tatgcatgtc tgtacatatt tcccgtagca gcagtggttt gatattcact | 89635 |
| aattgggcta actttataga ccaaaactac tatggataga gaatactttg tttgcattta | 89695 |
| cgtatatata ttttcttggc aagtaacata aaattgaact aatactatac acatttctag | 89755 |
| catatttgcc tttaacagtt tatcatggac atcttttgag gtctgttcat aaattatctc | 89815 |
| atccatttaa taattccata gtgtattatt gcatgtataa gcacatcgaa ccatttatgt | 89875 |
| tttgatggat atttagtttg cttccaagtt tctgcttcta taaaatatga ttaatctatt | 89935 |
| gacctaatta tgccattgtg ataggatgat agagatgcca ttctctccaa aggattatac | 89995 |

```
caatttatat ctgaactatc tttgactatc tcttgtagct ttttcagtat gctatgtagt    90055
cctattacta atttgtaata aaagccatca tgtgtgagtt gtactagaca ctatgctaat    90115
tgccttacaa gcattctata tttacaacca tatatgatag gtattactgt ctccatttta    90175
tgtgataaac aaattcaaag tggttaagta accattccct aagccagcta ggaaatagag    90235
gcaggattaa aatctaaatg tatgaaactc cacagctcct tggcattcct agtccttaac    90295
ccgctatgct atgctacgtc ttggtaacta aaagtacata ttaaatactc tcaaaatatg    90355
tctcatagca gccagcttgg tatgtacact agacacagta ttaatgctgt tgatgtgagg    90415 aaaatttat aattttcctt ccatccatat actaaccagg cccaacagtg cttagcttct    90475
gagatcagag atcaggtgca tgtgcattaa gggtcatatg gccatagata gttctctaat    90535 cttttccattc ctcagtttct taagggaatt tctgaaccct caaaattcct tatttcctaa    90595
gtagacagat tacctgtcat ttttcaaaga ttaaggctta agatcaaacc agaactgttt    90655
tggaaattct aaatcactgt ctatataaat ggcaagataa cttttaagat atttatacca    90715
agcccagtac agtagcacac cacacctgta atcccagcac tttgggaggc tgaagtgggt    90775
ggatcacatg aggtcaggag ttcgagacca ctctggccaa catggtgaaa ccctgtctct    90835
actaaaaata taaaaattag ccaggcatgg tggcacttgc ctgttatccc agctacaagg    90895
gaggctaagg caggagaatc gctttaacct gggaggcagt ggttgttgca gtgagccaag    90955
attgcaccac tgcactctag cctgggcgac agagtgagac tgtctcaaaa aaaaaaaaaa    91015
aaaaaaagat acttgtccca gccatgaaaa tgtttgctgc cccttacttt cgcaaacttt    91075
tagtatttta ttatttttca atggctgtaa aatatgactt attaaatgta gtataatata    91135
aagaaaagag atatctagca aagatagcat taaagcaaaa atcctatttg cctgctgata    91195
aagttagagg tgttaacttg gagggtgaat ccaataaatt agaacttttg tgctatattt    91255
ggagactttt gttttcctac caaagtatca gggctatgtc ttacttatct ttgtattaca    91315
cagcctgcat gacacgtttt gcacatagta attgcacagt aaatgtgtaa taacctacat    91375
ggaatagcca gtgttgtgtt ggatagcggg agcatttggc tagcttatgg ttatagtccc    91435
ttacccaaca gtctgctttt cttctgttgt acttttagta cctaacaagt ttccctggct    91495
ttaggatttt ttccatgtaa aatttctatc atgtgaagaa aaaataactt ggcctacact    91555
tctaatacct agcacatacc tctttctgcc tgctatgaaa ttataatact tgatggaggg    91615
aggcagcatt aagtgtttac atcctgaagt atttcagcca taacatccag tgttttccag    91675
gttctaggtt tcataaaatg tatctctgtt ctctagaaca aatccattac cttgaactca    91735
ttcgtagtgg gaaaaagctg agtctaattt gtatgacttt ttcaacag at gct gat     91791
                                                       Asp Ala Asp caa cta aag gaa aaa ata aaa gat cta gag aca cag ctc aaa atg         91836
Gln Leu Lys Glu Lys Ile Lys Asp Leu Glu Thr Gln Leu Lys Met
2380          2385                2390 tca gat cta gaa aag cag cat ttg aag gtaatattta attatatttt           91883
Ser Asp Leu Glu Lys Gln His Leu Lys
2395              2400 agtatcgttt tgtgaaaaca gctgttgaaa actattttca ttaccatctt taactacgta    91943
tcctaaaaaa ttcagtaata acatcttata tttgacctt atattgcaaa gttaattatg    92003
ttcatctgac tattcctaac atattagagt taacaaaaaa ttcagactca acataggatt    92063
aagtagtaaa tttattttt aattgtaaca aatatatgcc attagtatgt tcttaagttt    92123
tgggtcacat tggcaacagt gtctttattt tttttttgaa attcttttca ggaatcctaa    92183
```

```
ggttatagtt cccttaaaaa aatatttgct gttttacctc ttttaagact gtaaacagga    92243
caaaaaggca tggatatgag aattagctag tgatcactgg ctattctaaa tagtcactaa    92303
ggcttgaatt gtctcttcac cagatgcctg tcagaagtcc caaggtttc cctgatcata     92363 ttaataactt tataaaaaat tgatcattat tcattaaata ttagatatta gtaaggaaaa    92423
tataaatgaa gtctaaacca aaactcttaa ccagactaac ttcaatgtta tgaatcacaa    92483 aatcttttg attgattgct ctattgacaa gctcttatat gcttttagag aaagattaag     92543
tcccattata agagatgata aattttagtc aaagactaga acacaactta cagaatacat    92603
aactggactt gacagttaac aacttagtta tttacactgt acaatggaac aaagaaaaat    92663
cttaattctt ctgcctttat tgctgtattt gaccattcag gaatactttg gctttcatat    92723
ttacaattaa atctccttgt tcaaacgtaa aatatgtata tttcctatat gcaactttta   92783
aagataatgt ttccattag gag gaa ata aag aag ctg aaa aaa gaa ctg        92832
                      Glu Glu Ile Lys Lys Leu Lys Lys Glu Leu
                          2405                2410 gaa aat ttt gat cct tca ttt ttt gaa gaa att gaa gat ctt aag          92877
Glu Asn Phe Asp Pro Ser Phe Phe Glu Glu Ile Glu Asp Leu Lys
    2415                2420                2425 tat aat tac aag gaa gaa gtg aag aag aat att ctc tta gaa gag          92922
Tyr Asn Tyr Lys Glu Glu Val Lys Lys Asn Ile Leu Leu Glu Glu
    2430                2435                2440 aag gta aaa aaa ctt tca gaa caa ttg gga gtt gaa tta act agc          92967
Lys Val Lys Lys Leu Ser Glu Gln Leu Gly Val Glu Leu Thr Ser
    2445                2450                2455 cct gtt gct gct tct gaa gag ttt gaa gat gaa gaa gaa agt cct          93012
Pro Val Ala Ala Ser Glu Glu Phe Glu Asp Glu Glu Glu Ser Pro
    2460                2465                2470 gtt aat ttc ccc att tac taa aggtcaccta taaactttgt ttcatttaac         93063
Val Asn Phe Pro Ile Tyr
    2475 tatttattaa cttataagt taaatatact tggaaataag cagttctccg aactgtagta    93123 tttccttctc actaccttgt accttttatac ttagattgga attcttaata aataaaatta  93183 tatgaaattt tcaacttatt                                                93203

<210> SEQ ID NO 2
<211> LENGTH: 7972
<212> TYPE: DNA
<213> ORGANISM: Homo sapiens
<220> FEATURE:
<221> NAME/KEY: CDS
<222> LOCATION: (345)..(7781)

<400> SEQUENCE: 2
atttgaagtc ctcgttccac gccttctcat catcctgaac accgagctct gggactccgg    60
cggagaatct aaacgtaaag catcacccac ggtcgtgaac tgtaggctct cctggcatcc    120
gggatcttat tctggccttg gcggagttgg ggatggtgtc gcctagcagc cgctgccgct    180
ttggcttgct cgggaccatt tggctggacc cagagtccgc gtggaaccgc gatagggatc    240
tgtcagggcc cgcggccggg tccagcttgg tggttgcggt agtgagaggc ctccgctggt    300
tgccaggctt ggtctagagg tggagcacag tgaaagaatt caag atg cca cct aat    356
                                                 Met Pro Pro Asn
                                                  1 ata aac tgg aaa gaa ata atg aaa gtt gac cca gat gac ctg ccc cgt     404
Ile Asn Trp Lys Glu Ile Met Lys Val Asp Pro Asp Asp Leu Pro Arg
 5              10              15              20
```

```
caa gaa gaa ctg gca gat aat tta ttg att tcc tta tcc aag gtg gaa    452
Gln Glu Glu Leu Ala Asp Asn Leu Leu Ile Ser Leu Ser Lys Val Glu
                25                  30                  35 gta aat gag cta aaa agt gaa aag caa gaa aat gtg ata cac ctt ttc    500
Val Asn Glu Leu Lys Ser Glu Lys Gln Glu Asn Val Ile His Leu Phe
        40                  45                  50 aga att act cag tca cta atg aag atg aaa gct caa gaa gtg gag ctg    548
Arg Ile Thr Gln Ser Leu Met Lys Met Lys Ala Gln Glu Val Glu Leu
                55                  60                  65 gct ttg gaa gaa gta gaa aaa gct gga gaa gaa caa gca aaa ttt gaa    596
Ala Leu Glu Glu Val Glu Lys Ala Gly Glu Glu Gln Ala Lys Phe Glu
        70                  75                  80 aat caa tta aaa act aaa gta atg aaa ctg gaa aat gaa ctg gag atg    644
Asn Gln Leu Lys Thr Lys Val Met Lys Leu Glu Asn Glu Leu Glu Met
85                  90                  95                 100 gct cag cag tct gca ggt gga cga gat act cgg ttt tta cgt aat gaa    692
Ala Gln Gln Ser Ala Gly Gly Arg Asp Thr Arg Phe Leu Arg Asn Glu
                105                 110                 115 att tgc caa ctt gaa aaa caa tta gaa caa aaa gat aga gaa ttg gag    740
Ile Cys Gln Leu Glu Lys Gln Leu Glu Gln Lys Asp Arg Glu Leu Glu
        120                 125                 130 gac atg gaa aag gag ttg gag aaa gag aag aaa gtt aat gag caa ttg    788
Asp Met Glu Lys Glu Leu Glu Lys Glu Lys Lys Val Asn Glu Gln Leu
                135                 140                 145 gct ctt cga aat gag gag gca gaa aat gaa aac agc aaa tta aga aga    836
Ala Leu Arg Asn Glu Glu Ala Glu Asn Glu Asn Ser Lys Leu Arg Arg
        150                 155                 160 gag aac aaa cgt cta aag aaa aag aat gaa caa ctt tgt cag gat att    884
Glu Asn Lys Arg Leu Lys Lys Asn Glu Gln Leu Cys Gln Asp Ile
165                 170                 175                 180 att gac tac cag aaa caa ata gat tca cag aaa gaa aca ctt tta tca    932
Ile Asp Tyr Gln Lys Gln Ile Asp Ser Gln Lys Glu Thr Leu Leu Ser
                185                 190                 195 aga aga ggg gaa gac agt gac tac cga tca cag ttg tct aaa aaa aac    980
Arg Arg Gly Glu Asp Ser Asp Tyr Arg Ser Gln Leu Ser Lys Lys Asn
        200                 205                 210 tat gag ctt atc caa tat ctt gat gaa att cag act tta aca gaa gct   1028
Tyr Glu Leu Ile Gln Tyr Leu Asp Glu Ile Gln Thr Leu Thr Glu Ala
                215                 220                 225 aat gag aaa att gaa gtt cag aat caa gaa atg aga aaa aat tta gaa   1076
Asn Glu Lys Ile Glu Val Gln Asn Gln Glu Met Arg Lys Asn Leu Glu
        230                 235                 240 gag tct gta cag gaa atg gag aag atg act gat gaa tat aat aga atg   1124
Glu Ser Val Gln Glu Met Glu Lys Met Thr Asp Glu Tyr Asn Arg Met
245                 250                 255                 260 aaa gct att gtg cat cag aca gat aat gta ata gat cag tta aaa aaa   1172
Lys Ala Ile Val His Gln Thr Asp Asn Val Ile Asp Gln Leu Lys Lys
                265                 270                 275 gaa aac gat cat tat caa ctt caa gtg cag gag ctt aca gat ctt ctg   1220
Glu Asn Asp His Tyr Gln Leu Gln Val Gln Glu Leu Thr Asp Leu Leu
                280                 285                 290 aaa tca aaa aat gaa gaa gat gat cca att atg gta gct gtc aat gca   1268
Lys Ser Lys Asn Glu Glu Asp Asp Pro Ile Met Val Ala Val Asn Ala
        295                 300                 305 aaa gta gaa gaa tgg aag cta att ttg tct tct aaa gat gat gaa att   1316
Lys Val Glu Glu Trp Lys Leu Ile Leu Ser Ser Lys Asp Asp Glu Ile
                310                 315                 320 att gag tat cag caa atg tta cat aac cta agg gag aaa ctt aag aat   1364
Ile Glu Tyr Gln Gln Met Leu His Asn Leu Arg Glu Lys Leu Lys Asn
```

-continued

```
            325                 330                 335                 340
gct cag ctt gat gct gat aaa agt aat gtt atg gct cta cag cag ggt     1412
Ala Gln Leu Asp Ala Asp Lys Ser Asn Val Met Ala Leu Gln Gln Gly
                    345                 350                 355 ata cag gaa cga gac agt caa att aag atg ctc acc gaa caa gta gaa     1460
Ile Gln Glu Arg Asp Ser Gln Ile Lys Met Leu Thr Glu Gln Val Glu
                360                 365                 370 caa tat aca aaa gaa atg gaa aag aat act tgt att att gaa gat ttg     1508
Gln Tyr Thr Lys Glu Met Glu Lys Asn Thr Cys Ile Ile Glu Asp Leu
            375                 380                 385 aaa aat gag ctc caa aga aac aaa ggt gct tca acc ctt tct caa cag     1556
Lys Asn Glu Leu Gln Arg Asn Lys Gly Ala Ser Thr Leu Ser Gln Gln
        390                 395                 400 act cat atg aaa att cag tca acg tta gac att tta aaa gag aaa act     1604
Thr His Met Lys Ile Gln Ser Thr Leu Asp Ile Leu Lys Glu Lys Thr
405                 410                 415                 420 aaa gag gct gag aga aca gct gaa ctg gct gag gct gat gct agg gaa     1652
Lys Glu Ala Glu Arg Thr Ala Glu Leu Ala Glu Ala Asp Ala Arg Glu
                    425                 430                 435 aag gat aaa gaa tta gtt gag gct ctg aag agg tta aaa gat tat gaa     1700
Lys Asp Lys Glu Leu Val Glu Ala Leu Lys Arg Leu Lys Asp Tyr Glu
                440                 445                 450 tcg gga gta tat ggt tta gaa gat gct gtc gtt gaa ata aag aat tgt     1748
Ser Gly Val Tyr Gly Leu Glu Asp Ala Val Val Glu Ile Lys Asn Cys
            455                 460                 465 aaa aac caa att aaa ata aga gat cga gag att gaa ata tta aca aag     1796
Lys Asn Gln Ile Lys Ile Arg Asp Arg Glu Ile Glu Ile Leu Thr Lys
        470                 475                 480 gaa atc aat aaa ctt gaa ttg aag atc agt gat ttc ctt gat gaa aat     1844
Glu Ile Asn Lys Leu Glu Leu Lys Ile Ser Asp Phe Leu Asp Glu Asn
485                 490                 495                 500 gag gca ctt aga gag cgt gtg ggc ctt gaa cca aag aca atg att gat     1892
Glu Ala Leu Arg Glu Arg Val Gly Leu Glu Pro Lys Thr Met Ile Asp
                    505                 510                 515 tta act gaa ttt aga aat agc aaa cac tta aaa cag cag cag tac aga     1940
Leu Thr Glu Phe Arg Asn Ser Lys His Leu Lys Gln Gln Gln Tyr Arg
                520                 525                 530 gct gaa aac cag att ctt ttg aaa gag att gaa agt cta gag gaa gaa     1988
Ala Glu Asn Gln Ile Leu Leu Lys Glu Ile Glu Ser Leu Glu Glu Glu
            535                 540                 545 cga ctt gat ctg aaa aaa aaa att cgt caa atg gct caa gaa aga gga     2036
Arg Leu Asp Leu Lys Lys Lys Ile Arg Gln Met Ala Gln Glu Arg Gly
        550                 555                 560 aaa aga agt gca act tca gga tta acc act gag gac ctg aac cta act     2084
Lys Arg Ser Ala Thr Ser Gly Leu Thr Thr Glu Asp Leu Asn Leu Thr
565                 570                 575                 580 gaa aac att tct caa gga gat aga ata agt gaa aga aaa ttg gat tta     2132
Glu Asn Ile Ser Gln Gly Asp Arg Ile Ser Glu Arg Lys Leu Asp Leu
                    585                 590                 595 ttg agc ctc aaa aat atg agt gaa gca caa tca aag aat gaa ttt ctt     2180
Leu Ser Leu Lys Asn Met Ser Glu Ala Gln Ser Lys Asn Glu Phe Leu
                600                 605                 610 tca aga gaa cta att gaa aaa gaa aga gat tta gaa agg agt agg aca     2228
Ser Arg Glu Leu Ile Glu Lys Glu Arg Asp Leu Glu Arg Ser Arg Thr
            615                 620                 625 gtg ata gcc aaa ttt cag aat aaa tta aaa gaa tta gtt gaa gaa aat     2276
Val Ile Ala Lys Phe Gln Asn Lys Leu Lys Glu Leu Val Glu Glu Asn
        630                 635                 640 aag caa ctt gaa gaa ggt atg aaa gaa ata ttg caa gca att aag gaa     2324
```

```
           Lys Gln Leu Glu Glu Gly Met Lys Glu Ile Leu Gln Ala Ile Lys Glu
           645                 650                 655                 660 atg cag aaa gat cct gat gtt aaa gga gga gaa aca tct cta att atc      2372
           Met Gln Lys Asp Pro Asp Val Lys Gly Gly Glu Thr Ser Leu Ile Ile
                           665                 670                 675 cct agc ctt gaa aga cta gtt aat gct ata gaa tca aag aat gca gaa      2420
           Pro Ser Leu Glu Arg Leu Val Asn Ala Ile Glu Ser Lys Asn Ala Glu
                       680                 685                 690 gga atc ttt gat gcg agt ctg cat ttg aaa gcc caa gtt gat cag ctt      2468
           Gly Ile Phe Asp Ala Ser Leu His Leu Lys Ala Gln Val Asp Gln Leu
                   695                 700                 705 acc gga aga aat gaa gaa tta aga cag gag ctc agg gaa tct cgg aaa      2516
           Thr Gly Arg Asn Glu Glu Leu Arg Gln Glu Leu Arg Glu Ser Arg Lys
               710                 715                 720 gag gct ata aat tat tca cag cag ttg gca aaa gct aat tta aag ata      2564
           Glu Ala Ile Asn Tyr Ser Gln Gln Leu Ala Lys Ala Asn Leu Lys Ile
           725                 730                 735                 740 gac cat ctt gaa aaa gaa act agt ctt tta cga caa tca gaa gga tcg      2612
           Asp His Leu Glu Lys Glu Thr Ser Leu Leu Arg Gln Ser Glu Gly Ser
                           745                 750                 755 aat gtt gtt ttt aaa gga att gac tta cct gat ggg ata gca cca tct      2660
           Asn Val Val Phe Lys Gly Ile Asp Leu Pro Asp Gly Ile Ala Pro Ser
                       760                 765                 770 agt gcc agt atc att aat tct cag aat gaa tat tta ata cat ttg tta      2708
           Ser Ala Ser Ile Ile Asn Ser Gln Asn Glu Tyr Leu Ile His Leu Leu
                   775                 780                 785 cag gaa cta gaa aat aaa gaa aaa aag tta aag aat tta gaa gat tct      2756
           Gln Glu Leu Glu Asn Lys Glu Lys Lys Leu Lys Asn Leu Glu Asp Ser
               790                 795                 800 ctt gaa gat tac aac aga aaa ttt gct gta att cgt cat caa caa agt      2804
           Leu Glu Asp Tyr Asn Arg Lys Phe Ala Val Ile Arg His Gln Gln Ser
           805                 810                 815                 820 ttg ttg tat aaa gaa tac cta agt gaa aag gag acc tgg aaa aca gaa      2852
           Leu Leu Tyr Lys Glu Tyr Leu Ser Glu Lys Glu Thr Trp Lys Thr Glu
                           825                 830                 835 tct aaa aca ata aaa gag gaa aag aga aaa ctt gag gat caa gtc caa      2900
           Ser Lys Thr Ile Lys Glu Glu Lys Arg Lys Leu Glu Asp Gln Val Gln
                       840                 845                 850 caa gat gct ata aaa gta aaa gaa tat aat aat ttg ctc aat gct ctt      2948
           Gln Asp Ala Ile Lys Val Lys Glu Tyr Asn Asn Leu Leu Asn Ala Leu
                   855                 860                 865 cag atg gat tcg gat gaa atg aaa aaa ata ctt gca gaa aat agt agg      2996
           Gln Met Asp Ser Asp Glu Met Lys Lys Ile Leu Ala Glu Asn Ser Arg
               870                 875                 880 aaa att act gtt ttg caa gtg aat gaa aaa tca ctt ata agg caa tat      3044
           Lys Ile Thr Val Leu Gln Val Asn Glu Lys Ser Leu Ile Arg Gln Tyr
           885                 890                 895                 900 aca acc tta gta gaa ttg gag cga caa ctt aga aaa gaa aat gag aag      3092
           Thr Thr Leu Val Glu Leu Glu Arg Gln Leu Arg Lys Glu Asn Glu Lys
                           905                 910                 915 caa aag aat gaa ttg ttg tca atg gag gct gaa gtt tgt gaa aaa att      3140
           Gln Lys Asn Glu Leu Leu Ser Met Glu Ala Glu Val Cys Glu Lys Ile
                       920                 925                 930 ggg tgt ttg caa aga ttt aag gaa atg gcc att ttc aag att gca gct      3188
           Gly Cys Leu Gln Arg Phe Lys Glu Met Ala Ile Phe Lys Ile Ala Ala
                   935                 940                 945 ctc caa aaa gtt gta gat aat agt gtt tct ttg tct gaa cta gaa ctg      3236
           Leu Gln Lys Val Val Asp Asn Ser Val Ser Leu Ser Glu Leu Glu Leu
               950                 955                 960
```

|   |   |   |   |   |   |   |   |   |   |   |   |   |   |   |
|---|---|---|---|---|---|---|---|---|---|---|---|---|---|---|
| gct | aat | aaa | cag | tac | aat | gaa | ctg | act | gct | aag | tac | agg | gac | atc | ttg | 3284 |
| Ala | Asn | Lys | Gln | Tyr | Asn | Glu | Leu | Thr | Ala | Lys | Tyr | Arg | Asp | Ile | Leu |
| 965 |   |   |   |   | 970 |   |   |   |   | 975 |   |   |   |   | 980 |

```
gct aat aaa cag tac aat gaa ctg act gct aag tac agg gac atc ttg    3284
Ala Asn Lys Gln Tyr Asn Glu Leu Thr Ala Lys Tyr Arg Asp Ile Leu
965                 970                 975                 980 caa aaa gat aat atg ctt gtt caa aga aca agt aac ttg gaa cac ctg    3332
Gln Lys Asp Asn Met Leu Val Gln Arg Thr Ser Asn Leu Glu His Leu
            985                 990                 995 gag tgt gaa aac atc tcc tta aaa gaa caa gtg gag tct ata aat        3377
Glu Cys Glu Asn Ile Ser Leu Lys Glu Gln Val Glu Ser Ile Asn
1000                1005                1010 aaa gaa ctg gag att acc aag gaa aaa ctt cac act att gaa caa        3422
Lys Glu Leu Glu Ile Thr Lys Glu Lys Leu His Thr Ile Glu Gln
        1015                1020                1025 gcc tgg gaa cag gaa act aaa tta ggt aat gaa tct agc atg gat        3467
Ala Trp Glu Gln Glu Thr Lys Leu Gly Asn Glu Ser Ser Met Asp
        1030                1035                1040 aag gca aag aaa tca ata acc aac agt gac att gtt tcc att tca        3512
Lys Ala Lys Lys Ser Ile Thr Asn Ser Asp Ile Val Ser Ile Ser
        1045                1050                1055 aaa aaa ata act atg ctg gaa atg aag gaa tta aat gaa agg cag        3557
Lys Lys Ile Thr Met Leu Glu Met Lys Glu Leu Asn Glu Arg Gln
        1060                1065                1070 cgg gct gaa cat tgt caa aaa atg tat gaa cac tta cgg act tcg        3602
Arg Ala Glu His Cys Gln Lys Met Tyr Glu His Leu Arg Thr Ser
        1075                1080                1085 tta aag caa atg gag gaa cgt aat ttt gaa ttg gaa acc aaa ttt        3647
Leu Lys Gln Met Glu Glu Arg Asn Phe Glu Leu Glu Thr Lys Phe
        1090                1095                1100 gct gag ctt acc aaa atc aat ttg gat gca cag aag gtg gaa cag        3692
Ala Glu Leu Thr Lys Ile Asn Leu Asp Ala Gln Lys Val Glu Gln
        1105                1110                1115 atg tta aga gat gaa tta gct gat agt gtg agc aag gca gta agt        3737
Met Leu Arg Asp Glu Leu Ala Asp Ser Val Ser Lys Ala Val Ser
        1120                1125                1130 gat gct gat agg caa cgg att cta gaa tta gag aag aat gaa atg        3782
Asp Ala Asp Arg Gln Arg Ile Leu Glu Leu Glu Lys Asn Glu Met
        1135                1140                1145 gaa cta aaa gtt gaa gtg tca aaa ctg aga gag att tct gat att        3827
Glu Leu Lys Val Glu Val Ser Lys Leu Arg Glu Ile Ser Asp Ile
        1150                1155                1160 gcc aga aga caa gtt gaa att ttg aat gca caa caa caa tct agg        3872
Ala Arg Arg Gln Val Glu Ile Leu Asn Ala Gln Gln Gln Ser Arg
        1165                1170                1175 gac aag gaa gta gag tcc ctc aga atg caa ctg cta gac tat cag        3917
Asp Lys Glu Val Glu Ser Leu Arg Met Gln Leu Leu Asp Tyr Gln
        1180                1185                1190 gca cag tct gat gaa aag tcg ctc att gcc aag ttg cac caa cat        3962
Ala Gln Ser Asp Glu Lys Ser Leu Ile Ala Lys Leu His Gln His
        1195                1200                1205 aat gtc tct ctt caa ctg agt gag gct act gct ctt ggt aag ttg        4007
Asn Val Ser Leu Gln Leu Ser Glu Ala Thr Ala Leu Gly Lys Leu
        1210                1215                1220 gag tca att aca tct aaa ctg cag aag atg gag gcc tac aac ttg        4052
Glu Ser Ile Thr Ser Lys Leu Gln Lys Met Glu Ala Tyr Asn Leu
        1225                1230                1235 cgc tta gag cag aaa ctt gat gaa aaa gaa cag gct ctc tat tat        4097
Arg Leu Glu Gln Lys Leu Asp Glu Lys Glu Gln Ala Leu Tyr Tyr
        1240                1245                1250 gct cgt ttg gag gga aga aac aga gca aaa cat ctg cgc caa aca        4142
Ala Arg Leu Glu Gly Arg Asn Arg Ala Lys His Leu Arg Gln Thr
        1255                1260                1265
```

-continued

| | | |
|---|---|---|
| att cag tct cta cga cga cag ttt agt gga gct tta ccc ttg gca<br>Ile Gln Ser Leu Arg Arg Gln Phe Ser Gly Ala Leu Pro Leu Ala<br>1270                        1275                        1280 | 4187 |
| caa cag gaa aag ttc tcc aaa aca atg att caa cta caa aat gac<br>Gln Gln Glu Lys Phe Ser Lys Thr Met Ile Gln Leu Gln Asn Asp<br>1285                        1290                        1295 | 4232 |
| aaa ctt aag ata atg caa gaa atg aaa aat tct caa caa gaa cat<br>Lys Leu Lys Ile Met Gln Glu Met Lys Asn Ser Gln Gln Glu His<br>1300                        1305                        1310 | 4277 |
| aga aat atg gag aac aaa aca ttg gag atg gaa tta aaa tta aag<br>Arg Asn Met Glu Asn Lys Thr Leu Glu Met Glu Leu Lys Leu Lys<br>1315                        1320                        1325 | 4322 |
| ggc ctg gaa gag tta ata agc act tta aag gat acc aaa gga gcc<br>Gly Leu Glu Glu Leu Ile Ser Thr Leu Lys Asp Thr Lys Gly Ala<br>1330                        1335                        1340 | 4367 |
| caa aag gta atc aac tgg cat atg aaa ata gaa gaa ctt cgt ctt<br>Gln Lys Val Ile Asn Trp His Met Lys Ile Glu Glu Leu Arg Leu<br>1345                        1350                        1355 | 4412 |
| caa gaa ctt aaa cta aat cgg gaa tta gtc aag gat aaa gaa gaa<br>Gln Glu Leu Lys Leu Asn Arg Glu Leu Val Lys Asp Lys Glu Glu<br>1360                        1365                        1370 | 4457 |
| ata aaa tat ttg aat aac ata att tct gaa tat gaa cgt aca atc<br>Ile Lys Tyr Leu Asn Asn Ile Ile Ser Glu Tyr Glu Arg Thr Ile<br>1375                        1380                        1385 | 4502 |
| agc agt ctt gaa gaa gaa att gtg caa cag aac aag ttt cat gaa<br>Ser Ser Leu Glu Glu Glu Ile Val Gln Gln Asn Lys Phe His Glu<br>1390                        1395                        1400 | 4547 |
| gaa aga caa atg gcc tgg gat caa aga gaa gtt gac ctg gaa cgc<br>Glu Arg Gln Met Ala Trp Asp Gln Arg Glu Val Asp Leu Glu Arg<br>1405                        1410                        1415 | 4592 |
| caa cta gac att ttt gac cgt cag caa aat gaa ata cta aat gcg<br>Gln Leu Asp Ile Phe Asp Arg Gln Gln Asn Glu Ile Leu Asn Ala<br>1420                        1425                        1430 | 4637 |
| gca caa aag ttt gaa gaa gct aca gga tca atc cct gac cct agt<br>Ala Gln Lys Phe Glu Glu Ala Thr Gly Ser Ile Pro Asp Pro Ser<br>1435                        1440                        1445 | 4682 |
| ttg ccc ctt cca aat caa ctt gag atc gct cta agg aaa att aag<br>Leu Pro Leu Pro Asn Gln Leu Glu Ile Ala Leu Arg Lys Ile Lys<br>1450                        1455                        1460 | 4727 |
| gag aac att cga ata att cta gaa aca cgg gca act tgc aaa tca<br>Glu Asn Ile Arg Ile Ile Leu Glu Thr Arg Ala Thr Cys Lys Ser<br>1465                        1470                        1475 | 4772 |
| cta gaa gag aaa cta aaa gag aaa gaa tct gct tta agg tta gca<br>Leu Glu Glu Lys Leu Lys Glu Lys Glu Ser Ala Leu Arg Leu Ala<br>1480                        1485                        1490 | 4817 |
| gaa caa aat ata ctg tca aga gac aaa gta atc aat gaa ctg agg<br>Glu Gln Asn Ile Leu Ser Arg Asp Lys Val Ile Asn Glu Leu Arg<br>1495                        1500                        1505 | 4862 |
| ctt cga ttg cct gcc act gca gaa aga gaa aag ctc ata gct gag<br>Leu Arg Leu Pro Ala Thr Ala Glu Arg Glu Lys Leu Ile Ala Glu<br>1510                        1515                        1520 | 4907 |
| cta ggc aga aaa gag atg gaa cca aaa tct cac cac aca ttg aaa<br>Leu Gly Arg Lys Glu Met Glu Pro Lys Ser His His Thr Leu Lys<br>1525                        1530                        1535 | 4952 |
| att gct cat caa acc att gca aac atg caa gca agg tta aat caa<br>Ile Ala His Gln Thr Ile Ala Asn Met Gln Ala Arg Leu Asn Gln<br>1540                        1545                        1550 | 4997 |
| aaa gaa gaa gta tta aag aag tat caa cgt ctt cta gaa aaa gcc<br>Lys Glu Glu Val Leu Lys Lys Tyr Gln Arg Leu Leu Glu Lys Ala | 5042 |

-continued

|  |  |  |  |  |  |  |  |  |  |  |  |
|---|---|---|---|---|---|---|---|---|---|---|---|
|  |  | 1555 |  |  | 1560 |  |  | 1565 |  |  |  |
| aga | gag | gag | caa | aga | gaa | att | gtg | aag | aaa | cat | gag | gaa | gac | ctt | 5087 |
| Arg | Glu | Glu | Gln | Arg | Glu | Ile | Val | Lys | Lys | His | Glu | Glu | Asp | Leu |  |
|  |  | 1570 |  |  |  | 1575 |  |  |  | 1580 |  |  |
| cat | att | ctt | cat | cac | aga | tta | gaa | cta | cag | gct | gat | agt | tca | cta | 5132 |
| His | Ile | Leu | His | His | Arg | Leu | Glu | Leu | Gln | Ala | Asp | Ser | Ser | Leu |  |
|  |  | 1585 |  |  |  | 1590 |  |  |  | 1595 |  |  |
| aat | aaa | ttc | aaa | caa | acg | gct | tgg | gat | tta | atg | aaa | cag | tct | ccc | 5177 |
| Asn | Lys | Phe | Lys | Gln | Thr | Ala | Trp | Asp | Leu | Met | Lys | Gln | Ser | Pro |  |
|  |  | 1600 |  |  |  | 1605 |  |  |  | 1610 |  |  |
| act | cca | gtt | cct | acc | aac | aag | cat | ttt | att | cgt | ctg | gct | gag | atg | 5222 |
| Thr | Pro | Val | Pro | Thr | Asn | Lys | His | Phe | Ile | Arg | Leu | Ala | Glu | Met |  |
|  |  | 1615 |  |  |  | 1620 |  |  |  | 1625 |  |  |
| gaa | cag | aca | gta | gca | gaa | caa | gat | gac | tct | ctt | tcc | tca | ctc | ttg | 5267 |
| Glu | Gln | Thr | Val | Ala | Glu | Gln | Asp | Asp | Ser | Leu | Ser | Ser | Leu | Leu |  |
|  |  | 1630 |  |  |  | 1635 |  |  |  | 1640 |  |  |
| gtc | aaa | cta | aag | aaa | gta | tca | caa | gat | ttg | gag | aga | caa | aga | gaa | 5312 |
| Val | Lys | Leu | Lys | Lys | Val | Ser | Gln | Asp | Leu | Glu | Arg | Gln | Arg | Glu |  |
|  |  | 1645 |  |  |  | 1650 |  |  |  | 1655 |  |  |
| atc | act | gaa | tta | aaa | gta | aaa | gaa | ttt | gaa | aat | atc | aaa | tta | cag | 5357 |
| Ile | Thr | Glu | Leu | Lys | Val | Lys | Glu | Phe | Glu | Asn | Ile | Lys | Leu | Gln |  |
|  |  | 1660 |  |  |  | 1665 |  |  |  | 1670 |  |  |
| ctt | caa | gaa | aac | cat | gaa | gat | gaa | gtg | aaa | aaa | gta | aaa | gcg | gaa | 5402 |
| Leu | Gln | Glu | Asn | His | Glu | Asp | Glu | Val | Lys | Lys | Val | Lys | Ala | Glu |  |
|  |  | 1675 |  |  |  | 1680 |  |  |  | 1685 |  |  |
| gta | gag | gat | tta | aag | tat | ctt | ctg | gac | cag | tca | caa | aag | gag | tca | 5447 |
| Val | Glu | Asp | Leu | Lys | Tyr | Leu | Leu | Asp | Gln | Ser | Gln | Lys | Glu | Ser |  |
|  |  | 1690 |  |  |  | 1695 |  |  |  | 1700 |  |  |
| cag | tgt | tta | aaa | tct | gaa | ctt | cag | gct | caa | aaa | gaa | gca | aat | tca | 5492 |
| Gln | Cys | Leu | Lys | Ser | Glu | Leu | Gln | Ala | Gln | Lys | Glu | Ala | Asn | Ser |  |
|  |  | 1705 |  |  |  | 1710 |  |  |  | 1715 |  |  |
| aga | gct | cca | aca | act | aca | atg | aga | aat | cta | gta | gaa | cgg | cta | aag | 5537 |
| Arg | Ala | Pro | Thr | Thr | Thr | Met | Arg | Asn | Leu | Val | Glu | Arg | Leu | Lys |  |
|  |  | 1720 |  |  |  | 1725 |  |  |  | 1730 |  |  |
| agc | caa | tta | gcc | ttg | aag | gag | aaa | caa | cag | aaa | gca | ctt | agt | cgg | 5582 |
| Ser | Gln | Leu | Ala | Leu | Lys | Glu | Lys | Gln | Gln | Lys | Ala | Leu | Ser | Arg |  |
|  |  | 1735 |  |  |  | 1740 |  |  |  | 1745 |  |  |
| gca | ctt | tta | gaa | ctc | cgg | gca | gaa | atg | aca | gca | gct | gct | gaa | gaa | 5627 |
| Ala | Leu | Leu | Glu | Leu | Arg | Ala | Glu | Met | Thr | Ala | Ala | Ala | Glu | Glu |  |
|  |  | 1750 |  |  |  | 1755 |  |  |  | 1760 |  |  |
| cgt | att | att | tct | gca | act | tct | caa | aaa | gag | gcc | cat | ctc | aat | gtt | 5672 |
| Arg | Ile | Ile | Ser | Ala | Thr | Ser | Gln | Lys | Glu | Ala | His | Leu | Asn | Val |  |
|  |  | 1765 |  |  |  | 1770 |  |  |  | 1775 |  |  |
| caa | caa | atc | gtt | gat | cga | cat | act | aga | gag | cta | aag | aca | caa | gtt | 5717 |
| Gln | Gln | Ile | Val | Asp | Arg | His | Thr | Arg | Glu | Leu | Lys | Thr | Gln | Val |  |
|  |  | 1780 |  |  |  | 1785 |  |  |  | 1790 |  |  |
| gaa | gat | tta | aat | gaa | aat | ctt | tta | aaa | ttg | aaa | gaa | gca | ctt | aaa | 5762 |
| Glu | Asp | Leu | Asn | Glu | Asn | Leu | Leu | Lys | Leu | Lys | Glu | Ala | Leu | Lys |  |
|  |  | 1795 |  |  |  | 1800 |  |  |  | 1805 |  |  |
| aca | agt | aaa | aac | aga | gaa | aac | tca | cta | act | gat | aat | ttg | aat | gac | 5807 |
| Thr | Ser | Lys | Asn | Arg | Glu | Asn | Ser | Leu | Thr | Asp | Asn | Leu | Asn | Asp |  |
|  |  | 1810 |  |  |  | 1815 |  |  |  | 1820 |  |  |
| tta | aat | aat | gaa | ctg | caa | aag | aaa | caa | aaa | gcc | tat | aat | aaa | ata | 5852 |
| Leu | Asn | Asn | Glu | Leu | Gln | Lys | Lys | Gln | Lys | Ala | Tyr | Asn | Lys | Ile |  |
|  |  | 1825 |  |  |  | 1830 |  |  |  | 1835 |  |  |
| ctt | aga | gag | aaa | gag | gaa | att | gat | caa | gag | aat | gat | gaa | ctg | aaa | 5897 |
| Leu | Arg | Glu | Lys | Glu | Glu | Ile | Asp | Gln | Glu | Asn | Asp | Glu | Leu | Lys |  |
|  |  | 1840 |  |  |  | 1845 |  |  |  | 1850 |  |  |
| agg | caa | att | aaa | aga | cta | acc | agt | gga | tta | cag | ggc | aaa | ccc | ctg | 5942 |

```
Arg Gln Ile Lys   Arg Leu Thr Ser Gly   Leu Gln Gly Lys Pro   Leu
         1855              1860                  1865 aca gat aat aaa   caa agt cta att gaa   gaa ctc caa agg aaa   gtt       5987
Thr Asp Asn Lys   Gln Ser Leu Ile Glu   Glu Leu Gln Arg Lys   Val
         1870              1875                  1880 aaa aaa cta gag   aac caa tta gag gga   aag gtg gag gaa gta   gac       6032
Lys Lys Leu Glu   Asn Gln Leu Glu Gly   Lys Val Glu Glu Val   Asp
         1885              1890                  1895 cta aaa cct atg   aaa gaa aag aat gct   aaa gaa gaa tta att   agg       6077
Leu Lys Pro Met   Lys Glu Lys Asn Ala   Lys Glu Glu Leu Ile   Arg
         1900              1905                  1910 tgg gaa gaa ggt   aaa aag tgg caa gcc   aaa ata gaa gga att   cga       6122
Trp Glu Glu Gly   Lys Lys Trp Gln Ala   Lys Ile Glu Gly Ile   Arg
         1915              1920                  1925 aac aag tta aaa   gag aaa gag ggg gaa   gtc ttt act tta aca   aag       6167
Asn Lys Leu Lys   Glu Lys Glu Gly Glu   Val Phe Thr Leu Thr   Lys
         1930              1935                  1940 cag ttg aat act   ttg aag gat ctt ttt   gcc aaa gcc gat aaa   gag       6212
Gln Leu Asn Thr   Leu Lys Asp Leu Phe   Ala Lys Ala Asp Lys   Glu
         1945              1950                  1955 aaa ctt act ttg   cag agg aaa cta aaa   aca act ggc atg act   gtt       6257
Lys Leu Thr Leu   Gln Arg Lys Leu Lys   Thr Thr Gly Met Thr   Val
         1960              1965                  1970 gat cag gtt ttg   gga ata cga gct ttg   gag tca gaa aaa gaa   ttg       6302
Asp Gln Val Leu   Gly Ile Arg Ala Leu   Glu Ser Glu Lys Glu   Leu
         1975              1980                  1985 gaa gaa tta aaa   aag aga aat ctt gac   tta gaa aat gat ata   ttg       6347
Glu Glu Leu Lys   Lys Arg Asn Leu Asp   Leu Glu Asn Asp Ile   Leu
         1990              1995                  2000 tat atg agg gcc   cac caa gct ctt cct   cga gat tct gtt gta   gaa       6392
Tyr Met Arg Ala   His Gln Ala Leu Pro   Arg Asp Ser Val Val   Glu
         2005              2010                  2015 gat tta cat tta   caa aat aga tac ctc   caa gaa aaa ctt cat   gct       6437
Asp Leu His Leu   Gln Asn Arg Tyr Leu   Gln Glu Lys Leu His   Ala
         2020              2025                  2030 tta gaa aaa cag   ttt tca aag gat aca   tat tct aag cct tca   att       6482
Leu Glu Lys Gln   Phe Ser Lys Asp Thr   Tyr Ser Lys Pro Ser   Ile
         2035              2040                  2045 tca gga ata gag   tca gat gat cat tgt   cag aga gaa cag gag   ctt       6527
Ser Gly Ile Glu   Ser Asp Asp His Cys   Gln Arg Glu Gln Glu   Leu
         2050              2055                  2060 cag aag gaa aac   ttg aag ttg tca tct   gaa aat att gaa ctg   aaa       6572
Gln Lys Glu Asn   Leu Lys Leu Ser Ser   Glu Asn Ile Glu Leu   Lys
         2065              2070                  2075 ttt cag ctt gaa   caa gca aat aaa gat   ttg cca aga tta aag   aat       6617
Phe Gln Leu Glu   Gln Ala Asn Lys Asp   Leu Pro Arg Leu Lys   Asn
         2080              2085                  2090 caa gtc aga gat   ttg aag gaa atg tgt   gaa ttt ctt aag aaa   gaa       6662
Gln Val Arg Asp   Leu Lys Glu Met Cys   Glu Phe Leu Lys Lys   Glu
         2095              2100                  2105 aaa gca gaa gtt   cag cgg aaa ctt ggc   cat gtt aga ggg tct   ggt       6707
Lys Ala Glu Val   Gln Arg Lys Leu Gly   His Val Arg Gly Ser   Gly
         2110              2115                  2120 aga agt gga aag   aca atc cca gaa ctg   gaa aaa acc att ggt   tta       6752
Arg Ser Gly Lys   Thr Ile Pro Glu Leu   Glu Lys Thr Ile Gly   Leu
         2125              2130                  2135 atg aaa aaa gta   gtt gaa aaa gtc cag   aga gaa aat gaa cag   ttg       6797
Met Lys Lys Val   Val Glu Lys Val Gln   Arg Glu Asn Glu Gln   Leu
         2140              2145                  2150
```

-continued

| | | | | | | | | | | | | |
|---|---|---|---|---|---|---|---|---|---|---|---|---|
| aaa | aaa | gca | tca | gga | ata | ttg | act | agt | gaa | aaa | atg | gct | aat | att | 6842 |
| Lys | Lys | Ala | Ser 2155 | Gly | Ile | Leu | Thr | Ser 2160 | Glu | Lys | Met | Ala 2165 | Asn | Ile | |

```
aaa aaa gca tca gga ata ttg act agt gaa aaa atg gct aat att      6842
Lys Lys Ala Ser Gly Ile Leu Thr Ser Glu Lys Met Ala Asn Ile
            2155            2160            2165 gag cag gaa aat gaa aaa ttg aag gct gaa tta gaa aaa ctt aaa      6887
Glu Gln Glu Asn Glu Lys Leu Lys Ala Glu Leu Glu Lys Leu Lys
            2170            2175            2180 gct cat ctt ggg cat cag ttg agc atg cac tat gaa tcc aag acc      6932
Ala His Leu Gly His Gln Leu Ser Met His Tyr Glu Ser Lys Thr
            2185            2190            2195 aaa ggc aca gaa aaa att att gct gaa aat gaa agg ctt cgt aaa      6977
Lys Gly Thr Glu Lys Ile Ile Ala Glu Asn Glu Arg Leu Arg Lys
            2200            2205            2210 gaa ctt aaa aaa gaa act gat gct gca gag aaa tta cgg ata gca      7022
Glu Leu Lys Lys Glu Thr Asp Ala Ala Glu Lys Leu Arg Ile Ala
            2215            2220            2225 aag aat aat tta gag ata tta aat gag aag atg aca gtt caa cta      7067
Lys Asn Asn Leu Glu Ile Leu Asn Glu Lys Met Thr Val Gln Leu
            2230            2235            2240 gaa gag act ggt aag aga ttg cag ttt gca gaa agc aga ggt cca      7112
Glu Glu Thr Gly Lys Arg Leu Gln Phe Ala Glu Ser Arg Gly Pro
            2245            2250            2255 cag ctt gaa ggt gct gac agt aag agc tgg aaa tcc att gtg gtt      7157
Gln Leu Glu Gly Ala Asp Ser Lys Ser Trp Lys Ser Ile Val Val
            2260            2265            2270 aca aga atg tat gaa acc aag tta aaa gaa ttg gaa act gat att      7202
Thr Arg Met Tyr Glu Thr Lys Leu Lys Glu Leu Glu Thr Asp Ile
            2275            2280            2285 gcc aaa aaa aat caa agc att act gac ctt aaa cag ctt gta aaa      7247
Ala Lys Lys Asn Gln Ser Ile Thr Asp Leu Lys Gln Leu Val Lys
            2290            2295            2300 gaa gca aca gag aga gaa caa aaa gtt aac aaa tac aat gaa gac      7292
Glu Ala Thr Glu Arg Glu Gln Lys Val Asn Lys Tyr Asn Glu Asp
            2305            2310            2315 ctt gaa caa cag att aag att ctt aaa cat gtt cct gaa ggt gct      7337
Leu Glu Gln Gln Ile Lys Ile Leu Lys His Val Pro Glu Gly Ala
            2320            2325            2330 gag aca gag caa ggc ctt aaa cgg gag ctt caa gtt ctt aga tta      7382
Glu Thr Glu Gln Gly Leu Lys Arg Glu Leu Gln Val Leu Arg Leu
            2335            2340            2345 gct aat cat cag ctg gat aaa gag aaa gca gaa tta atc cat cag      7427
Ala Asn His Gln Leu Asp Lys Glu Lys Ala Glu Leu Ile His Gln
            2350            2355            2360 ata gaa gct aac aag gac caa agt gga gct gaa agc acc ata cct      7472
Ile Glu Ala Asn Lys Asp Gln Ser Gly Ala Glu Ser Thr Ile Pro
            2365            2370            2375 gat gct gat caa cta aag gaa aaa ata aaa gat cta gag aca cag      7517
Asp Ala Asp Gln Leu Lys Glu Lys Ile Lys Asp Leu Glu Thr Gln
            2380            2385            2390 ctc aaa atg tca gat cta gaa aag cag cat ttg aag gag gaa ata      7562
Leu Lys Met Ser Asp Leu Glu Lys Gln His Leu Lys Glu Glu Ile
            2395            2400            2405 aag aag ctg aaa aaa gaa ctg gaa aat ttt gat cct tca ttt ttt      7607
Lys Lys Leu Lys Lys Glu Leu Glu Asn Phe Asp Pro Ser Phe Phe
            2410            2415            2420 gaa gaa att gaa gat ctt aag tat aat tac aag gaa gaa gtg aag      7652
Glu Glu Ile Glu Asp Leu Lys Tyr Asn Tyr Lys Glu Glu Val Lys
            2425            2430            2435 aag aat att ctc tta gaa gag aag gta aaa aaa ctt tca gaa caa      7697
Lys Asn Ile Leu Leu Glu Glu Lys Val Lys Lys Leu Ser Glu Gln
            2440            2445            2450
```

-continued

```
ttg gga gtt gaa tta act agc cct gtt gct gct tct gaa gag ttt        7742
Leu Gly Val Glu Leu Thr Ser Pro Val Ala Ala Ser Glu Glu Phe
            2455                2460                2465 gaa gat gaa gaa gaa agt cct gtt aat ttc ccc att tac taaaggtcac      7791
Glu Asp Glu Glu Glu Ser Pro Val Asn Phe Pro Ile Tyr
            2470                2475 ctataaactt tgtttcattt aactatttat taactttata agttaaatat acttggaaat   7851
aagcagttct ccgaactgta gtatttcctt ctcactacct tgtacctta tacttagatt    7911 ggaattctta ataaataaaa ttatatgaaa ttttcaactt attaaaaaaa aaaaaaaaa    7971 a                                                                   7972
```

<210> SEQ ID NO 3
<211> LENGTH: 2479
<212> TYPE: PRT
<213> ORGANISM: Homo sapiens

<400> SEQUENCE: 3

```
Met Pro Pro Asn Ile Asn Trp Lys Glu Ile Met Lys Val Asp Pro Asp
1               5                   10                  15

Asp Leu Pro Arg Gln Glu Glu Leu Ala Asp Asn Leu Leu Ile Ser Leu
            20                  25                  30

Ser Lys Val Glu Val Asn Glu Leu Lys Ser Glu Lys Gln Glu Asn Val
        35                  40                  45

Ile His Leu Phe Arg Ile Thr Gln Ser Leu Met Lys Met Lys Ala Gln
    50                  55                  60

Glu Val Glu Leu Ala Leu Glu Val Glu Lys Ala Gly Glu Glu Gln
65                  70                  75                  80

Ala Lys Phe Glu Asn Gln Leu Lys Thr Lys Val Met Lys Leu Glu Asn
                85                  90                  95

Glu Leu Glu Met Ala Gln Gln Ser Ala Gly Gly Arg Asp Thr Arg Phe
            100                 105                 110

Leu Arg Asn Glu Ile Cys Gln Leu Glu Lys Gln Leu Glu Gln Lys Asp
        115                 120                 125

Arg Glu Leu Glu Asp Met Glu Lys Glu Leu Glu Lys Glu Lys Lys Val
    130                 135                 140

Asn Glu Gln Leu Ala Leu Arg Asn Glu Glu Ala Glu Asn Glu Asn Ser
145                 150                 155                 160

Lys Leu Arg Arg Glu Asn Lys Arg Leu Lys Lys Lys Asn Glu Gln Leu
                165                 170                 175

Cys Gln Asp Ile Ile Asp Tyr Gln Lys Gln Ile Asp Ser Gln Lys Glu
            180                 185                 190

Thr Leu Leu Ser Arg Arg Gly Glu Asp Ser Asp Tyr Arg Ser Gln Leu
        195                 200                 205

Ser Lys Lys Asn Tyr Glu Leu Ile Gln Tyr Leu Asp Glu Ile Gln Thr
    210                 215                 220

Leu Thr Glu Ala Asn Glu Lys Ile Glu Val Gln Asn Gln Glu Met Arg
225                 230                 235                 240

Lys Asn Leu Glu Glu Ser Val Gln Glu Met Glu Lys Met Thr Asp Glu
                245                 250                 255

Tyr Asn Arg Met Lys Ala Ile Val His Gln Thr Asp Asn Val Ile Asp
            260                 265                 270

Gln Leu Lys Lys Glu Asn Asp His Tyr Gln Leu Gln Val Gln Glu Leu
        275                 280                 285
```

```
Thr Asp Leu Leu Lys Ser Lys Asn Glu Glu Asp Pro Ile Met Val
    290                 295                 300

Ala Val Asn Ala Lys Val Glu Glu Trp Lys Leu Ile Leu Ser Ser Lys
305                 310                 315                 320

Asp Asp Glu Ile Ile Glu Tyr Gln Gln Met Leu His Asn Leu Arg Glu
                    325                 330                 335

Lys Leu Lys Asn Ala Gln Leu Asp Ala Asp Lys Ser Asn Val Met Ala
                340                 345                 350

Leu Gln Gln Gly Ile Gln Glu Arg Asp Ser Gln Ile Lys Met Leu Thr
            355                 360                 365

Glu Gln Val Glu Gln Tyr Thr Lys Glu Met Glu Lys Asn Thr Cys Ile
370                 375                 380

Ile Glu Asp Leu Lys Asn Glu Leu Gln Arg Asn Lys Gly Ala Ser Thr
385                 390                 395                 400

Leu Ser Gln Gln Thr His Met Lys Ile Gln Ser Thr Leu Asp Ile Leu
                405                 410                 415

Lys Glu Lys Thr Lys Glu Ala Glu Arg Thr Ala Glu Leu Ala Glu Ala
            420                 425                 430

Asp Ala Arg Glu Lys Asp Lys Glu Leu Val Glu Ala Leu Lys Arg Leu
        435                 440                 445

Lys Asp Tyr Glu Ser Gly Val Tyr Gly Leu Glu Asp Ala Val Val Glu
    450                 455                 460

Ile Lys Asn Cys Lys Asn Gln Ile Lys Ile Arg Asp Arg Glu Ile Glu
465                 470                 475                 480

Ile Leu Thr Lys Glu Ile Asn Lys Leu Glu Leu Lys Ile Ser Asp Phe
                485                 490                 495

Leu Asp Glu Asn Glu Ala Leu Arg Glu Arg Val Gly Leu Glu Pro Lys
                500                 505                 510

Thr Met Ile Asp Leu Thr Glu Phe Arg Asn Ser Lys His Leu Lys Gln
            515                 520                 525

Gln Gln Tyr Arg Ala Glu Asn Gln Ile Leu Leu Lys Glu Ile Glu Ser
        530                 535                 540

Leu Glu Glu Glu Arg Leu Asp Leu Lys Lys Lys Ile Arg Gln Met Ala
545                 550                 555                 560

Gln Glu Arg Gly Lys Arg Ser Ala Thr Ser Gly Leu Thr Thr Glu Asp
                565                 570                 575

Leu Asn Leu Thr Glu Asn Ile Ser Gln Gly Asp Arg Ile Ser Glu Arg
                580                 585                 590

Lys Leu Asp Leu Leu Ser Leu Lys Asn Met Ser Glu Ala Gln Ser Lys
            595                 600                 605

Asn Glu Phe Leu Ser Arg Glu Leu Ile Glu Lys Glu Arg Asp Leu Glu
        610                 615                 620

Arg Ser Arg Thr Val Ile Ala Lys Phe Gln Asn Lys Leu Lys Glu Leu
625                 630                 635                 640

Val Glu Glu Asn Lys Gln Leu Glu Glu Gly Met Lys Glu Ile Leu Gln
                645                 650                 655

Ala Ile Lys Glu Met Gln Lys Asp Pro Asp Val Lys Gly Gly Glu Thr
            660                 665                 670

Ser Leu Ile Ile Pro Ser Leu Glu Arg Leu Val Asn Ala Ile Glu Ser
        675                 680                 685

Lys Asn Ala Glu Gly Ile Phe Asp Ala Ser Leu His Leu Lys Ala Gln
    690                 695                 700

Val Asp Gln Leu Thr Gly Arg Asn Glu Glu Leu Arg Gln Glu Leu Arg
```

```
            705                 710                 715                 720
Glu Ser Arg Lys Glu Ala Ile Asn Tyr Ser Gln Gln Leu Ala Lys Ala
                725                 730                 735

Asn Leu Lys Ile Asp His Leu Glu Lys Glu Thr Ser Leu Leu Arg Gln
                740                 745                 750

Ser Glu Gly Ser Asn Val Val Phe Lys Gly Ile Asp Leu Pro Asp Gly
                755                 760                 765

Ile Ala Pro Ser Ser Ala Ser Ile Ile Asn Ser Gln Asn Glu Tyr Leu
                770                 775                 780

Ile His Leu Leu Gln Glu Leu Glu Asn Lys Glu Lys Lys Leu Lys Asn
785                 790                 795                 800

Leu Glu Asp Ser Leu Glu Asp Tyr Asn Arg Lys Phe Ala Val Ile Arg
                805                 810                 815

His Gln Gln Ser Leu Leu Tyr Lys Glu Tyr Leu Ser Glu Lys Glu Thr
                820                 825                 830

Trp Lys Thr Glu Ser Lys Thr Ile Lys Glu Glu Lys Arg Lys Leu Glu
                835                 840                 845

Asp Gln Val Gln Gln Asp Ala Ile Lys Val Lys Glu Tyr Asn Asn Leu
850                 855                 860

Leu Asn Ala Leu Gln Met Asp Ser Asp Glu Met Lys Lys Ile Leu Ala
865                 870                 875                 880

Glu Asn Ser Arg Lys Ile Thr Val Leu Gln Val Asn Glu Lys Ser Leu
                885                 890                 895

Ile Arg Gln Tyr Thr Thr Leu Val Glu Leu Glu Arg Gln Leu Arg Lys
                900                 905                 910

Glu Asn Glu Lys Gln Lys Asn Glu Leu Leu Ser Met Glu Ala Glu Val
                915                 920                 925

Cys Glu Lys Ile Gly Cys Leu Gln Arg Phe Lys Glu Met Ala Ile Phe
                930                 935                 940

Lys Ile Ala Ala Leu Gln Lys Val Val Asp Asn Ser Val Ser Leu Ser
945                 950                 955                 960

Glu Leu Glu Leu Ala Asn Lys Gln Tyr Asn Glu Leu Thr Ala Lys Tyr
                965                 970                 975

Arg Asp Ile Leu Gln Lys Asp Asn Met Leu Val Gln Arg Thr Ser Asn
                980                 985                 990

Leu Glu His Leu Glu Cys Glu Asn  Ile Ser Leu Lys Glu  Gln Val Glu
                995                 1000                1005

Ser Ile Asn Lys Glu Leu Glu  Ile Thr Lys Glu Lys  Leu His Thr
    1010                1015                1020

Ile Glu Gln Ala Trp Glu Gln  Glu Thr Lys Leu Gly  Asn Glu Ser
    1025                1030                1035

Ser Met Asp Lys Ala Lys Lys  Ser Ile Thr Asn Ser  Asp Ile Val
    1040                1045                1050

Ser Ile Ser Lys Lys Ile Thr  Met Leu Glu Met Lys  Glu Leu Asn
    1055                1060                1065

Glu Arg Gln Arg Ala Glu His  Cys Gln Lys Met Tyr  Glu His Leu
    1070                1075                1080

Arg Thr Ser Leu Lys Gln Met  Glu Glu Arg Asn Phe  Glu Leu Glu
    1085                1090                1095

Thr Lys Phe Ala Glu Leu Thr  Lys Ile Asn Leu Asp  Ala Gln Lys
    1100                1105                1110

Val Glu Gln Met Leu Arg Asp  Glu Leu Ala Asp Ser  Val Ser Lys
    1115                1120                1125
```

-continued

```
Ala Val Ser Asp Ala Asp Arg Gln Arg Ile Leu Glu Leu Glu Lys
    1130                1135                1140

Asn Glu Met Glu Leu Lys Val Glu Val Ser Lys Leu Arg Glu Ile
    1145                1150                1155

Ser Asp Ile Ala Arg Arg Gln Val Glu Ile Leu Asn Ala Gln Gln
    1160                1165                1170

Gln Ser Arg Asp Lys Glu Val Glu Ser Leu Arg Met Gln Leu Leu
    1175                1180                1185

Asp Tyr Gln Ala Gln Ser Asp Glu Lys Ser Leu Ile Ala Lys Leu
    1190                1195                1200

His Gln His Asn Val Ser Leu Gln Leu Ser Glu Ala Thr Ala Leu
    1205                1210                1215

Gly Lys Leu Glu Ser Ile Thr Ser Lys Leu Gln Lys Met Glu Ala
    1220                1225                1230

Tyr Asn Leu Arg Leu Glu Gln Lys Leu Asp Glu Lys Glu Gln Ala
    1235                1240                1245

Leu Tyr Tyr Ala Arg Leu Glu Gly Arg Asn Arg Ala Lys His Leu
    1250                1255                1260

Arg Gln Thr Ile Gln Ser Leu Arg Arg Gln Phe Ser Gly Ala Leu
    1265                1270                1275

Pro Leu Ala Gln Gln Glu Lys Phe Ser Lys Thr Met Ile Gln Leu
    1280                1285                1290

Gln Asn Asp Lys Leu Lys Ile Met Gln Glu Met Lys Asn Ser Gln
    1295                1300                1305

Gln Glu His Arg Asn Met Glu Asn Lys Thr Leu Glu Met Glu Leu
    1310                1315                1320

Lys Leu Lys Gly Leu Glu Glu Leu Ile Ser Thr Leu Lys Asp Thr
    1325                1330                1335

Lys Gly Ala Gln Lys Val Ile Asn Trp His Met Lys Ile Glu Glu
    1340                1345                1350

Leu Arg Leu Gln Glu Leu Lys Leu Asn Arg Glu Leu Val Lys Asp
    1355                1360                1365

Lys Glu Glu Ile Lys Tyr Leu Asn Asn Ile Ile Ser Glu Tyr Glu
    1370                1375                1380

Arg Thr Ile Ser Ser Leu Glu Glu Glu Ile Val Gln Gln Asn Lys
    1385                1390                1395

Phe His Glu Glu Arg Gln Met Ala Trp Asp Gln Arg Glu Val Asp
    1400                1405                1410

Leu Glu Arg Gln Leu Asp Ile Phe Asp Arg Gln Gln Asn Glu Ile
    1415                1420                1425

Leu Asn Ala Ala Gln Lys Phe Glu Glu Ala Thr Gly Ser Ile Pro
    1430                1435                1440

Asp Pro Ser Leu Pro Leu Pro Asn Gln Leu Glu Ile Ala Leu Arg
    1445                1450                1455

Lys Ile Lys Glu Asn Ile Arg Ile Ile Leu Glu Thr Arg Ala Thr
    1460                1465                1470

Cys Lys Ser Leu Glu Glu Lys Leu Lys Glu Lys Glu Ser Ala Leu
    1475                1480                1485

Arg Leu Ala Glu Gln Asn Ile Leu Ser Arg Asp Lys Val Ile Asn
    1490                1495                1500

Glu Leu Arg Leu Arg Leu Pro Ala Thr Ala Glu Arg Glu Lys Leu
    1505                1510                1515
```

```
Ile Ala Glu Leu Gly Arg Lys Glu Met Glu Pro Lys Ser His His
    1520                1525                1530

Thr Leu Lys Ile Ala His Gln Thr Ile Ala Asn Met Gln Ala Arg
    1535                1540                1545

Leu Asn Gln Lys Glu Glu Val Leu Lys Lys Tyr Gln Arg Leu Leu
    1550                1555                1560

Glu Lys Ala Arg Glu Gln Arg Glu Ile Val Lys Lys His Glu
    1565                1570                1575

Glu Asp Leu His Ile Leu His Arg Leu Glu Leu Gln Ala Asp
    1580                1585                1590

Ser Ser Leu Asn Lys Phe Lys Gln Thr Ala Trp Asp Leu Met Lys
    1595                1600                1605

Gln Ser Pro Thr Pro Val Pro Thr Asn Lys His Phe Ile Arg Leu
    1610                1615                1620

Ala Glu Met Glu Gln Thr Val Ala Glu Gln Asp Asp Ser Leu Ser
    1625                1630                1635

Ser Leu Leu Val Lys Leu Lys Lys Val Ser Gln Asp Leu Glu Arg
    1640                1645                1650

Gln Arg Glu Ile Thr Glu Leu Lys Val Lys Glu Phe Glu Asn Ile
    1655                1660                1665

Lys Leu Gln Leu Gln Glu Asn His Glu Asp Glu Val Lys Lys Val
    1670                1675                1680

Lys Ala Glu Val Glu Asp Leu Lys Tyr Leu Leu Asp Gln Ser Gln
    1685                1690                1695

Lys Glu Ser Gln Cys Leu Lys Ser Glu Leu Gln Ala Gln Lys Glu
    1700                1705                1710

Ala Asn Ser Arg Ala Pro Thr Thr Thr Met Arg Asn Leu Val Glu
    1715                1720                1725

Arg Leu Lys Ser Gln Leu Ala Leu Lys Glu Lys Gln Gln Lys Ala
    1730                1735                1740

Leu Ser Arg Ala Leu Leu Glu Leu Arg Ala Glu Met Thr Ala Ala
    1745                1750                1755

Ala Glu Glu Arg Ile Ile Ser Ala Thr Ser Gln Lys Glu Ala His
    1760                1765                1770

Leu Asn Val Gln Gln Ile Val Asp Arg His Thr Arg Glu Leu Lys
    1775                1780                1785

Thr Gln Val Glu Asp Leu Asn Glu Asn Leu Leu Lys Leu Lys Glu
    1790                1795                1800

Ala Leu Lys Thr Ser Lys Asn Arg Glu Asn Ser Leu Thr Asp Asn
    1805                1810                1815

Leu Asn Asp Leu Asn Asn Glu Leu Gln Lys Lys Gln Lys Ala Tyr
    1820                1825                1830

Asn Lys Ile Leu Arg Glu Lys Glu Glu Ile Asp Gln Glu Asn Asp
    1835                1840                1845

Glu Leu Lys Arg Gln Ile Lys Arg Leu Thr Ser Gly Leu Gln Gly
    1850                1855                1860

Lys Pro Leu Thr Asp Asn Lys Gln Ser Leu Ile Glu Glu Leu Gln
    1865                1870                1875

Arg Lys Val Lys Lys Leu Glu Asn Gln Leu Glu Gly Lys Val Glu
    1880                1885                1890

Glu Val Asp Leu Lys Pro Met Lys Glu Lys Asn Ala Lys Glu Glu
    1895                1900                1905

Leu Ile Arg Trp Glu Glu Gly Lys Lys Trp Gln Ala Lys Ile Glu
```

-continued

```
            1910                1915                1920
Gly Ile Arg Asn Lys Leu Lys Glu Lys Glu Gly Glu Val Phe Thr
            1925                1930                1935
Leu Thr Lys Gln Leu Asn Thr Leu Lys Asp Leu Phe Ala Lys Ala
            1940                1945                1950
Asp Lys Glu Lys Leu Thr Leu Gln Arg Lys Leu Lys Thr Thr Gly
            1955                1960                1965
Met Thr Val Asp Gln Val Leu Gly Ile Arg Ala Leu Glu Ser Glu
            1970                1975                1980
Lys Glu Leu Glu Glu Leu Lys Lys Arg Asn Leu Asp Leu Glu Asn
            1985                1990                1995
Asp Ile Leu Tyr Met Arg Ala His Gln Ala Leu Pro Arg Asp Ser
            2000                2005                2010
Val Val Glu Asp Leu His Leu Gln Asn Arg Tyr Leu Gln Glu Lys
            2015                2020                2025
Leu His Ala Leu Glu Lys Gln Phe Ser Lys Asp Thr Tyr Ser Lys
            2030                2035                2040
Pro Ser Ile Ser Gly Ile Glu Ser Asp Asp His Cys Gln Arg Glu
            2045                2050                2055
Gln Glu Leu Gln Lys Glu Asn Leu Lys Leu Ser Ser Glu Asn Ile
            2060                2065                2070
Glu Leu Lys Phe Gln Leu Glu Gln Ala Asn Lys Asp Leu Pro Arg
            2075                2080                2085
Leu Lys Asn Gln Val Arg Asp Leu Lys Glu Met Cys Glu Phe Leu
            2090                2095                2100
Lys Lys Glu Lys Ala Glu Val Gln Arg Lys Leu Gly His Val Arg
            2105                2110                2115
Gly Ser Gly Arg Ser Gly Lys Thr Ile Pro Glu Leu Glu Lys Thr
            2120                2125                2130
Ile Gly Leu Met Lys Lys Val Val Glu Lys Val Gln Arg Glu Asn
            2135                2140                2145
Glu Gln Leu Lys Lys Ala Ser Gly Ile Leu Thr Ser Glu Lys Met
            2150                2155                2160
Ala Asn Ile Glu Gln Glu Asn Glu Lys Leu Lys Ala Glu Leu Glu
            2165                2170                2175
Lys Leu Lys Ala His Leu Gly His Gln Leu Ser Met His Tyr Glu
            2180                2185                2190
Ser Lys Thr Lys Gly Thr Glu Lys Ile Ile Ala Glu Asn Glu Arg
            2195                2200                2205
Leu Arg Lys Glu Leu Lys Lys Glu Thr Asp Ala Ala Glu Lys Leu
            2210                2215                2220
Arg Ile Ala Lys Asn Asn Leu Glu Ile Leu Asn Glu Lys Met Thr
            2225                2230                2235
Val Gln Leu Glu Glu Thr Gly Lys Arg Leu Gln Phe Ala Glu Ser
            2240                2245                2250
Arg Gly Pro Gln Leu Glu Gly Ala Asp Ser Lys Ser Trp Lys Ser
            2255                2260                2265
Ile Val Val Thr Arg Met Tyr Glu Thr Lys Leu Lys Glu Leu Glu
            2270                2275                2280
Thr Asp Ile Ala Lys Lys Asn Gln Ser Ile Thr Asp Leu Lys Gln
            2285                2290                2295
Leu Val Lys Glu Ala Thr Glu Arg Glu Gln Lys Val Asn Lys Tyr
            2300                2305                2310
```

```
Asn Glu Asp Leu Glu Gln Gln Ile Lys Ile Leu Lys His Val Pro
    2315                2320                2325

Glu Gly Ala Glu Thr Glu Gln Gly Leu Lys Arg Glu Leu Gln Val
    2330                2335                2340

Leu Arg Leu Ala Asn His Gln Leu Asp Lys Glu Lys Ala Glu Leu
    2345                2350                2355

Ile His Gln Ile Glu Ala Asn Lys Asp Gln Ser Gly Ala Glu Ser
    2360                2365                2370

Thr Ile Pro Asp Ala Asp Gln Leu Lys Glu Lys Ile Lys Asp Leu
    2375                2380                2385

Glu Thr Gln Leu Lys Met Ser Asp Leu Glu Lys Gln His Leu Lys
    2390                2395                2400

Glu Glu Ile Lys Lys Leu Lys Lys Glu Leu Glu Asn Phe Asp Pro
    2405                2410                2415

Ser Phe Phe Glu Glu Ile Glu Asp Leu Lys Tyr Asn Tyr Lys Glu
    2420                2425                2430

Glu Val Lys Lys Asn Ile Leu Leu Glu Lys Val Lys Lys Leu
    2435                2440                2445

Ser Glu Gln Leu Gly Val Glu Leu Thr Ser Pro Val Ala Ala Ser
    2450                2455                2460

Glu Glu Phe Glu Asp Glu Glu Ser Pro Val Asn Phe Pro Ile
    2465                2470                2475

Tyr
```

```
<210> SEQ ID NO 4
<211> LENGTH: 128
<212> TYPE: DNA
<213> ORGANISM: Homo sapiens
<220> FEATURE:
<221> NAME/KEY: misc_feature
<222> LOCATION: (1)..(128)
<223> OTHER INFORMATION: 128 nucleotide aberrant CEO290 exon

<400> SEQUENCE: 4
tagagatggg gtttcacctt gttagccagg atggtgtcga tctcctgaac tcgtgatcca      60
cccgcctcgg cctcctaaag tgctgggatt acagatgtga gccaccgcac ctggccccag     120
ttgtaatt                                                              128

<210> SEQ ID NO 5
<211> LENGTH: 997
<212> TYPE: PRT
<213> ORGANISM: Homo sapiens
<220> FEATURE:
<221> NAME/KEY: misc_feature
<222> LOCATION: (1)..(997)
<223> OTHER INFORMATION: Aberrant CEP290 polypeptide

<400> SEQUENCE: 5

Met Pro Pro Asn Ile Asn Trp Lys Glu Ile Met Lys Val Asp Pro Asp
1               5                   10                  15

Asp Leu Pro Arg Gln Glu Glu Leu Ala Asp Asn Leu Leu Ile Ser Leu
            20                  25                  30

Ser Lys Val Glu Val Asn Glu Leu Lys Ser Glu Lys Gln Glu Asn Val
        35                  40                  45

Ile His Leu Phe Arg Ile Thr Gln Ser Leu Met Lys Met Lys Ala Gln
    50                  55                  60

Glu Val Glu Leu Ala Leu Glu Glu Val Glu Lys Ala Gly Glu Glu Gln
```

-continued

```
                65                  70                  75                  80
Ala Lys Phe Glu Asn Gln Leu Lys Thr Lys Val Met Lys Leu Glu Asn
                    85                  90                  95
Glu Leu Glu Met Ala Gln Gln Ser Ala Gly Gly Arg Asp Thr Arg Phe
                    100                 105                 110
Leu Arg Asn Glu Ile Cys Gln Leu Glu Lys Gln Leu Glu Gln Lys Asp
                    115                 120                 125
Arg Glu Leu Glu Asp Met Glu Lys Glu Leu Glu Lys Glu Lys Lys Val
                    130                 135                 140
Asn Glu Gln Leu Ala Leu Arg Asn Glu Glu Ala Glu Asn Glu Asn Ser
145                 150                 155                 160
Lys Leu Arg Arg Glu Asn Lys Arg Leu Lys Lys Asn Glu Gln Leu
                    165                 170                 175
Cys Gln Asp Ile Ile Asp Tyr Gln Lys Gln Ile Asp Ser Gln Lys Glu
                    180                 185                 190
Thr Leu Leu Ser Arg Arg Gly Glu Asp Ser Asp Tyr Arg Ser Gln Leu
                    195                 200                 205
Ser Lys Lys Asn Tyr Glu Leu Ile Gln Tyr Leu Asp Glu Ile Gln Thr
210                 215                 220
Leu Thr Glu Ala Asn Glu Lys Ile Glu Val Gln Asn Gln Glu Met Arg
225                 230                 235                 240
Lys Asn Leu Glu Glu Ser Val Gln Glu Met Lys Met Thr Asp Glu
                    245                 250                 255
Tyr Asn Arg Met Lys Ala Ile Val His Gln Thr Asp Asn Val Ile Asp
                    260                 265                 270
Gln Leu Lys Lys Glu Asn Asp His Tyr Gln Leu Gln Val Gln Glu Leu
                    275                 280                 285
Thr Asp Leu Leu Lys Ser Lys Asn Glu Glu Asp Asp Pro Ile Met Val
                    290                 295                 300
Ala Val Asn Ala Lys Val Glu Glu Trp Lys Leu Ile Leu Ser Ser Lys
305                 310                 315                 320
Asp Asp Glu Ile Ile Glu Tyr Gln Gln Met Leu His Asn Leu Arg Glu
                    325                 330                 335
Lys Leu Lys Asn Ala Gln Leu Asp Ala Asp Lys Ser Asn Val Met Ala
                    340                 345                 350
Leu Gln Gln Gly Ile Gln Glu Arg Asp Ser Gln Ile Lys Met Leu Thr
                    355                 360                 365
Glu Gln Val Glu Gln Tyr Thr Lys Glu Met Glu Lys Asn Thr Cys Ile
                    370                 375                 380
Ile Glu Asp Leu Lys Asn Glu Leu Gln Arg Asn Lys Gly Ala Ser Thr
385                 390                 395                 400
Leu Ser Gln Gln Thr His Met Lys Ile Gln Ser Thr Leu Asp Ile Leu
                    405                 410                 415
Lys Glu Lys Thr Lys Glu Ala Glu Arg Thr Ala Glu Leu Ala Glu Ala
                    420                 425                 430
Asp Ala Arg Glu Lys Asp Lys Glu Leu Val Glu Ala Leu Lys Arg Leu
                    435                 440                 445
Lys Asp Tyr Glu Ser Gly Val Tyr Gly Leu Glu Asp Ala Val Val Glu
                    450                 455                 460
Ile Lys Asn Cys Lys Asn Gln Ile Lys Ile Arg Asp Arg Glu Ile Glu
465                 470                 475                 480
Ile Leu Thr Lys Glu Ile Asn Lys Leu Glu Leu Lys Ile Ser Asp Phe
                    485                 490                 495
```

```
Leu Asp Glu Asn Glu Ala Leu Arg Glu Arg Val Gly Leu Glu Pro Lys
            500                 505                 510

Thr Met Ile Asp Leu Thr Glu Phe Arg Asn Ser Lys His Leu Lys Gln
            515                 520                 525

Gln Gln Tyr Arg Ala Glu Asn Gln Ile Leu Leu Lys Glu Ile Glu Ser
            530                 535                 540

Leu Glu Glu Glu Arg Leu Asp Leu Lys Lys Lys Ile Arg Gln Met Ala
545                 550                 555                 560

Gln Glu Arg Gly Lys Arg Ser Ala Thr Ser Gly Leu Thr Thr Glu Asp
                565                 570                 575

Leu Asn Leu Thr Glu Asn Ile Ser Gln Gly Asp Arg Ile Ser Glu Arg
            580                 585                 590

Lys Leu Asp Leu Leu Ser Leu Lys Asn Met Ser Glu Ala Gln Ser Lys
            595                 600                 605

Asn Glu Phe Leu Ser Arg Glu Leu Ile Glu Lys Glu Arg Asp Leu Glu
            610                 615                 620

Arg Ser Arg Thr Val Ile Ala Lys Phe Gln Asn Lys Leu Lys Glu Leu
625                 630                 635                 640

Val Glu Glu Asn Lys Gln Leu Glu Glu Gly Met Lys Glu Ile Leu Gln
                645                 650                 655

Ala Ile Lys Glu Met Gln Lys Asp Pro Asp Val Lys Gly Gly Glu Thr
            660                 665                 670

Ser Leu Ile Ile Pro Ser Leu Glu Arg Leu Val Asn Ala Ile Glu Ser
            675                 680                 685

Lys Asn Ala Glu Gly Ile Phe Asp Ala Ser Leu His Leu Lys Ala Gln
            690                 695                 700

Val Asp Gln Leu Thr Gly Arg Asn Glu Glu Leu Arg Gln Glu Leu Arg
705                 710                 715                 720

Glu Ser Arg Lys Glu Ala Ile Asn Tyr Ser Gln Gln Leu Ala Lys Ala
                725                 730                 735

Asn Leu Lys Ile Asp His Leu Glu Lys Glu Thr Ser Leu Leu Arg Gln
            740                 745                 750

Ser Glu Gly Ser Asn Val Val Phe Lys Gly Ile Asp Leu Pro Asp Gly
            755                 760                 765

Ile Ala Pro Ser Ser Ala Ser Ile Ile Asn Ser Gln Asn Glu Tyr Leu
            770                 775                 780

Ile His Leu Leu Gln Glu Leu Glu Asn Lys Glu Lys Lys Leu Lys Asn
785                 790                 795                 800

Leu Glu Asp Ser Leu Glu Asp Tyr Asn Arg Lys Phe Ala Val Ile Arg
            805                 810                 815

His Gln Gln Ser Leu Leu Tyr Lys Glu Tyr Leu Ser Glu Lys Glu Thr
            820                 825                 830

Trp Lys Thr Glu Ser Lys Thr Ile Lys Glu Glu Lys Arg Lys Leu Glu
            835                 840                 845

Asp Gln Val Gln Gln Asp Ala Ile Lys Val Lys Glu Tyr Asn Asn Leu
            850                 855                 860

Leu Asn Ala Leu Gln Met Asp Ser Asp Glu Met Lys Lys Ile Leu Ala
865                 870                 875                 880

Glu Asn Ser Arg Lys Ile Thr Val Leu Gln Val Asn Glu Lys Ser Leu
                885                 890                 895

Ile Arg Gln Tyr Thr Thr Leu Val Glu Leu Glu Arg Gln Leu Arg Lys
            900                 905                 910
```

```
Glu Asn Glu Lys Gln Lys Asn Glu Leu Leu Ser Met Glu Ala Glu Val
            915                 920                 925

Cys Glu Lys Ile Gly Cys Leu Gln Arg Phe Lys Glu Met Ala Ile Phe
        930                 935                 940

Lys Ile Ala Ala Leu Gln Lys Val Val Asp Asn Ser Val Ser Leu Ser
945                 950                 955                 960

Glu Leu Glu Leu Ala Asn Lys Gln Tyr Asn Glu Leu Thr Ala Lys Tyr
                965                 970                 975

Arg Asp Ile Leu Gln Lys Asp Asn Met Leu Val Gln Arg Thr Ser Asn
            980                 985                 990

Leu Glu His Leu Glu
        995

<210> SEQ ID NO 6
<211> LENGTH: 143
<212> TYPE: DNA
<213> ORGANISM: Homo sapiens
<220> FEATURE:
<221> NAME/KEY: misc_feature
<222> LOCATION: (1)..(143)
<223> OTHER INFORMATION: 143 nucleotide motif

<400> SEQUENCE: 6
tagagatggg gtttcacctt gttagccagg atggtgtcga tctcctgaac tcgtgatcca      60
cccgcctcgg cctcctaaag tgctgggatt acagatgtga gccaccgcac ctggccccag     120
ttgtaattgt gaatatctca tac                                             143

<210> SEQ ID NO 7
<211> LENGTH: 42
<212> TYPE: DNA
<213> ORGANISM: Homo sapiens
<220> FEATURE:
<221> NAME/KEY: misc_feature
<222> LOCATION: (1)..(42)
<223> OTHER INFORMATION: 42 nucleotide motif

<400> SEQUENCE: 7
acagatgtga gccaccgcac ctggccccag ttgtaattgt ga                         42

<210> SEQ ID NO 8
<211> LENGTH: 24
<212> TYPE: DNA
<213> ORGANISM: Homo sapiens
<220> FEATURE:
<221> NAME/KEY: misc_feature
<222> LOCATION: (1)..(24)
<223> OTHER INFORMATION: 24 nucleotide motif

<400> SEQUENCE: 8
ccaccgcacc tggccccagt tgta                                             24

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AON-1

<400> SEQUENCE: 9
taatcccagc actttaggag                                                  20
```

```
<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AON-2

<400> SEQUENCE: 10
gggccaggtg cggtgg                                                  16

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AON-3

<400> SEQUENCE: 11
aactggggcc aggtgcg                                                 17

<210> SEQ ID NO 12
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AON-4

<400> SEQUENCE: 12
tacaactggg gccaggtg                                                18

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: AON-5

<400> SEQUENCE: 13
actcacaatt acaactgggg                                              20

<210> SEQ ID NO 14
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: SON-3

<400> SEQUENCE: 14
cgcacctggc cccagtt                                                 17

<210> SEQ ID NO 15
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      PCR primer

<400> SEQUENCE: 15
tgctaagtac agggacatct tgc                                           23

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 16
agactccact tgttctttta aggag                                         25

<210> SEQ ID NO 17
<211> LENGTH: 36
<212> TYPE: DNA
<213> ORGANISM: Homo sapiens

<400> SEQUENCE: 17
cacctggccc cagttgtaat tgtgaatatc tcatac                             36

<210> SEQ ID NO 18
<211> LENGTH: 36
<212> TYPE: RNA
<213> ORGANISM: Homo sapiens

<400> SEQUENCE: 18
caccuggccc caguuguaau ugugaauauc ucauac                             36

<210> SEQ ID NO 19
<211> LENGTH: 36
<212> TYPE: DNA
<213> ORGANISM: Homo sapiens

<400> SEQUENCE: 19
cacctggccc cagttgtaat tgtgagtatc tcatac                             36

<210> SEQ ID NO 20
<211> LENGTH: 36
<212> TYPE: RNA
<213> ORGANISM: Homo sapiens

<400> SEQUENCE: 20
caccuggccc caguuguaau ugugaguauc ucauac                             36

<210> SEQ ID NO 21
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 21
auacuacuaa uuacaacugg g                                             21
```

ANTISENSE OLIGONUCLEOTIDES FOR THE TREATMENT OF LEBER CONGENITAL AMAUROSIS

CROSS-REFERENCE TO RELATED APPLICATIONS

The present application is a Continuation Application of U.S. application Ser. No. 16/842,157, filed on Apr. 7, 2020, which is a Continuation Application of U.S. application Ser. No. 16/197,865, filed Nov. 21, 2018, which is a Continuation Application of U.S. application Ser. No. 15/963,229, filed Apr. 26, 2018, which is a Continuation Application of U.S. application Ser. No. 15/656,635, filed Jul. 21, 2017, which is a Continuation Application of U.S. application Ser. No. 14/342,776, filed Jun. 16, 2014, which is the U.S. National Phase of International Patent Application No. PCT/NL2012/050275, filed Apr. 25, 2012 and published as WO 2013/036105 A1, which claims priority to Netherlands Patent Application No. 2007351, filed Sep. 5, 2011, and U.S. Provisional Application No. 61/531,137, filed Sep. 6, 2011. The contents of these applications are herein incorporated by reference in their entirety.

SEQUENCE LISTING

The instant application contains a Sequence Listing which has now been submitted electronically in ASCII format and is hereby incorporated by reference in its entirety. Said ASCII copy, created on Feb. 17, 2022, is named Sequence_Listing.txt and is 230 KB.

FIELD OF THE INVENTION

The present invention relates to the fields of medicine and immunology. In particular, it relates to novel antisense oligonucleotides that may be used in the treatment, prevention and/or delay of Leber congenital amaurosis.

BACKGROUND OF THE INVENTION

Leber congenital amaurosis (LCA) is the most severe form of inherited retinal dystrophy, with an onset of disease symptoms in the first years of life (Leber, T., 1869) and an estimated prevalence of approximately 1 in 50,000 worldwide (Koenekoop et al, 2007; Stone, 2007). Genetically, LCA is a heterogeneous disease, with fifteen genes identified to date in which mutations are causative for LCA (den Hollander et al, 2008; Estrada-Cuzcano et al, 2011). The most frequently mutated LCA gene is (CEP290, accounting for ~15% of all cases (Stone, 2007; den Hollander, 2008; den Hollander, 2006; Perrault et al, 2007). Severe mutations in CEP290 have been reported to cause a spectrum of systemic diseases that, besides retinal dystrophy, are characterized by brain defects, kidney malformations, polydactyly and/or obesity (Baal et al, 2007; den Hollander et al, 2008; Helou et al, 2007; Valente et al, 2006). There is no clear-cut genotype-phenotype correlation between the combination of CEP290 mutations and the associated phenotypes, but patients with LCA and early-onset retinal dystrophy very often carry hypomorphic alleles (Stone, 2007; den Hollander et al, 2006; Perrault et al, 2007; Coppieters et al, 2010; Liitink et al 2010). The by far most frequently occurring hypomorphic CEP290 mutation, especially in European countries and in the US, is a change in intron 26 of CEP290 (c.2991+1655A>G) (Stone, 2007; den Hollander et al, 2006; Perrault et al, 2007; Liitink et al, 2010). This mutation creates a cryptic splice donor site in intron 26 which results in the inclusion of an aberrant exon of 128 bp in the mutant CEP290 mRNA, and inserts a premature stop codon (p.C998X) (see FIG. 1). Besides the mutant CEP290 mRNA, also the wild-type transcript that lacks the aberrant exon is still produced, explaining the hypomorphic nature of this mutation (Estrada-Cuzcano et al, 2011).

LCA, and other retinal dystrophies, for long have been considered incurable diseases. However, the first phase I/II clinical trials using gene augmentation therapy have lead to promising results in a selected group of adult LCA/RP patients with mutations in the RPE65 gene (Bainbridge et al, 2008; Cideciyan et al, 2008; Hauswirth et al, 2008; Maguire et al, 2008). Unilateral subretinal injections of adeno-associated viruses particles carrying constructs encoding the wild-type RPE65 cDNA were shown to be safe and moderately effective in some patients, without causing any adverse effects. In a follow-up study using adults and children, visual improvements were more sustained, especially in the children who all gained ambulatory vision (Maguire et al, 2009). Together, these studies have shown the potential to treat LCA, and thereby enormously boosted the development of therapeutic strategies for other genetic subtypes of retinal dystrophies (den Hollander et al, 2010). However, due to the tremendous variety in gene size, and technical limitations of the vehicles that are used to deliver therapeutic constructs, gene augmentation therapy may not be applicable to all genes. The RPE65 cDNA is for instance only 1.6 kb, whereas the CEP290 cDNA amounts to about 7.4 kb, thereby exceeding the cargo size of many available vectors, including the presently used adeno-associated vectors (AAV). In addition, using gene replacement therapy, it is hard to control the expression levels of the therapeutic gene which for some genes need to be tightly regulated. It is therefore an objective of the present invention to provide a convenient therapeutic strategy for the prevention, treatment or delay of Leber congenital amaurosis as caused by an intronic mutation in CEP290.

DETAILED DESCRIPTION OF THE INVENTION

Surprisingly, it has now been demonstrated that specific antisense oligonucleotides (AONs) are able to block the aberrant splicing of CEP290 that is caused by the intronic LCA mutation.

Accordingly, in a first aspect the present invention provides an exon skipping molecule that binds to and/or is complementary to a polynucleotide with the nucleotide sequence as shown in SEQ ID NO. 6, preferably SEQ ID NO: 7, more preferably SEQ ID NO: 8, or a part thereof.

In all embodiments of the present invention, the terms "modulating splicing" and "exon skipping" are synonymous. In respect of (CEP290, "modulating splicing" or "exon skipping" are to be construed as the exclusion of the aberrant 128 nucleotide exon (SEQ ID NO: 4) from the CEP1290 mRNA (see FIG. 1). The term exon skipping is herein defined as the induction within a cell of a mature mRNA that does not contain a particular exon that would be present in the mature mRNA without exon skipping. Exon skipping is achieved by providing a cell expressing the pre-mRNA of said mature mRNA with a molecule capable of interfering with sequences such as, for example, the (cryptic) splice donor or (cryptic) splice acceptor sequence required for allowing the enzymatic process of splicing, or with a molecule that is capable of interfering with an exon inclusion signal required for recognition of a stretch of nucleotides as an exon to be included in the mature mRNA; such molecules are herein referred to as exon skipping molecules The term pre-mRNA refers to a non-processed or partly processed precursor mRNA that is synthesized from a DNA template in the nucleus of a cell by transcription.

The term "antisense oligonucleotide" is understood to refer to a nucleotide sequence which is substantially complementary to a target nucleotide sequence in a pre-mRNA molecule, hrRNA (heterogenous nuclear RNA) or mRNA molecule. The degree of complementarity (or substantial complementarity) of the antisense sequence is preferably such that a molecule comprising the antisense sequence can form a stable hybrid with the target nucleotide sequence in the RNA molecule under physiological conditions.

The terms "antisense oligonucleotide" and "oligonucleotide" are used interchangeably herein and are understood to refer to an oligonucleotide comprising an antisense sequence.

In an embodiment, an exon skipping molecule as defined herein can be a compound molecule that binds and/or is complementary to the specified sequence, or a protein such as an RNA-binding protein or a non-natural zinc-finger protein that has been modified to be able to bind to the indicated nucleotide sequence on a RNA molecule. Methods for screening compound molecules that bind specific nucleotide sequences are, for example, disclosed in PCT/NL01/00697 and U.S. Pat. No. 6,875,736, which are herein incorporated by reference. Methods for designing RNA-binding Zinc-finger proteins that bind specific nucleotide sequences are disclosed by Friesen and Darby, Nature Structural Biology 5: 543-546 (1998) which is herein incorporated by reference. Binding to one of the specified SEQ ID NO: 6, 7 or 8 sequence, preferably in the context of the aberrant 128 nucleotide CEP290 exon (SEQ ID NO: 4) may be assessed via techniques known to the skilled person. A preferred technique is gel mobility shift assay as described in EP 1 619 249. In a preferred embodiment, an exon skipping molecule is said to bind to one of the specified sequences as soon as a binding of said molecule to a labeled sequence SEQ ID NO: 6, 7 or 8 is detectable in a gel mobility shift assay.

In all embodiments of the invention, an exon skipping molecule is preferably a nucleic acid molecule, preferably an oligonucleotide. Preferably, an exon skipping molecule according to the invention is a nucleic acid molecule, preferably an oligonucleotide, which is complementary or substantially complementary to a nucleotide sequence as shown in SEQ ID NO: 6, preferably SEQ ID NO. 7, more preferably SEQ ID NO: 8, or a part thereof as later defined herein.

The term "substantially complementary" used in the context of the present invention indicates that some mismatches in the antisense sequence are allowed as long as the functionality, i.e. inducing skipping of the aberrant 128 nucleotide CEP290 exon (SEQ ID NO: 4), is still acceptable. Preferably, the complementarity is from 90% to 100%. In general this allows for 1 or 2 mismatch(es) in an oligonucleotide of 20 nucleotides or 1, 2, 3 or 4 mismatches in an oligonucleotide of 40 nucleotides, or 1, 2, 3, 4, 5 or 6 mismatches in an oligonucleotide of 60 nucleotides, etc.

The present invention provides a method for designing an exon skipping molecule, preferably an oligonucleotide able to induce skipping of the aberrant 128 nucleotide CEP290 exon (SEQ ID NO: 4). First, said oligonucleotide is selected to bind to one of SEQ ID NO: 6, 7 or 8 or a part thereof as defined later herein. Subsequently, in a preferred method at least one of the following aspects has to be taken into account for designing, improving said exon skipping molecule any further:

The exon skipping molecule preferably does not contain a CpG or a stretch of CpG, The exon skipping molecule has acceptable RNA binding kinetics and/or thermodynamic properties.

The presence of a CpG or a stretch of CpG in an oligonucleotide is usually associated with an increased immunogenicity of said oligonucleotide (Dorn and Kippenberger, 2008). This increased immunogenicity is undesired since it may induce damage of the tissue to be treated, i.e. the eye. Immunogenicity may be assessed in an animal model by assessing the presence of CD4+ and/or CD8+ cells and/or inflammatory mononucleocyte infiltration. Immunogenicity may also be assessed in blood of an animal or of a human being treated with an oligonucleotide of the invention by detecting the presence of a neutralizing antibody and/or an antibody recognizing said oligonucleotide using a standard immunoassay known to the skilled person.

An increase in immunogenicity may be assessed by detecting the presence or an increasing amount of a neutralizing antibody or an antibody recognizing said oligonucleotide using a standard immunoassay.

The invention allows designing an oligonucleotide with acceptable RNA binding kinetics and/or thermodynamic properties. The RNA binding kinetics and/or thermodynamic properties are at least in part determined by the melting temperature of an oligonucleotide (Tm; calculated with the oligonucleotide properties calculator (www.unc.edu/~cail/biotool/oligo/index.html) for single stranded RNA using the basic Tm and the nearest neighbor model), and/or the free energy of the AON-target exon complex (using RNA structure version 4.5). If a Tm is too high, the oligonucleotide is expected to be less specific. An acceptable Tm and free energy depend on the sequence of the oligonucleotide. Therefore, it is difficult to give preferred ranges for each of these parameters. An acceptable Tm may be ranged between 35 and 70° C. and an acceptable free energy may be ranged between 15 and 45 kcal/mol.

The skilled person may therefore first choose an oligonucleotide as a potential therapeutic compound as binding and/or being complementary to SEQ ID NO: 6, 7, or 8 or a part thereof as defined later herein. The skilled person may check that said oligonucleotide is able to bind to said sequences as earlier defined herein. Optionally in a second step, he may use the invention to further optimize said oligonucleotide by checking for the absence of CpG and/or by optimizing its Tm and/or free energy of the AON-target complex. He may try to design an oligonucleotide wherein preferably no CpG and/or wherein a more acceptable Tm and/or free energy are obtained by choosing a distinct sequence of CEP290 (including SEQ ID NO: 6, 7 or 8) to which the oligonucleotide is complementary. Alternatively, if an oligonucleotide complementary to a given stretch within SEQ ID NO: 6, 7 or 8, comprises a CpG, and/or does not have an acceptable Tm and/or free energy, the skilled person may improve any of these parameters by decreasing the length of the oligonucleotide, and/or by choosing a distinct stretch within any of SEQ ID NO: 6, 7 or 8 to which the oligonucleotide is complementary and/or by altering the chemistry of the oligonucleotide.

At any step of the method, an oligonucleotide of the invention is preferably an olignucleotide, which is still able to exhibit an acceptable level of functional activity. A functional activity of said oligonucleotide is preferably to induce the skipping of the aberrant 128 nucleotide CEP290 exon (SEQ ID NO. 4) to a certain extent, to provide an individual with a functional CEP290 protein and/or mRNA and/or at least in part decreasing the production of an aberrant CEP290 protein and/or mRNA. In a preferred embodiment, an oligonucleotide is said to induce skipping of the aberrant 128 nucleotide CEP290 exon (SEQ ID NO: 4), when the aberrant 128 nucleotide CEP290 exon (SEQ ID NO: 4) skipping percentage as measured by real-time quantitative RT-PCR analysis (is at least 30%, or at least 35%, or at least 40%, or at least 45%, or at least 50%, or at least 55%, or at least 60%, or at least 65%, or at least 70%, or at least 75%, or at least 80%, or at least 85%, or at least 90%, or at least 95%, or 100%.

Preferably, a nucleic acid molecule according to the invention, preferably an oligonucleotide, which comprises a sequence that is complementary or substantially complementary to a nucleotide sequence as shown in SEQ ID NO: 6, preferably SEQ ID NO: 7, more preferably SEQ ID NO: 8, or part thereof of CEP290 is such that the (substantially) complementary part is at least 50% of the length of the oligonucleotide according to the invention, more preferably at least 60%, even more preferably at least 70%, even more preferably at least 80%, even more preferably at least 90% or even more preferably at least 95%, or even more preferably 98% or even more preferably at least 99%, or even more preferably 100%. Preferably, an oligonucleotide according to the invention comprises or consists of a sequence that is complementary to part of SEQ ID NO: 6, 7 or 8. As an example, an oligonucleotide may comprise a sequence that is complementary to part of SEQ ID NO: 6, 7 or 8 and additional flanking sequences. In a more preferred embodiment, the length of said complementary part of said oligonucleotide is of at least 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 115, 120, 125, 130, 135, 140, 141, 142 or 143 nucleotides Additional flanking sequences may be used to modify the binding of a protein to the oligonucleotide, or to modify a thermodynamic property of the oligonucleotide, more preferably to modify target RNA binding affinity.

It is thus not absolutely required that all the bases in the region of complementarity are capable of pairing with bases in the opposing strand. For instance, when designing the oligonucleotide one may want to incorporate for instance a residue that does not base pair with the base on the complementary strand. Mismatches may, to some extent, be allowed, if under the circumstances in the cell, the stretch of nucleotides is sufficiently capable of hybridizing to the complementary part. In this context, "sufficiently" preferably means that using a gel mobility shift assay as described in example 1 of EP1619249, binding of an oligonucleotide is detectable. Optionally, said oligonucleotide may further be tested by transfection into retina cells of patients. Skipping of a targeted exon may be assessed by RT-PCR (as described in EP1619249). The complementary regions are preferably designed such that, when combined, they are specific for the exon in the pre-mRNA. Such specificity may be created with various lengths of complementary regions as this depends on the actual sequences in other (pre-)mRNA molecules in the system. The risk that the oligonucleotide also will be able to hybridize to one or more other pre-mRNA molecules decreases with increasing size of the oligonucleotide. It is clear that oligonucleotides comprising mismatches in the region of complementarity but that retain the capacity to hybridize and/or bind to the targeted region (s) in the pre-mRNA, can be used in the present invention. However, preferably at least the complementary parts do not comprise such mismatches as these typically have a higher efficiency and a higher specificity, than oligonucleotides having such mismatches in one or more complementary regions. It is thought, that higher hybridization strengths, (i.e. increasing number of interactions with the opposing strand) are favorable in increasing the efficiency of the process of interfering with the splicing machinery of the system. Preferably, the complementarity is from 90% to 100%. In general this allows for 1 or 2 mismatch(es) in an oligonucleotide of 20 nucleotides or 1, 2, 3 or 4 mismatches in an oligonucleotide of 40 nucleotides, or 1, 2, 3, 4, 5 or 6 mismatches in an oligonucleotide of 60 nucleotides, etc.

An exon skipping molecule of the invention is preferably an isolated molecule.

An exon skipping molecule of the invention is preferably a nucleic acid molecule or nucleotide-based molecule, preferably an (antisense) oligonucleotide, which is complementary to a sequence selected from SEQ ID NO: 6, 7 and 8.

A preferred exon skipping molecule, according to the invention is a nucleic acid molecule comprising an antisense oligonucleotide which antisense oligonucleotide has a length from about 8 to about 143 nucleotides, more preferred from about 8 to 60, more preferred 10 to about 40 nucleotides, more preferred from about 12 to about 30 nucleotides, more preferred from about 14 to about 28 nucleotides, nucleotides, most preferred about 20 nucleotides, such as 15 nucleotides, 16 nucleotides, 17 nucleotides, 18 nucleotides, 19 nucleotides, 20 nucleotides, 21 nucleotides, 22 nucleotides, 23 nucleotides, 24 nucleotides or 25 nucleotides.

A preferred exon skipping molecule of the invention is an antisense oligonucleotide comprising or consisting of from 8 to 143 nucleotides, more preferred from 10 to 40 nucleotides, more preferred from 12 to 30 nucleotides, more preferred from 14 to 20 nucleotides, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 115, 120, 125, 130, 135, 140, 141, 142 or 143 nucleotides.

In certain embodiments, the invention provides an exon skipping molecule comprising or preferably consisting of an antisense oligonucleotide selected from the group consisting of: SEQ ID NO: 10, SEQ ID NO: 11, and SEQ ID NO: 12.

In a more preferred embodiment, the invention provides an exon skipping molecule comprising or preferably consisting of the antisense oligonucleotide SEQ ID NO: 10. It was found that this molecule is very efficient in modulating splicing of the aberrant 128 nucleotide CEP290 exon. This preferred exon skipping molecule of the invention comprising SEQ ID NO: 10 preferably comprises from 8 to 143 nucleotides, more preferred from 10 to 40 nucleotides, more preferred from 10 to 30 nucleotides, more preferred from 12 to 20 nucleotides, more preferably from 14 to 18 or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 115, 120, 125, 130, 135, 140, 141, 142 or 143 nucleotides.

In another more preferred embodiment, the invention provides an exon skipping molecule comprising or preferably consisting of the antisense oligonucleotide SEQ ID NO: 11. It was found that this molecule is very efficient in modulating splicing of the aberrant 128 nucleotide CEP290 exon. This preferred exon skipping molecule of the invention comprising SEQ ID NO: 11 preferably comprises from 8 to 143 nucleotides, more preferred from 10 to 40 nucleotides, more preferred from 10 to 30 nucleotides, more preferred from 12 to 20 nucleotides, more preferably from 14 to 18, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 115, 120, 125, 130, 135, 140, 141, 142 or 143 nucleotides.

In another more preferred embodiment, the invention provides an exon skipping molecule comprising or preferably consisting of the antisense oligonucleotide SEQ ID NO. 12. It was found that this molecule is very efficient in modulating splicing of the aberrant 128 nucleotide CEP290 exon. This preferred exon skipping molecule of the invention comprising SEQ ID NO: 12 preferably comprises from 8 to 143 nucleotides, more preferred from 10 to 40 nucleotides, more preferred from 10 to 30 nucleotides, more preferred from 12 to 20 nucleotides, more preferably from 14 to 18, or preferably comprises or consists of 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 65, 70, 75, 80, 85, 90, 95, 100, 110, 115, 120, 125, 130, 135, 140, 141, 142 or 143 nucleotides.

An exon skipping molecule according to the invention may contain one of more RNA residues, or one or more DNA residues, and/or one or more nucleotide analogues or equivalents, as will be further detailed herein below.

It is preferred that an exon skipping molecule of the invention comprises one or more residues that are modified to increase nuclease resistance, and/or to increase the affinity of the antisense oligonucleotide for the target sequence. Therefore, in a preferred embodiment, the antisense nucleotide sequence comprises at least one nucleotide analogue or equivalent, wherein a nucleotide analogue or equivalent is defined as a residue having a modified base, and/or a modified backbone, and/or a non-natural internucleoside linkage, or a combination of these modifications.

In a preferred embodiment, the nucleotide analogue or equivalent comprises a modified backbone. Examples of such backbones are provided by morpholino backbones, carbamate backbones, siloxane backbones, sulfide, sulfoxide and sulfone backbones, formacetyl and thioformacetyl backbones, methyleneformacetyl backbones, riboacetyl backbones, alkene containing backbones, sulfamate, sulfonate and sulfonamide backbones, methyleneimino and methylenehydrazino backbones, and amide backbones. Phosphorodiamidate morpholino oligomers are modified backbone oligonucleotides that have previously been investigated as antisense agents. Morpholino oligonucleotides have an uncharged backbone in which the deoxyribose sugar of DNA is replaced by a six membered ring and the phosphodiester linkage is replaced by a phosphorodiamidate linkage. Morpholino oligonucleotides are resistant to enzymatic degradation and appear to function as antisense agents by arresting translation or interfering with pre-mRNA splicing rather than by activating RNase H. Morpholino oligonucleotides have been successfully delivered to tissue culture cells by methods that physically disrupt the cell membrane, and one study comparing several of these methods found that scrape loading was the most efficient method of delivery; however, because the morpholino backbone is uncharged, cationic lipids are not effective mediators of morpholino oligonucleotide uptake in cells A recent report demonstrated triplex formation by a morpholino oligonucleotide and, because of the non-ionic backbone, these studies showed that the morpholino oligonucleotide was capable of triplex formation in the absence of magnesium.

It is further preferred that the linkage between the residues in a backbone do not include a phosphorus atom, such as a linkage that is formed by short chain alkyl or cycloalkyl internucleoside linkages, mixed heteroatom and alkyl or cycloalkyl internucleoside linkages, or one or more short chain heteroatomic or heterocyclic internucleoside linkages.

A preferred nucleotide analogue or equivalent comprises a Peptide Nucleic Acid (PNA), having a modified polyamide backbone (Nielsen, et al. (1991) Science 254, 1497-1500). PNA-based molecules are true mimics of DNA molecules in terms of base-pair recognition. The backbone of the PNA is composed of N-(2-aminoethyl)-glycine units linked by peptide bonds, wherein the nucleobases are linked to the backbone by methylene carbonyl bonds. An alternative backbone comprises a one-carbon extended pyrrolidine PNA monomer (Govindaraju and Kumar (2005) Chem. Commun, 495-497). Since the backbone of a PNA molecule contains no charged phosphate groups, PNA-RNA hybrids are usually more stable than RNA-RNA or RNA-DNA hybrids, respectively (Egholm et al (1993) Nature 365, 566-568).

A further preferred backbone comprises a morpholino nucleotide analog or equivalent, in which the ribose or deoxyribose sugar is replaced by a 6-membered morpholino ring. A most preferred nucleotide analog or equivalent comprises a phosphorodiamidate morpholino oligomer (PMO), in which the ribose or deoxyribose sugar is replaced by a 6-membered morpholino ring, and the anionic phosphodiester linkage between adjacent morpholino rings is replaced by a non-ionic phosphorodiamidate linkage.

In yet a further embodiment, a nucleotide analogue or equivalent of the invention comprises a substitution of one of the non-bridging oxygens in the phosphodiester linkage. This modification slightly destabilizes base-pairing but adds significant resistance to nuclease degradation. A preferred nucleotide analogue or equivalent comprises phosphorothioate, chiral phosphorothioate, phosphorodithioate, phosphotriester, aminoalkylphosphotriester, H-phosphonate, methyl and other alkyl phosphonate including 3'-alkylene phosphonate, 5'-alkylene phosphonate and chiral phosphonate, phosphinate, phosphoramidate including 3'-amino phosphoramidate and aminoalkylphosphoramidate, thionophosphoramidate, thionoalkylphosphonate, thionoalkylphosphotriester, selenophosphate or boranophosphate.

A further preferred nucleotide analogue or equivalent of the invention comprises one or more sugar moieties that are mono- or disubstituted at the 2', 3' and/or 5' position such as a —OH; —F; substituted or unsubstituted, linear or branched lower (C1-C10) alkyl, alkenyl, alkynyl, alkaryl, allyl, or aralkyl, that may be interrupted by one or more heteroatoms; O-, S-, or N-alkyl; O-, S-, or N-alkenyl; O-, S- or N-alkynyl; O-, S-, or N-allyl; O-alkyl-O-alkyl, -methoxy, -aminopropoxy; methoxyethoxy; -dimethylaminooxyethoxy; and -dimethylaminoethoxyethoxy. The sugar moiety can be a pyranose or derivative thereof, or a deoxypyranose or derivative thereof, preferably ribose or derivative thereof, or deoxyribose or derivative of. A preferred derivatized sugar moiety comprises a Locked Nucleic Acid (LNA), in which the 2'-carbon atom is linked to the 3' or 4' carbon atom of the sugar ring thereby forming a bicyclic sugar moiety. A preferred LNA comprises 2'-O,4'-C-ethylene-bridged nucleic acid (Morita et al. 2001. Nucleic Acid Res Supplement No. 1: 241-242). These substitutions render the nucleotide analogue or equivalent RNase H and nuclease resistant and increase the affinity for the target RNA.

In another embodiment, a nucleotide analogue or equivalent of the invention comprises one or more base modifications or substitutions. Modified bases comprise synthetic and natural bases such as inosine, xanthine, hypoxanthine and other -aza, deaza, -hydroxy, -halo, -thio, thiol, -alkyl, -alkenyl, -alkynyl, thioalkyl derivatives of pyrimidine and purine bases that are or will be known in the art.

It is understood by a skilled person that it is not necessary for all positions in an antisense oligonucleotide to be modified uniformly. In addition, more than one of the aforementioned analogues or equivalents may be incorporated in a single antisense oligonucleotide or even at a single position within an antisense oligonucleotide. In certain embodiments, an antisense oligonucleotide of the invention has at least two different types of analogues or equivalents.

A preferred exon skipping molecule according to the invention comprises a 2'-O alkyl phosphorothioate antisense oligonucleotide, such as 2'-O-methyl modified ribose (RNA), 2'-O-ethyl modified ribose, 2'-O-propyl modified ribose, and/or substituted derivatives of these modifications such as halogenated derivatives.

An effective antisense oligonucleotide according to the invention comprises a 2'-O-methyl ribose with a phosphorothioate backbone.

It will also be understood by a skilled person that different antisense oligonucleotides can be combined for efficiently skipping of the aberrant 128 nucleotide exon of CEP290. In a preferred embodiment, a combination of at least two antisense oligonucleotides are used in a method of the invention, such as two different antisense oligonucleotides, three different antisense oligonucleotides, four different antisense oligonucleotides, or five different antisense oligonucleotides.

An antisense oligonucleotide can be linked to a moiety that enhances uptake of the antisense oligonucleotide in cells, preferably retina cells. Examples of such moieties are cholesterols, carbohydrates, vitamins, biotin, lipids, phospholipids, cell-penetrating peptides including but not limited to antennapedia, TAT, transportan and positively charged amino acids such as oligoarginine, poly-arginine, oligolysine or polylysine, antigen-binding domains such as provided by an antibody, a Fab fragment of an antibody, or a single chain antigen binding domain such as a cameloid single domain antigen-binding domain.

An exon skipping molecule according to the invention may be indirectly administrated using suitable means known in the art. When the exon skipping molecule is an oligonucleotide, it may for example be provided to an individual or a cell, tissue or organ of said individual in the form of an expression vector wherein the expression vector encodes a transcript comprising said oligonucleotide. The expression vector is preferably introduced into a cell, tissue, organ or individual via a gene delivery vehicle. In a preferred embodiment, there is provided a viral-based expression vector comprising an expression cassette or a transcription cassette that drives expression or transcription of an exon skipping molecule as identified herein. Accordingly, the present invention provides a viral vector expressing an exon skipping molecule according to the invention when placed under conditions conducive to expression of the exon skipping molecule. A cell can be provided with an exon skipping molecule capable of interfering with essential sequences that result in highly efficient skipping of the aberrant 128 nucleotide CEP290 exon by plasmid-derived antisense oligonucleotide expression or viral expression provided by adenovirus- or adeno-associated virus-based vectors. Expression may be driven by a polymerase III promoter, such as a U1, a U6, or a U7 RNA promoter. A preferred delivery vehicle is a viral vector such as an adeno-associated virus vector (AAV), or a retroviral vector such as a lentivirus vector and the like. Also, plasmids, artificial chromosomes, plasmids usable for targeted homologous recombination and integration in the human genome of cells may be suitably applied for delivery of an oligonucleotide as defined herein. Preferred for the current invention are those vectors wherein transcription is driven from PolIII promoters, and/or wherein transcripts are in the form fusions with U1 or U7 transcripts, which yield good results for delivering small transcripts. It is within the skill of the artisan to design suitable transcripts. Preferred are PolIII driven transcripts. Preferably, in the form of a fusion transcript with an U1 or U7 transcript. Such fusions may be generated as described (Gorman L et al, 1998 or Suter D et al, 1999).

The exon skipping molecule according to the invention, preferably an antisense oligonucleotide, may be delivered as such. However, the exon skipping molecule may also be encoded by the viral vector. Typically, this is in the form of an RNA transcript that comprises the sequence of an oligonucleotide according to the invention in a part of the transcript.

One preferred antisense oligonucleotide expression system is an adenovirus associated virus (AAV)-based vector. Single chain and double chain AAV-based vectors have been developed that can be used for prolonged expression of small antisense nucleotide sequences for highly efficient skipping of the aberrant 128 nucleotide CEP290 exon.

A preferred AAV-based vector for instance comprises an expression cassette that is driven by a polymerase III-promoter (Pol III). A preferred Pol III promoter is, for example, a U1, a U6, or a U7 RNA promoter.

The invention therefore also provides a viral-based vector, comprising a Pol III-promoter driven expression cassette for expression of an antisense oligonucleotide of the invention for inducing skipping of aberrant 128 nucleotide CEP290 exon.

Improvements in means for providing an individual or a cell, tissue, organ of said individual with an exon skipping molecule according to the invention, are anticipated considering the progress that has already thus far been achieved. Such future improvements may of course be incorporated to achieve the mentioned effect on restructuring of mRNA using a method of the invention. An exon skipping molecule according to the invention can be delivered as is to an individual, a cell, tissue or organ of said individual. When administering an exon skipping molecule according to the invention, it is preferred that the molecule is dissolved in a solution that is compatible with the delivery method. Retina cells can be provided with a plasmid for antisense oligonucleotide expression by providing the plasmid in an aqueous solution. Alternatively, a plasmid can be provided by transfection using known transfection agentia. For intravenous, subcutaneous, intramuscular, intrathecal and/or intraventricular administration it is preferred that the solution is a physiological salt solution. Particularly preferred in the invention is the use of an excipient or transfection agentia that will aid in delivery of each of the constituents as defined herein to a cell and/or into a cell, preferably a retina cell. Preferred are excipients or transfection agentia capable of forming complexes, nanoparticles, micelles, vesicles and/or liposomes that deliver each constituent as defined herein, complexed or trapped in a vesicle or liposome through a cell membrane. Many of these excipients are known in the art. Suitable excipients or transfection agentia comprise polyethylenimine (PEI; ExGen500 (MBI Fermentas)), LipofectAMINE™ 2000 (Invitrogen) or derivatives thereof, or similar cationic polymers, including polypropyleneimine or polyethylenimine copolymers (PECs) and derivatives, synthetic amphiphils (SAINT-18), Lipofectin™, DOTAP and/or viral capsid proteins that are capable of self assembly into particles that can deliver each constituent as defined herein to a cell, preferably a retina cell. Such excipients have been shown to efficiently deliver an oligonucleotide such as antisense nucleic acids to a wide variety of cultured cells, including retina cells. Their high transfection potential is combined with an excepted low to moderate toxicity in terms of overall cell survival. The ease of structural modification can be used to allow further modifications and the analysis of their further (in vivo) nucleic acid transfer characteristics and toxicity.

Lipofectin represents an example of a liposomal transfection agent. It consists of two lipid components, a cationic lipid N-[1-(2,3 dioleoyloxy)propyl]-N,N,N-trimethylammonium chloride (DOTMA) (cp. DOTAP which is the methylsulfate salt) and a neutral lipid dioleoylphosphatidylethanolamine (DOPE). The neutral component mediates the intracellular release. Another group of delivery systems are polymeric nanoparticles.

Polycations such like diethylaminoethylaminoethyl (DEAE)-dextran, which are well known as DNA transfection reagent can be combined with butylcyanoacrylate (PBCA) and hexylcyanoacrylate (PHCA) to formulate cationic nanoparticles that can deliver each constituent as defined herein, preferably an oligonucleotide, across cell membranes into cells.

In addition to these common nanoparticle materials, the cationic peptide protamine offers an alternative approach to formulate an oligonucleotide with colloids. This colloidal nanoparticle system can form so called proticles, which can be prepared by a simple self-assembly process to package and mediate intracellular release of an oligonucleotide. The skilled person may select and adapt any of the above or other commercially available alternative excipients and delivery systems to package and deliver an exon skipping molecule for use in the current invention to deliver it for the prevention, treatment or delay of a CEP290 related disease or condition. "Prevention, treatment or delay of a CEP290 related disease or condition" is herein preferably defined as preventing, halting, ceasing the progression of, or reversing partial or complete visual impairment or blindness that is caused by a genetic defect in the CEP290 gene.

In addition, an exon skipping molecule according to the invention could be covalently or non-covalently linked to a targeting ligand specifically designed to facilitate the uptake into the cell, cytoplasm and/or its nucleus. Such ligand could comprise (i) a compound (including but not limited to peptide(-like) structures) recognising cell, tissue or organ specific elements facilitating cellular uptake and/or (ii) a chemical compound able to facilitate the uptake in to cells and/or the intracellular release of an oligonucleotide from vesicles, e.g. endosomes or lysosomes.

Therefore, in a preferred embodiment, an exon skipping molecule according to the invention is formulated in a composition or a medicament or a composition, which is provided with at least an excipient and/or a targeting ligand for delivery and/or a delivery device thereof to a cell and/or enhancing its intracellular delivery.

It is to be understood that if a composition comprises an additional constituent such as an adjunct compound as later defined herein, each constituent of the composition may not be formulated in one single combination or composition or preparation. Depending on their identity, the skilled person will know which type of formulation is the most appropriate for each constituent as defined herein. In a preferred embodiment, the invention provides a composition or a preparation which is in the form of a kit of parts comprising an exon skipping molecule according to the invention and a further adjunct compound as later defined herein.

If required, an exon skipping molecule according to the invention or a vector, preferably a viral vector, expressing an exon skipping molecule according to the invention can be incorporated into a pharmaceutically active mixture by adding a pharmaceutically acceptable carrier.

Accordingly, the invention also provides a composition, preferably a pharmaceutical composition, comprising an exon skipping molecule according to the invention, or a viral vector according to the invention and a pharmaceutically acceptable excipient. Such composition may comprise a single exon skipping molecule according to the invention, but may also comprise multiple, distinct exon skipping molecules according to the invention. Such a pharmaceutical composition may comprise any pharmaceutically acceptable excipient, including a carrier, filler, preservative, adjuvant, solubilizer and/or diluent. Such pharmaceutically acceptable carrier, filler, preservative, adjuvant, solubilizer and/or diluent may for instance be found in Remington, 2000. Each feature of said composition has earlier been defined herein.

If multiple distinct exon skipping molecules according to the invention are used, concentration or dose defined herein may refer to the total concentration or dose of all oligonucleotides used or the concentration or dose of each exon skipping molecule used or added. Therefore in one embodiment, there is provided a composition wherein each or the total amount of exon skipping molecules according to the invention used is dosed in an amount ranged from 0.1 and 20 mg/kg, preferably from 0.5 and 20 mg/kg.

A preferred exon skipping molecule according to the invention, is for the treatment of a CEP290 related disease or condition of an individual. In all embodiments of the present invention, the term "treatment" is understood to include the prevention and/or delay of the CEP290 related disease or condition. An individual, which may be treated using an exon skipping molecule according to the invention may already have been diagnosed as having a CEP290 related disease or condition. Alternatively, an individual which may be treated using an exon skipping molecule according to the invention may not have yet been diagnosed as having a CEP290 related disease or condition but may be an individual having an increased risk of developing a CEP290 related disease or condition in the future given his or her genetic background. A preferred individual is a human being. In a preferred embodiment the CEP290 related disease or condition is Leber congenital amaurosis.

Accordingly, the present invention further provides an exon skipping molecule according to the invention, or a viral vector according to the invention, or a composition according to the invention for use as a medicament, for treating a CEP290 related disease or condition requiring modulating splicing of CEP290 and for use as a medicament for the prevention, treatment or delay of a CEP290 related disease or condition. A preferred CEP290 related disease or condition is Leber congenital amaurosis. Each feature of said use has earlier been defined herein.

The invention further provides the use of an exon skipping molecule according to the invention, or of a viral vector according to the invention, or a composition according to the invention for the treatment of a CEP290 related disease or condition requiring modulating splicing of CEP290. In a preferred embodiment the CEP290 related disease or condition is Leber congenital amaurosis.

The present invention further provides the use of an exon skipping molecule according to the invention, or of a viral vector according to the invention, or a composition according to the invention for the preparation of a medicament, for the preparation of a medicament for treating a CEP290 related disease or condition requiring modulating splicing of CEP290 and for the preparation of a medicament for the prevention, treatment or delay of a CEP290 related disease or condition. A preferred CEP290 related disease or condition is Leber congenital amaurosis. Therefore in a further aspect, there is provided the use of an exon skipping molecule, viral vector or composition as defined herein for the preparation of a medicament, for the preparation of a medicament for treating a condition requiring modulating splicing of CEP290 and for the preparation of a medicament for the prevention, treatment or delay of a CEP290 related disease or condition. A preferred CEP290 related disease or condition is Leber congenital amaurosis. Each feature of said use has earlier been defined herein.

A treatment in a use or in a method according to the invention is at least one week, at least one month, at least several months, at least one year, at least 2, 3, 4, 5, 6 years or more. Each exon skipping molecule or exon skipping oligonucleotide or equivalent thereof as defined herein for use according to the invention may be suitable for direct administration to a cell, tissue and/or an organ in vivo of individuals already affected or at risk of developing CEP290 related disease or condition, and may be administered directly in vivo, ex vivo or in vitro. The frequency of administration of an oligonucleotide, composition, compound or adjunct compound of the invention may depend on several parameters such as the age of the patient, the mutation of the patient, the number of exon skipping molecules (i.e. dose), the formulation of said molecule. The frequency may be ranged between at least once in two weeks, or three weeks or four weeks or five weeks or a longer time period.

Dose ranges of an exon skipping molecule, preferably an oligonucleotide according to the invention are preferably designed on the basis of rising dose studies in clinical trials (in vivo use) for which rigorous protocol requirements exist. An exon skipping molecule or an oligonucleotide as defined herein may be used at a dose which is ranged from 0.1 and 20 mg/kg, preferably from 0.5 and 20 mg/kg.

In a preferred embodiment, a concentration of an oligonucleotide as defined herein, which is ranged from 0.1 nM and 1 µM is used. Preferably, this range is for in vitro use in a cellular model such as retina cells or retinal tissue. More preferably, the concentration used is ranged from 1 to 400 nM, even more preferably from 10 to 200 nM, even more preferably from 50 to 100 nm. If several oligonucleotides are used, this concentration or dose may refer to the total concentration or dose of oligonucleotides or the concentration or dose of each oligonucleotide added.

In a preferred embodiment, a viral vector, preferably an AAV vector as described earlier herein, as delivery vehicle for a molecule according to the invention, is administered in a dose ranging from $1 \times 10^9$-$1 \times 10^{17}$ virusparticles per injection, more preferably from $1 \times 10^{10}$-$1 \times 10^{12}$ virusparticles per injection.

The ranges of concentration or dose of oligonucleotide(s) as given above are preferred concentrations or doses for in vitro or ex vivo uses. The skilled person will understand that depending on the oligonucleotide(s) used, the target cell to be treated, the gene target and its expression levels, the medium used and the transfection and incubation conditions, the concentration or dose of oligonucleotide(s) used may further vary and may need to be optimized any further.

An exon skipping molecule according to the invention, or a viral vector according to the invention, or a composition according to the invention for use according to the invention may be suitable for administration to a cell, tissue and/or an organ in vino of individuals already affected or at risk of developing a CEP290 related disease or condition, and may be administered in vivo, ex vivo or in vitro. Said exon skipping molecule according to the invention, or a viral vector according to the invention, or a composition according to the invention may be directly or indirectly administrated to a cell, tissue and/or an organ in vivo of an individual already affected by or at risk of developing a CEP290 related disease or condition, and may be administered directly or indirectly in vivo, ex vivo or in vitro. As Leber congenital amaurosis has a pronounced phenotype in retina cells, it is preferred that said cells are retina cells, it is further preferred that said tissue is the retina and/or it is further preferred that said organ comprises or consists of the eye.

The invention further provides a method for modulating splicing of CEP290 in a cell comprising contacting the cell, preferably a retina cell, with an exon skipping molecule according to the invention, or a viral vector according to the invention, or a composition according to the invention. The features of this aspect are preferably those defined earlier herein. Contacting the cell with an exon skipping molecule according to the invention, or a viral vector according to the invention, or a composition according to the invention may be performed by any method known by the person skilled in the art. Use of the methods for delivery of exon skipping molecules, viral vectors and compositions described herein is included. Contacting may be directly or indirectly and may be in vivo, ex vivo or in vitro.

The invention further provides a method for the treatment of a CEP290 related disease or condition requiring modulating splicing of CEP290 of an individual in need thereof, said method comprising contacting a cell, preferably a retina cell, of said individual with an exon skipping molecule according to the invention, or a viral vector according to the invention, or a composition according to the invention. The features of this aspect are preferably those defined earlier herein. Contacting the cell, preferably a retina cell with an exon skipping molecule according to the invention, or a viral vector according to the invention, or a composition according to the invention may be performed by any method known by the person skilled in the art. Use of the methods for delivery of molecules, viral vectors and compositions described herein is included. Contacting may be directly or indirectly and may be in vivo, ex vivo or in vitro. A preferred CEP290 related disease or condition is Leber congenital amaurosis.

Unless otherwise indicated each embodiment as described herein may be combined with another embodiment as described herein.

As can be observed in the experimental section herein, at the RNA level, addition of various AONs targeting the aberrant CEP290 exon indeed resulted in a conversion of aberrantly spliced CEP290 mRNA to correctly spliced CEP290 mRNA. This conversion will coincide with an increased synthesis of the wild-type CEP290 protein.

In fibroblasts (that can be derived from skin cells), CEP290 is abundantly expressed. Therefore, it is to be expected that addition of AONs to cultured fibroblasts from LCA patients will result in an increased amount of wild-type CEP290 protein that is detectable on Western blot, and as such will demonstrate that AON-based therapy will not only redirect normal splicing of CEP290 mRNA but will also result in restoring CEP290 protein function. This experiment is presently ongoing.

In this document and in its claims, the verb "to comprise" and its conjugations is used in its non-limiting sense to mean that items following the word are included, but items not specifically mentioned are not excluded. In addition, reference to an element by the indefinite article "a" or "an" does not exclude the possibility that more than one of the element is present, unless the context clearly requires that there be one and only one of the elements. The indefinite article "a" or "an" thus usually means "at least one". The word "about" or "approximately" when used in association with a numerical value (e.g. about 10) preferably means that the value may be the given value (of 10) more or less 0.1% of the value.

The sequence information as provided herein should not be so narrowly construed as to require inclusion of erroneously identified bases. The skilled person is capable of identifying such erroneously identified bases and knows how to correct for such errors. In case of sequence errors, the sequence of the polypeptide obtainable by expression of the gene present in SEQ ID NO. 1 containing the nucleic acid sequence coding for the polypeptide should prevail.

All patent and literature references cited in the present specification are hereby incorporated by reference in their entirety.

BRIEF DESCRIPTION OF THE DRAWINGS

FIGS. 2a, 2b and 2c AON-based rescue of aberrant CEP290 splicing
A) RT-PCR analysis of CEP290 mRNA isolated from lymphoblastoid cells of one control individuals and two individuals affected with LCA, that were cultured in the absence or presence of a selected AON (AON-3) direct against the aberrant CEP290 exonin a final concentration of 1.0 µM. The upper band represents the aberrant CEP290 splice product, whereas the lower band represents the wild-type CEP290 splice product. M: 100-bp marker. MQ: negative water control.
B) Specificity of AON-based rescue. Similar to A), cells were transfected with AON-3, or a sense oligonucleotide directed to the same target site (SON-3). Left panel: RT-PCR reaction using primers located in exon 26 and exon 27. Right panel: RT-PCR reaction using primers located in exon 26 and exon 31.
C) Dose-dependent rescue of CEP290 mRNA splicing. Similar to A), cells were transfected with different concentrations of the selected AON, ranging from 0.01 to 1.0 µM.

SEQUENCES

All sequences herein are depicted from 5'→3'

TABLE 1

Sequences as set forth in the Sequence Listing

| SEQ ID NO: | SEQ type | Description |
|---|---|---|
| 1 | Genomic DNA | CEP290 |
| 3 | cDNA | CEP290 |
| 3 | PRT | CEP290 protein |
| 4 | DNA | 128 nucleotide aberrant CEP290 exon |
| 5 | PRT | CEP290 aberrant protein |
| 6 | Polynucleotide | 143 nucleotide motif |
| 7 | Polynucleotide | 42 nucleotide motif |
| 8 | Polynucleotide | 24 nucleotide motif |
| 9 | AON-1 | taatcccagcactttaggag |
| 10 | AON-2 | gggccaggtgcggtgg |
| 11 | AON-3 | aactggggccaggtgcs |
| 12 | AON-4 | tacaactggggccaggtg |
| 13 | AON-5 | actcacaattacaactgggg |
| 14 | SON-3 | cgcacctggccccagtt |
| 15 | PCR primer | tgctaagtacagggacatcttgc |
| 16 | PCR primer | agactccacttgttcttttaaggag |

The present invention is further described by the following examples which should not be construed as limiting the scope of the invention.

Unless stated otherwise, the practice of the invention will employ standard conventional methods of molecular biology, virology, microbiology or biochemistry. Such techniques are described in Sambrook et al. (1989) Molecular Cloning, A Laboratory Manual ($2^{nd}$ edition), Cold Spring Harbor Laboratory, Cold Spring Harbor Laboratory Press; in Sambrook and Russell (2001) *Molecular Cloning: A Laboratory Manual*, Third Edition, Cold Spring Harbor Laboratory Press, NY; in Volumes 1 and 2 of Ausubel et al. (1994) *Current Protocols in Molecular Biology, Current Protocols*, USA; and in Volumes I and II of Brown (1998) *Molecular Biology LabFax*, Second Edition, Academic Press (UK); *Oligonicleotide Synthesis* (N. Gait editor); *Nucleic Acid Hybridization* (Hames and Higgins, eds.)

EXAMPLES

Materials and Methods
Design Antisense Oligonucleotides

Figure 1:
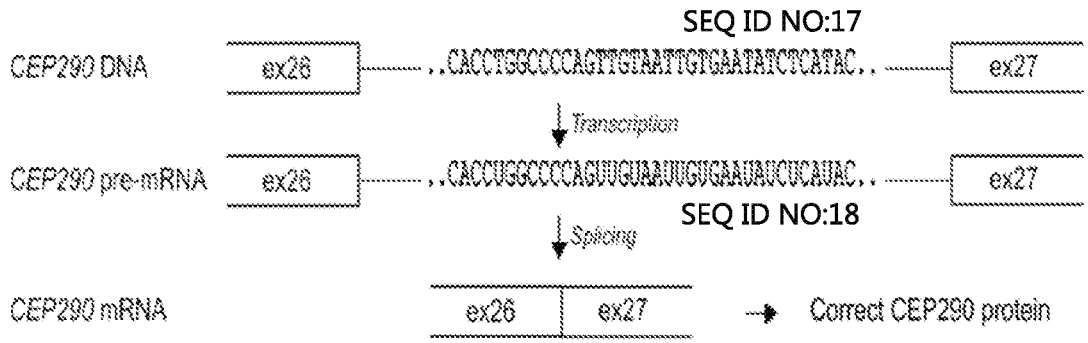
FIG. 1 CEP290 splicing and AON function
A) Normal CEP290 mRNA splicing of exons 26 and 27, resulting in wild-type CEP290 protein (figure discloses SEQ ID NOS 17-18, respectively, in order of appearance).
B) The most frequent LCA-causing mutation is an A-to-G transition (underlined and indicated with an asterisk) in intron 26 of CEP290. This mutation creates a splice donor site, which results in the inclusion of an aberrant exon to ~50% of the CEP290 mRNA and subsequent premature termination of the CEP290 protein (figure discloses SEQ ID NOS 19-20, respectively, in order of appearance).
C) Upon binding of sequence-specific AONs, factors involved in splicing will not recognize the aberrant splice donor site in intron 26, resulting in redirection of normal CEP290 splicing and synthesis of a correct CEP290 protein (figure discloses SEQ ID NOS 19, 21, and 20, respectively, in order of appearance).
Figure 1:
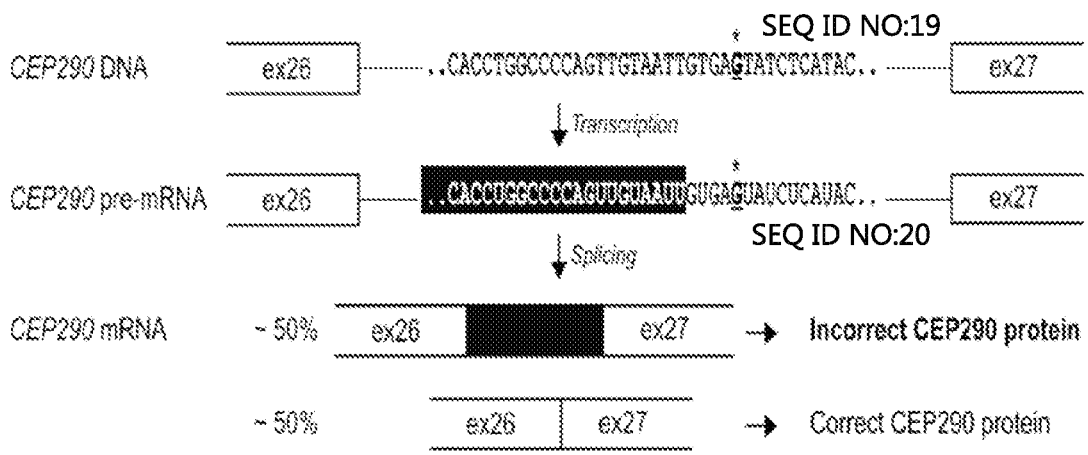
Figure 1:
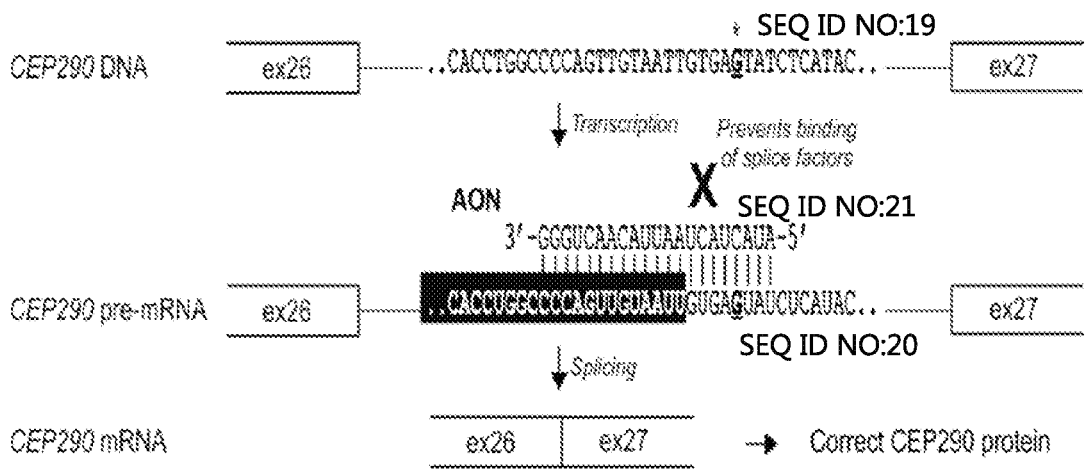

The 128-bp sequence of the aberrant CEP290 exon that is included into the mutant CEP290 mRNA was analyzed for the presence of exonic splice enhancer motifs using the ESE finder 3.0 program (rulai.cshl.edu/cgi-bin/tools/ESE3/esefinder.cgi?process=home). RNA antisense oligonucleotides were purchased from Eurogentec, and designed with a $T_m$ of 58° C., and modified with a 2'-O-methyl group at the sugar chain and a phosphothiorate backbone, and dissolved in phosphate buffered saline.
Cell Culture Human B-lymphoblasts cells of LCA patients homozygously carrying the intronic mutation in CEP290 were immortalized by transformation with the Eppstein-Barr virus, as described previously. (Wall F E, 1995). Cells were cultured in RPMI1640 medium (Gibco) containing 10% (v/v) fetal calf serum (Sigma), 1% 10 U/µl penicillin and 10 µg/µl streptomycin (Gibco), and 1% GlutaMAX (Gibco), at a density of $0.5 \times 10^6$ cells/ml. Cells were passaged twice a week.
Transfection of AONs A day before transfection, $1.0 \times 10^6$ cells were seeded in each well of a 6-wells plate, in a total volume of 2 ml complete medium. Transfection mixtures were prepared by combining 2.5 µl AON in a desired concentration, or distilled water, 5 µl transfection reagent (ExGen in vitro 500, Fermentas) and 92.5 µl 150 mM NaCl, and incubated at room temperature for 10 minutes, before addition to the cells. Six hours after transfection, 8 ml of low-serum medium (complete medium with only 1% fetal calf serum) was added. Forty-eight hours after transfection, cells were collected and washed with 1×PBS, before directly proceeding to RNA isolation.
RNA Isolation and RT-PCR Total RNA was isolated from transfected lymphoblastoid cells using the Nucleospin RNA II isolation kit (Machery Nagel), according to manufacturer's protocol. Subsequently, 1 µg of total RNA was used for cDNA synthesis using the iScript cDNA synthesis kit (Bio-Rad). Five percent of the cDNA was used for each PCR reaction. Part of the CEP290 cDNA was amplified under standard PCR conditions supplemented with 5% Q-solution (Qiagen), and using forward primer tgctaagtacagggacatcttgc (SEQ ID NO: 15) and reverse primer agactccacttgttcttttaaggag (SEQ ID NO: 16) that are located in exon 26 and exon 27 of the human (CEP290 gene, respectively. PCR products were resolved on a 1.5% agarose gel. Bands presumably representing correctly and aberrantly spliced CEP290 were excised from the gel, purified using Nucleospin Extract II isolation kit and sequenced from both strands with the ABI PRISM Big Dye Terminator Cycle Sequencing V2.0 Ready Reaction kit and the ABI PRISM 3730 DNA analyzer (Applied Biosystems).
Introduction Here, we describe the use of AONs to redirect normal splicing of CEP290 in patient-derived lymphoblast cells, and show a sequence-specific and dose-dependent decrease in levels of aberrantly spliced (CEP290, thereby revealing the potential of AON-based therapy to treat CEP290-associated LCA.
Results The intronic CEP290 mutation (c.2991+1655A>G) creates a cryptic splice donor site that results in the inclusion of an aberrant exon into the CEP290 mRNA (FIG. 1). Addition of AONs directed against the aberrant exon would prevent the insertion of this exon by preventing the binding of factors that are essential for splicing such as the U1- and U2snRNP complexes, and serine-arginine rich proteins, thereby restoring normal CEP290 splicing and protein synthesis (FIG. 1). AONs can target splice sites as well as exonic sequences, although in the particular case of the Duchenne muscular dystrophy DMD gene, AONs targeting exonic regions tend to outperform those that target the splice sites (Aartsma-Rus et al, 2010). In addition, previous studies have suggested a positive correlation between the capability of AONs to induce exon skipping and the presence of predicted SC35 splice factor binding sites in the target sequence (Aartsma-Rus et al, 2008). To design an AON with high exon-skipping potential, the aberrant CEP290 exon (128 nucleotides exonic sequence plus 15 nucleotides of intronic sequence on each side) was scrutinized for exonic splice enhancer binding motifs, using the ESE finder 3.0 program (Smith et al, 2006). At the 3'-end of the aberrant exon, two SC35-binding motifs were predicted (data not shown). Hence, the first AON was designed such that it encompassed these two motifs (designated AON-3, SEQ ID NO: 11), and being complementary to the CEP290 mRNA.

Figure 2B:
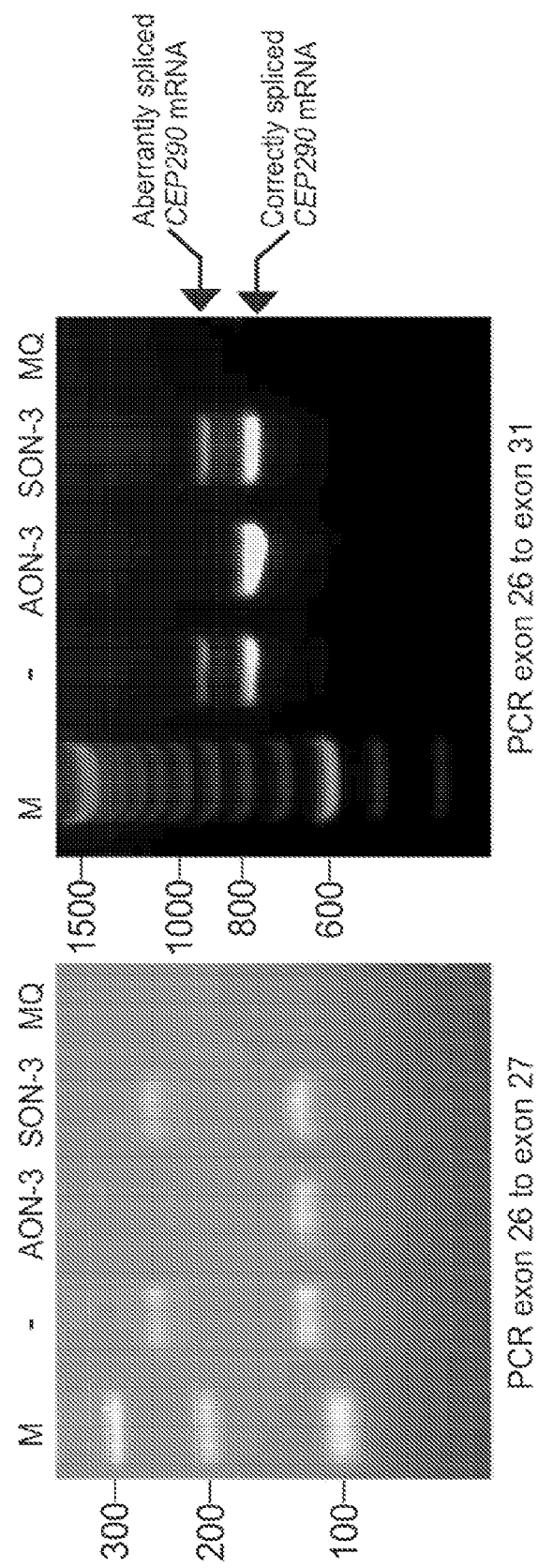
Figure 2C:
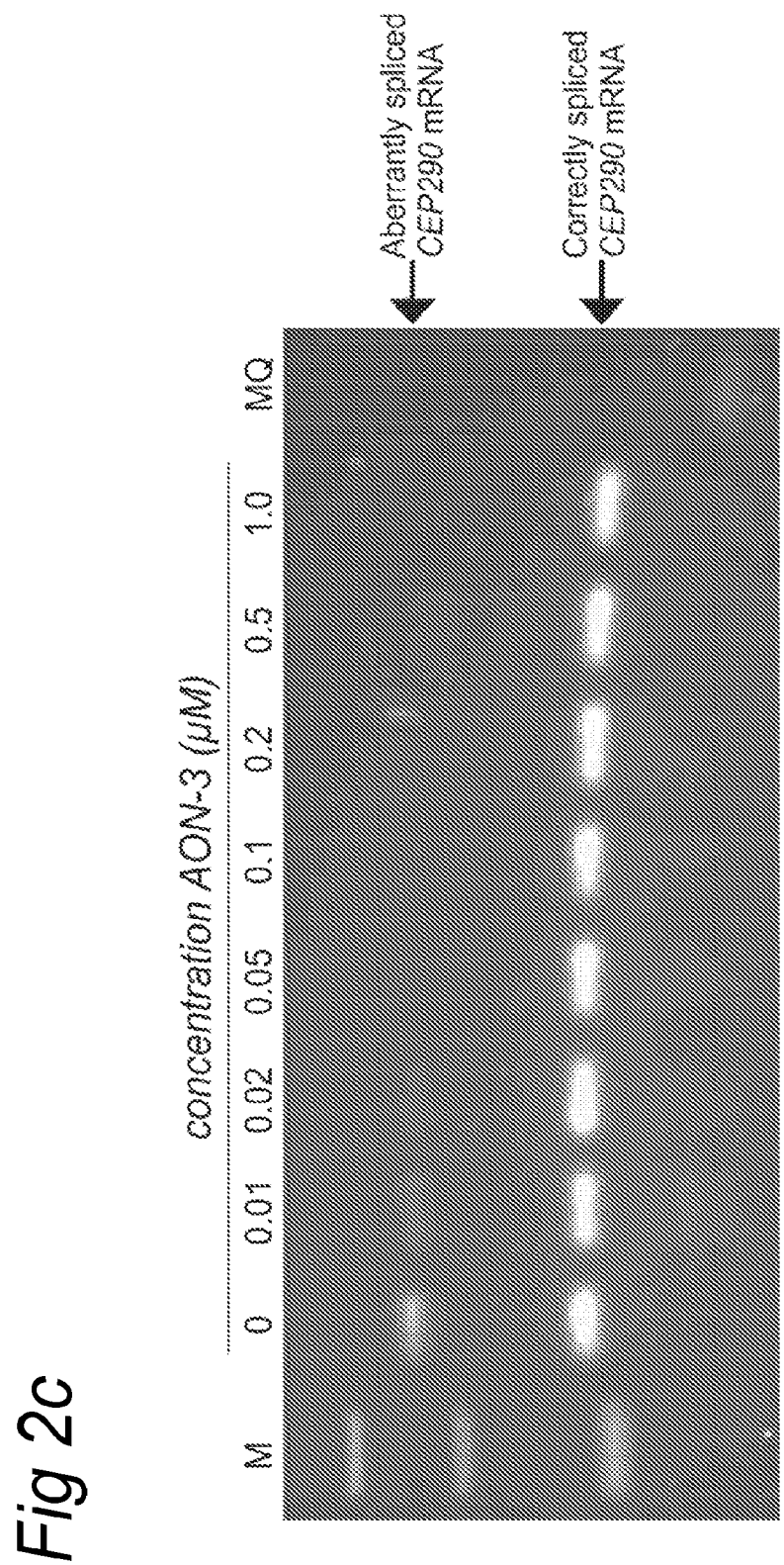

To determine whether AON-3 has exon-skipping potential in vitro, immortalized lymphoblastoid cells of two unrelated individuals with LCA homozygously carrying the intronic CEP290 founder mutation c.2991+1655A>G, as well as one control individual were cultured in the absence or presence of 1 µM AON-3. As expected, in the control individual, only a band representing correctly spliced CEP290 was observed, whereas in both affected individuals two products were present, one representing correctly spliced, and one representing aberrantly spliced CEP290 mRNA. Upon addition of AON-3, a strong decrease in aberrantly spliced CEP290 was noted, in both individuals with LCA (FIG. 2a). Next, the specificity of AON-3 was assessed by transfecting a sense oligonucleotide directed to the same target site (SON-3. SEQ ID NO: 14). RT-PCR analysis showed that in the cells transfected with SON-3, both the aberrantly spliced and the correctly spliced CEP290 mRNA molecules are still present (FIG. 2b, left panel), demonstrating the specificity of the antisense sequence. Using an additional pair of primers that amplifies larger products, similar results were obtained (FIG. 2b, right panel). Interestingly, the decrease in aberrantly spliced CEP290 appears to coincide with an increased intensity of the product representing correctly spliced CEP290 mRNA. These data indicate that the aberrant product is not degraded, but that the AON transfection truly induces exon skipping, resulting in the synthesis of more correctly spliced wild-type CEP290 mRNA. To determine the effective dose of AON-3, cells were transfected with various concentrations of AON-3, ranging from 0.01 to 1.0 µM. Even at the lowest concentration of 0.01 µM, a marked reduction in aberrantly spliced CEP290 was observed. The maximum amount of exon skipping was observed at 0.05 or 0.1 μM of AON, indicating that these concentrations are sufficient to convert almost all aberrantly spliced CEP290 (FIG. 2c).

Figure 3A:
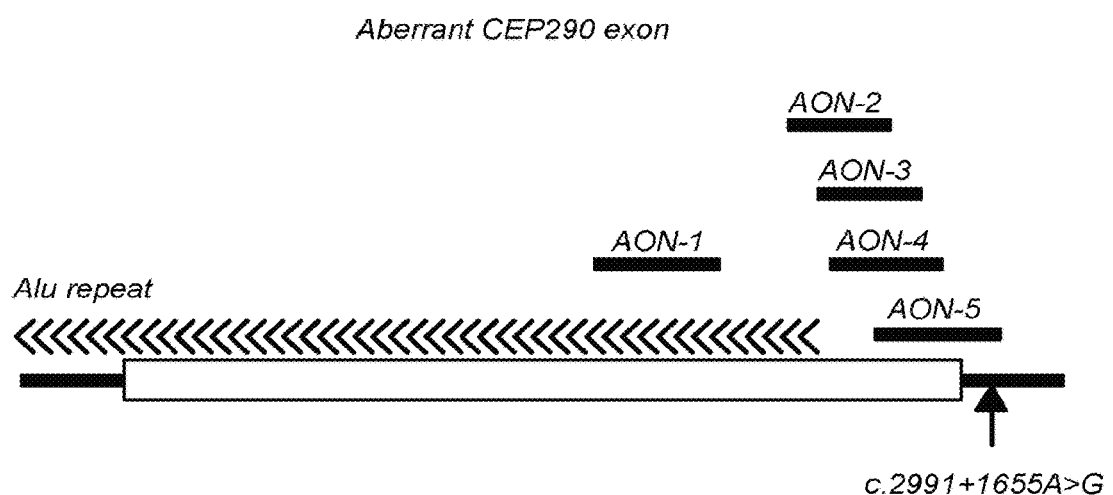
FIGS. 3a and 3b Sequence specificity in AON-based rescue of aberrant CEP290 splicing
A) Overview of the aberrant CEP290 exon, and the relative positions of the AONs that were selected. The 5'-end of the aberrant exon is part of an Alu repeat.
B) RT-PCR analysis of CEP290 mRNA isolated from lymphoblastoid cells of an LCA patient that were cultured in the absence or presence of different AONs direct against the aberrant CEP290 exon (AON-1 to -5), or one sense oligonucleotide (SON-3). The AONs and SON were transfected in a final concentration of 0.1 µM. The upper band represents the aberrant CEP290 splice product, whereas the lower band represents the wild-type CEP290 splice product. M: 100-bp marker.
Figure 3B:
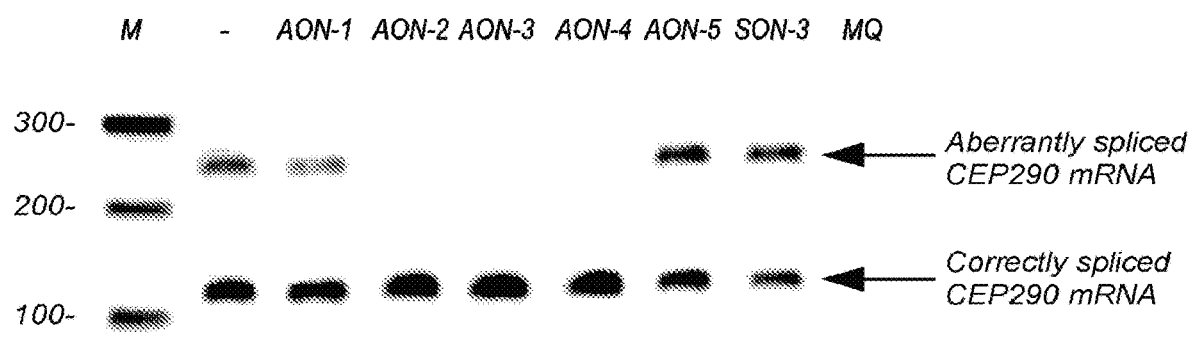

The effectiveness of AONs in splice modulation is thought to merely depend on the accessibility of the target mRNA molecule, and hence may differ tremendously between neighboring sequences. To determine whether this sequence specificity also applies for CEP290, several AONs were designed that target the aberrant CEP290 exon (Table 1). This exon consists of 128 base pairs, the majority of which are part of an Alu repeat, one of the most frequent repetitive elements in the human genome (Schmidt et al, 1982), covering the entire 5'-end of the aberrant exon (FIG. 3a). Hence, the majority of AONs were designed to be complementary to the 3'-end of the aberrant exon or the splice donor site (FIG. 3a). In total, five AONs were transfected at a final concentration of 0.1 μM, which was shown to be optimal for AON-3. Interestingly, besides AON-3, also AON-2 (SEQ ID NO: 10) and AON-4 (SEQ ID NO: 12) resulted in high levels of exon skipping. In contrast, AON-1 (SEQ ID NO: 9) that targets the Alu repeat region, and AON-5 (SEQ ID NO: 13) that is directed against the splice donor site, hardly showed any exon skipping potential (FIG. 3b). These data demonstrate the sequence specificity in AON-based exon skipping of CEP290 and highlight a small region of the aberrant CEP290 exon as a potential therapeutic target.

Discussion

In this study, we explored the therapeutic potential of AONs to correct a splice defect caused by an intronic mutation in CEP290. In immortalized lymphoblast cells of LCA patients homozygously carrying the intronic CEP290 mutation c.2991+1655A>G, transfection of some but not all AONs resulted in skipping of the aberrant exon, thereby almost fully restoring normal CEP290 splicing.

AONs have been the focus of therapeutic research for over a decade, for the treatment of a variety of genetic diseases (Hammond et al, 2011). These strategies include the use of AONs to block the recognition of aberrant splice sites, to alter the ratio between two naturally occurring splice isoforms, to induce skipping of exons that contain protein-truncating mutations, or to induce the skipping of exons in order to restore the reading-frame of a gene that is disrupted by a genomic deletion, allowing the synthesis of a (partially) functional protein (Hammond et al, 2011). The latter approach is already being applied in phase I/II clinical trials for the treatment of patients with Duchenne muscular dystrophy, with promising results (Kinali et al, 2009; van Deutekom et al, 2007).

The intronic CEP290 mutation is an ideal target for AON-based therapy, since this mutation results in the inclusion of an aberrant exon in the CEP290 mRNA which is normally not transcribed. Inducing skipping of this aberrant exon by AONs fully restores the normal CEP290 mRNA, allowing normal levels of CEP290 protein to be synthesized. A second major advantage is that although this AON-approach is a mutation-specific therapeutic strategy, the intronic CEP290 mutation is by far the most frequent LCA-causing mutation.[4] Based on the estimated prevalence of LCA (1:50,000), and the observed frequency of the intronic CEP290 mutation in Northern-Europe (26%) (Coppieters et al, 2010) and the U.S. (10%) (Stone, 2007), at least one thousand and, depending on the frequency of the mutation in other populations, perhaps many more individuals worldwide have LCA due to this mutation. Finally, although the LCA phenotype associated with CEP290 mutations is severe, it appears that the photoreceptor integrity, especially in the macula, as well as the anatomical structure of the visual connections to the brain, are relatively intact in LCA patients with CEP290 mutations, which would allow a window of opportunity for therapeutic intervention (Cideciyan et al, 2007).

The study described here provides a proof-of-principle of AON-based therapy for CEP290-associated LCA in vitro, using immortalized patient lymphoblast cells. In order to determine the true therapeutic potential of this method for treating LCA, additional studies are needed that include the development of therapeutic vectors, and assessment of efficacy and safety in animal models. Although naked AONs, or conjugated to cell-penetrating peptides, can be delivered to the retina by intraocular injections, the limited stability of the AONs would require multiple injections in each individual. In contrast, by using viral vectors, a single subretinal injection would suffice to allow a long-term expression of the therapeutic construct. Previously, others have used recombinant adeno-associated viral (rAAV) vectors carrying U1- or modified U7snRNA constructs to efficiently deliver AON sequences, in the mdx mouse model for DMD, or in DMD patient myoblasts, respectively (Geib et al, 2009; Goyenhalle et al, 2004) In line with this, AONs targeting the aberrant exon of CEP290 could be cloned within such constructs, and delivered to the retina by subretinal injections of rAAV-5 or -8 serotypes that efficiently transduce photoreceptor cells where the endogenous CEP290 gene is expressed (Alloca et al, 2007; Lebherz et al, 2008). Using rAAV-2 vectors, no long-lasting immune response was evoked upon subretinal injections of these vectors in patients with RPE65 mutations (Simonella et al, 2009), and also for rAAV-5 and rAAV-8, immune responses appear to be absent or limited, at least in animal models (Li et al, 2009; Vandenberghe et al, 2011). One final safety aspect concerns the specificity of the sequence that is used to block the splicing of the aberrant CEP290 exon. As stated before, the majority of this exon is part of an Alu repeat, and AONs directed against this repeat will likely bind at multiple sites in the human genome, increasing the chance to induce off-target effects. The AONs that were shown to be effective in this study do not fully target the Alu repeat sequence, but are also not completely unique in the human genome. However, when blasting against the EST database, no exact hits are found, indicating that at the level of expressed genes, these sequences are unlikely to induce off-target effects and deregulate normal splicing of other genes. To further study the efficacy and safety of AON-based therapy for CEP290-associated LCA in vivo, we are currently generating a transgenic knock-in mouse model that carries part of the human CEP290 gene (exon 26 to exon 27, with and without the intronic mutation) which is exchanged with its mouse counterpart.

Compared to gene augmentation therapy, AON-based therapy has a number of advantages. First, in gene augmentation therapy, a ubiquitous or tissue-specific promoter is used to drive expression of the wild-type cDNA encoding the protein that is mutated in a certain patient. For instance in one clinical trial for RPE65 gene therapy, the chicken beta-actin promoter was used (Maguire et al, 2008). Using these but also fragments of the endogenous promoters, it is difficult to control the levels of expression of the therapeutic gene. In some cases, like for the RPE65 protein that has an enzymatic function, expression levels beyond those of the endogenous gene might not be harmful to the retina. For other genes however, including those that encode structural proteins like CEP290, tightly-regulated expression levels might be crucial for cell survival, and overexpression of the therapeutic protein might exert toxic effects. Using AONs, the therapeutic intervention occurs at the pre-mRNA level, and hence does not interfere with the endogenous expression levels of the target gene. A second issue is the use of the viral vector. Of a variety of different recombinant viral vectors, rAAVs are considered to be most suitable for treating retinal dystrophies, because of their relatively high transduction efficiency of retinal cells, and their limited immunogenicity. The major drawback of rAAVs however is their limited cargo size of 4.8 kb. Again, for some genes like RPE65, this is not a problem. For many other retinal genes however, like CEP290 (with an open reading frame of 7.4 kb), but also ABCA4 and USH2A, the size of their full-length cDNAs exceeds the cargo size of the currently available pool of rAAVs. One way to overcome this problem is to express cDNAs that express only partial proteins with residual activity, as has been suggested for CEP290 by expressing the N-terminal region of CEP290 in a zebrafish model (Baye et al, 2011). Other viral vectors, like lentivirus or adenoviruses have a higher cargo capacity that rAAVs (~8 kb), but are less efficient in transducing retinal cells, and adenoviruses have a higher immunogenic potential (den Hollander et al, 2010). For AON-based therapy, the size limitations of AAV are not a problem, since the small size of the AONs and the accompanying constructs easily fit within the available AAVs.

In conclusion, this study shows that administration of AONs to cultured patient cells almost fully corrects a splice defect that is caused by a frequent intronic mutation in CEP290 that causes LCA. These data warrant further research to determine the therapeutic potential of AON-based therapy for CEP290-associated LCA, in order to delay or cease the progression of this devastating blinding disease.

REFERENCE LIST

1. Leber, T. (1869). Uber Retinitis Pigmentosa und angeborene Amaurose. von Graefe's Archives Ophthalmology 15, 1-25.
2. Koenekoop, R. K., Lopez, I, den Hollander, A. I, Allikmets, R., and Cremers, F. P. (2007). Genetic testing for retinal dystrophies and dysfunctions: benefits, dilemmas and solutions. Clin Experiment Ophthalmol 35, 473-485.
3. Stone, E. M. (2007). Leber congenital amaurosis—a model for efficient genetic testing of heterogeneous disorders: LXIV Edward Jackson Memorial Lecture. Am J Ophthalmol 144, 791-811.
4. den Hollander, A. I., Roepman, R., Koenekoop, R. K., and Cremers, F. P. M. (2008). Leber congenital amaurosis: genes, proteins and disease mechanisms. Prog Retin Eye Res 27, 391-419.
5. Estrada-Cuzcano, A., Koenekoop, R. K., Coppieters, F., Kohl, S., Lopez, I., Collin, R. W. J., De Baere, E. B., Roeleveld, D., Marek, J., Bernd, A. et al (2011). IQCB1 mutations in patients with leber congenital amaurosis. Invest Ophthalmol Vis Sci 52, 834-839.
6. den Hollander, A. I., Koenekoop, R. K., Yzer, S., Lopez, I., Arends, M. L., Voesenek, K. E., Zonneveld, M. N., Strom, T. M., Meitinger, T., Brunner, H. G. et al (2006). Mutations in the CEP290 (NPHP6) gene are a frequent cause of Leber congenital amaurosis. Am J Hum Genet 79, 556-561.
7. Perrault, I., Delphin, N, IHanein, S, Gerber, S., Dutier, J. L., Roche, O., foort-Dhellemmes, S, Dollfus, H, Fazzi, E, Munnich, A et al (2007). Spectrum of NPHP6/CEP290 mutations in Leber congenital amaurosis and delineation of the associated phenotype. Hum Mutat 28, 416.
8. Baala, L., Audollent, S., Martinovic, J., Ozilou, C., Babron, M. C., Sivanandamoorthy, S., Saunier, S., Salomon, R., Gonzales, M., Rattenberry, E. et al (2007). Pleiotropic effects of CEP290 (NPHP6) mutations extend to Meckel syndrome. Am J Hum Genet 81, 170-179.
9. Frank, V., den Hollander, A. I., Bruchle, N. O., Zonneveld, M. N., Nurnberg, G., Becker, C., Du, B. G., Kendziorra, H., Roosing, S., Senderek, J. et al (2008). Mutations of the CEP290 gene encoding a centrosomal protein cause Meckel-Gruber syndrome. Hum Mutat 29, 45-52.
10. Helou, J., Otto, E. A., Attanasio, M., Allen, S. J., Parisi, M. A., Glass, I., Utsch, B., Hashmi, S., Fazzi, E., Omran, H. et al (2007). Mutation analysis of NPHP6/CEP290 in patients with Joubert syndrome and Senior-Loken syndrome. J Med Genet 44, 657-663.
11. Valente, E. M., Silhavy, J. L., Brancati, F, Barrano, G., Krishnaswami, S. R., Castori, M., Lancaster, M. A., Boltshauser, E., Boccone, L., Al-Gazali, L. et al (2006). Mutations in CEP290, which encodes a centrosomal protein, cause pleiotropic forms of Joubert syndrome. Nat Genet 38, 623-625.
12. Coppieters, F., Casteels, I., Meire, F., De Jaegere S., Hooghe, S., van Regemorter N., Van Esch H., Matuleviciene, A., Nunes, L., Meersschaut, V. et al (2010). Genetic screening of LCA in Belgium: predominance of CEP290 and identification of potential modifier alleles in AH11 of CEP290-related phenotypes. Hum Mutat 31, E1709-E1766.
13. Littink, K. W., Pott, J. W., Collin, R. W. J., Kroes, H. Y., Verheij, J. B., Blokland, E. A., de Castro Miro M., Hoyng, C. B., Klaver, C. C., Koenekoop, R. K. et al (2010). A novel nonsense mutation in CEP290 induces exon skipping and leads to a relatively mild retinal phenotype. Invest Ophthalmol Vis Sci 51, 3646-3652.
14. Bainbridge, J. W., Smith, A. J., Barker, S. S., Robbie, S., Henderson, R., Balaggan, K., Viswanathan, A., Holder, G. E., Stockman, A., Tyler, N. et al (2008). Effect of gene therapy on visual function in Leber's congenital amaurosis N Engl J Med 358, 2231-2239.
15. Cideciyan, A. V, Aleman, T. S., Boye, S. L., Schwartz, S. B., Kaushal, S., Roman, A. J., Pang, J. J., Sumaroka, A., Windsor, E. A., Wilson, J. M. et al (2008). Human gene therapy for RPE65 isomerase deficiency activates the retinoid cycle of vision but with slow rod kinetics. Proc Natl Acad Sci USA 105, 15112-15117.
16. Hauswirth, W., Aleman, T. S., Kaushal, S., Cideciyan, A. V., Schwartz, S. B., Wang, L., Conlon, T., Boye, S. L., Flotte, T. R., Byrne, B. et al (2008). Phase I Trial of Leber Congenital Amaurosis due to Estrada-Mutations by Ocular Subretinal Injection of Adeno-Associated Virus Gene Vector: Short-Term Results. Hum Gene Ther
17. Maguire, A. M., Simonelli, F., Pierce, E. A., Pugh, E. N., Jr., Mingozzi, F., Bennicelli, J., Banfi, S., Marshall, K. A., Testa, F., Surace, E. M. et al (2008). Safety and efficacy of gene transfer for Leber's congenital amaurosis. N Engl J Med 358, 2240-2248.
18. Maguire, A. M., High, K. A., Auricchio, A., Wright, J. F., Pierce, E. A., Testa, F., Mingozzi, F., Bennicelli, J. L., Ying, G. S., Rossi, S. et al (2009). Age-dependent effects of RPE65 gene therapy for Leber's congenital amaurosis: a phase 1 dose-escalation trial. Lancet 374, 1597-1605.
19. den Hollander, A. I., Black, A., Bennett, J., and Cremers, F. P. M. (2010). Lighting a candle in the dark: advances in genetics and gene therapy of recessive retinal dystrophies. J Clin Invest 120, 3042-3053.
20. Aartsma-Rus, A., Houlleberghs, H., van Deutekom, J. C., van Ommen, G. J., and 't Hoen, P. A. (2010). Exonic sequences provide better targets for antisense oligonucleotides than splice site sequences in the modulation of Duchenne muscular dystrophy splicing. Oligonucleotides 20, 69-77.
21. Aartsma-Rus, A., van, V. L., Hirschi, M., Janson, A. A., Heemskerk, H., de Winter, C. L., de, K. S., van Deutekom, J. C., 't Hoen, P. A., and van Ommen, G. J. (2008). Guidelines for Antisense Oligonucleotide Design and Insight Into Splice-modulating Mechanisms. Mol Ther
22. Smith, P. J., Zhang, C., Wang, J., Chew, S. L., Zhang, M. Q., and Krainer, A. R. (2006). An increased specificity score matrix for the prediction of SF2/ASF-specific exonic splicing enhancers. Hum Mol Genet 15, 2490-2508.
23. Schmid, C. W. and Jelinek, W. R. (1982). The Alu family of dispersed repetitive sequences. Science 216, 1065-1070.
24. Hammond, S. M. and Wood, M. J. (2011). Genetic therapies for RNA mis-splicing diseases. Trends Genet 27, 196-205.
25. Kinali, M., rechavala-Gomeza, V., Feng, L., Cirak, S., Hunt, D., Adkin, C., Guglieri, M., Ashton, E., Abbs, S., Nihoyannopoulos, P. et al (2009). Local restoration of dystrophin expression with the morpholino oligomer AVI-4658 in Duchenne muscular dystrophy: a single-blind, placebo-controlled, dose-escalation, proof-of-concept study. Lancet Neurol 8, 918-928.
26. van Deutekom, J. C., Janson, A. A., Ginjaar, I. B., Frankhuizen, W. S., Aartsma-Rus, A., Bremmer-Bout, M., Den Dunnen, J. T., Koop, K., van der Kooi, A. J., Goemans, N. M. et al (2007). Local dystrophin restoration with antisense oligonucleotide PRO051. N Engl J Med 357, 2677-2686.
27. Coppieters, F., Lefever, S., Leroy, B. P., and De, B. E. (2010). CEP290, a gene with many faces: mutation overview and presentation of CFJ290base. Hum Mutat 31, 1097-1108.
28. Cideciyan, A. V., Aleman, T. S., Jacobson, S. G., Khanna, H., Sumaroka, A., Aguirre, G K., Schwartz, S. B., Windsor, E A, He, S., Chang, B. et al (2007). Centrosomal-ciliary gene CEP290/NPHP6 mutations result in blindness with unexpected sparing of photoreceptors and visual brain: implications for therapy of Leber congenital amaurosis. Hum Mutat 28, 1074-1083.
29. Geib, T. and Hertel, K. J. (2009). Restoration of full-length SMN promoted by adenoviral vectors expressing RNA antisense oligonucleotides embedded in U7 snRNAs. PLoS One 4, e8204.
30. Goyenvalle, A., Vulin, A, Fougerousse, F., Leturcq, F., Kaplan, J. C., Garcia, L., and Danos, O. (2004). Rescue of dystrophic muscle through U7 snRNA-mediated exon skipping. Science 306, 1796-1799.
31. Allocca, M., Mussolino, C., Garcia-Hoyos, M., Sanges, D., Iodice, C., Petrillo, M., Vandenberghe, L. H., Wilson, J. M., Marigo, V., Surace, E. M. et al (2007). Novel adeno-associated virus serotypes efficiently transduce murine photoreceptors. J Virol 81, 11372-11380.
32. Lebherz, C., Maguire, A., Tang, W., Bennett, J., and Wilson, J. M. (2008). Novel AAV serotypes for improved ocular gene transfer. J Gene Med 10, 375-382.
33. Simonelli, F., Maguire, A. M., Testa, F., Pierce, E. A., Mingozzi, F., Bennicelli, J. L, Rossi, S., Marshall, K., Banfi, S., Surace, F. M et al (2009) Gene Therapy for Leber's Congenital Amaurosis is Safe and Effective Through 1.5 Years After Vector Administration. Mol Ther
34. Li, W., Kong, F., Li, X., Dai, X., Liu, X., Zheng, Q., Wu, R., Zhou, X., Lu, F., Chang, B. et al (2009). Gene therapy following subretinal AAV5 vector delivery is not affected by a previous intravitreal AAV5 vector administration in the partner eye. Mol Vis 15, 267-275.
35. Vandenberghe, L. H., Bell, P., Maguire, A. M., Cearley, C. N., Xiao, R., Calcedo, R., Wang, L., Castle, M. J., Maguire, A. C., Grant, R. et al (2011). Dosage Thresholds for AAV2 and AAV8 Photoreceptor Gene Therapy in Monkey. Sci Transl Med 3, 88ra54.
36. Baye, L. M., Patrinostro, X., Swaminathan, S., Beck, J. S., Zhang, Y., Stone, E. M., Sheffield, V. C., and Slusarski, D. C. (2011). The N-terminal region of centrosomal protein 290 (CEP290) restores vision in a zebrafish model of human blindness. Hum Mol Genet 20, 1467-1477.
37. Dorn and Kippenberger, Curr Opin Mol Ther 2008 10(1) 10-20
38. Nielsen, et al. (1991) Science 254, 1497-1500
39. Govindaraju and Kumar (2005) Chem. Commun, 495-497
40. Egholm et al (1993) Nature 365, 566-568
41. Morita et al. 2001. Nucleic Acid Res Supplement No. 1: 241-242
42. Gorman L, et al, Stable alteration of pre-mRNA splicing patterns by modified U7 small nuclear RNAs. Proc Natd Acad Sci USA 1998; 95(9):4929-34
43. Suter D, et al, Double-target antisense U7 snRNAs promote efficient skipping of an aberrant exon in three human beta-thalassemic mutations. Hum Mol Genet 1999; 8(13):2415-23
44. Remington: The Science and Practice of Pharmacy, 20th Edition. Baltimore, MD: Lippincott Williams & Wilkins, 2000

The invention claimed is:

1. An antisense oligonucleotide that is capable of modulating splicing of CEP290 c.2991+1655A>G, wherein the antisense oligonucleotide has a length of 8 to 128 nucleotides and has 90% to 100% complementarity to a sequence within SEQ ID NO:6, and wherein said antisense oligonucleotide comprises one or more modifications to increase nuclease resistance.

2. The antisense oligonucleotide according to claim 1, wherein said antisense oligonucleotide comprises one or more sugar moieties that are mono- or di-substituted at the 2', 3' and/or 5' position.

3. The antisense oligonucleotide according to claim 1, wherein said antisense oligonucleotide comprises at least one phosphorothioate internucleoside linkage.

4. The antisense oligonucleotide according to claim 1, wherein said antisense oligonucleotide comprises a 2'-O alkyl modification.

5. The antisense oligonucleotide according to claim 4, wherein said 2'-O alkyl modification is selected from the group consisting of a 2'-O-methyl modification, a 2'-O-ethyl modification and a 2'-O-propyl modification.

6. The antisense oligonucleotide according to claim 1, wherein said antisense oligonucleotide comprises a 2'-methoxyethoxy modification.

7. The antisense oligonucleotide according to claim 1, wherein said antisense oligonucleotide has a length of 12 to 30 nucleotides.

8. The antisense oligonucleotide according to claim 1, wherein said antisense oligonucleotide has a length of 14 to 20 nucleotides.

9. The antisense oligonucleotide according to claim 1, wherein said antisense oligonucleotide consists of a sequence selected from the group consisting of SEQ ID NO:10, SEQ ID NO:11, and SEQ ID NO:12.

10. The antisense oligonucleotide of any of claims 3-8, wherein the antisense oligonucleotide is 100% complementarity to a sequence within SEQ ID NO: 6.

11. The antisense oligonucleotide of claim 10, wherein all of the nucleotides have an 2'-O-methyl modification.

12. The antisense oligonucleotide of claim 10, wherein all internucleoside linkages are phosphorothioate internucleoside linkages.

13. A pharmaceutical composition comprising an antisense oligonucleotide according to claim 1 and a pharmaceutically acceptable excipient.

14. The pharmaceutical composition according to claim 13, wherein said antisense oligonucleotide comprises one or more sugar moieties that are mono- or di-substituted at the 2', 3' and/or 5' position.

15. The pharmaceutical composition according to claim 13, wherein said antisense oligonucleotide comprises at least one phosphorothioate internucleoside linkage.

16. The pharmaceutical composition according to claim 13, wherein said antisense oligonucleotide comprises a 2'-O alkyl modification.

17. The pharmaceutical composition according to claim 16, wherein said 2'-O alkyl modification is selected from the group consisting of a 2'-O-methyl modification, a 2'-O-ethyl modification and a 2'-O-propyl modification.

18. The pharmaceutical composition according to claim 13, wherein said antisense oligonucleotide comprises a 2'-methoxyethoxy modification.

19. The pharmaceutical composition according to claim 13, wherein said antisense oligonucleotide has a length of 12 to 30 nucleotides.

20. The pharmaceutical composition according to claim 13, wherein said antisense oligonucleotide has a length of 14 to 20 nucleotides.

21. The pharmaceutical composition according to claim 13, wherein said antisense oligonucleotide consists of a sequence selected from the group consisting of SEQ ID NO:10, SEQ ID NO:11, and SEQ ID NO:12.

22. A viral vector expressing an antisense oligonucleotide that is capable of modulating splicing of CEP290 c.2991+1655A>G, wherein said antisense oligonucleotide has a length of 8 to 128 nucleotides and has 90% to 100% complementarity to a sequence within SEQ ID NO:6.

23. A pharmaceutical composition comprising a viral vector according to claim 22 and a pharmaceutically acceptable excipient.

* * * * *